United States Patent [19]

Patterson et al.

[11] Patent Number: 5,444,072
[45] Date of Patent: Aug. 22, 1995

[54] 6-SUBSTITUTED MYCOPHENOLIC ACID AND DERIVATIVES

[75] Inventors: John W. Patterson, Mountain View; David Morgans, Jr., Sunnyvale; David B. Smith, San Bruno, all of Calif.; Francisco X. Talamás, Cuernavaca, Mexico; Dean R. Artis, Menlo Park, Calif.; Alicia Cervantes, Col. Campestre Churubusco, Mexico; Todd R. Elworthy, Palo Alto, Calif.; Mario Fernández, Cuernavaca; Fidencio Franco, San Pedro Xalpa, both of Mexico; Ronald C. Hawley, Woodside, Calif.; Teresa Lara, Toluca, Mexico; David G. Loughhead, Belmont, Calif.; Peter H. Nelson, Los Altos, Calif.; Eric B. Sjogren, Mountain View, Calif.; Alejandra Trejo, Col. Reforma, Mexico; Ann M. Waltos, San Ramon; Robert J. Weikert, Woodside, both of Calif.

[73] Assignee: Syntex (U.S.A.) Inc., Palo Alto, Calif.

[21] Appl. No.: 198,725

[22] Filed: Feb. 18, 1994

[51] Int. Cl.⁶ .................. A61K 31/445; C07D 307/83
[52] U.S. Cl. .................... 514/320; 514/432; 514/473; 549/13; 549/305; 546/196
[58] Field of Search .................. 549/305, 13; 514/473, 514/320, 432; 546/196

[56] References Cited

U.S. PATENT DOCUMENTS

| | | | |
|---|---|---|---|
| 3,825,571 | 7/1974 | Mori et al. | 260/343.3 |
| 3,853,919 | 12/1974 | Mori et al. | 260/343.3 |
| 4,686,234 | 8/1987 | Nelson et al. | 514/469 |
| 4,725,622 | 2/1988 | Nelson et al. | 514/469 |
| 4,727,069 | 2/1988 | Nelson et al. | 514/211 |
| 4,748,173 | 5/1988 | Nelson et al. | 514/211 |
| 4,753,935 | 6/1988 | Nelson et al. | 514/233.5 |
| 4,786,637 | 11/1988 | Allison et al. | 514/233.5 |
| 4,808,592 | 2/1989 | Nelson et al. | 514/233.5 |
| 4,861,776 | 8/1989 | Nelson et al. | 514/233.5 |
| 4,868,153 | 9/1989 | Allison et al. | 514/470 |
| 4,948,793 | 8/1990 | Allison et al. | 514/233.5 |
| 4,952,579 | 8/1990 | Nelson et al. | 514/233.5 |
| 4,959,387 | 9/1990 | Nelson et al. | 524/469 |
| 4,992,467 | 2/1991 | Allison et al. | 514/464 |
| 5,247,083 | 9/1993 | Knox et al. | 544/153 |

FOREIGN PATENT DOCUMENTS 48086860 11/1973 Japan.
1290667 11/1989 Japan.

OTHER PUBLICATIONS

Suzuki, et al., "Antitumor Activity of Derivatives of Mycophenolic Acid", The Jounal of Antibiotics, Mar. 1976, vol. XXIX, No. 3, pp. 275–285.
Carman, et al., "Derivatives of Mycophenolic Acid", Aust. J. Chem., 1978, 31, pp. 353–364.
Nelson, et al., "Synthesis and Immunosuppresive Activity of Some Side-Chain Variants of Mycophenolic Acid", J. Med. Chem., 1990, 33, pp. 833–838.
Patterson, et al., "The Orthoester Claisen Rearrangement in the Synthesis of Mycophenolic Acid", J. Chem. Soc., Chem. Commun., 1991, No. 21, pp. 1579–1580.

Primary Examiner—C. Warren Ivy
Assistant Examiner—A. A. Owens
Attorney, Agent, or Firm—Brian Lewis; David A. Lowin

[57] ABSTRACT

The disclosed 6-substituted derivatives of mycophenolic acid are therapeutic agents advantageous in the treatment of disease states indicated for mycophenolic acid and/or mycophenolate mofetil.

28 Claims, No Drawings

6-SUBSTITUTED MYCOPHENOLIC ACID AND DERIVATIVES

CROSS-REFERENCE TO RELATED APPLICATIONS

This application is related to the following co-pending applications: Ser. No. 08/198,749, Attorney Docket No. 27960, entitled "5-Substituted Derivatives O Mycophenolic Acid"; Ser. No. 08/198,817, Attorney Docket No. 27970, entitled "4-Amino Derivatives Of Mycophenolic Acid"; Ser. No. 08/198,732, Attorney Docket No. 27980, entitled "4-Amino Derivatives of 5-Substituted Mycophenolic Acid"; and Ser. No. 08/198,741, Attorney Docket No. 28000, entitled "4-Amino 6-Substituted Mycophenolic Acid and Derivatives", each filed contemporaneously herewith on Feb. 18, 1994, and each incorporated herein by reference.

FIELD OF THE INVENTION

The present invention relates to mycophenolic acid derivatives where the 6-methoxy substituent has been replaced by other groups, including natural and derivative side chains at the 5-position. The invention is also directed to formulations and methods for treatment.

BACKGROUND INFORMATION

Mycophenolic acid ("MPA") was initially described as a weakly-active antibiotic found in the fermentation broth of *Penicillium brevicompactum,* having the following structure.

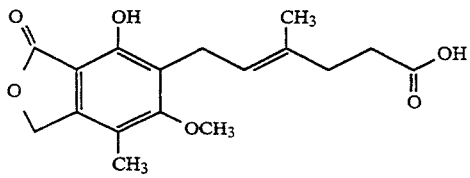

Mycophenolic Acid

MPA and certain related compounds, such as mycophenolate mofetil (the morpholinoethyl ester of MPA), having the following structure:

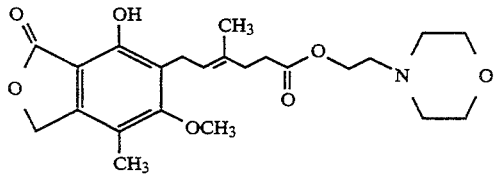

have more recently been described as having particularly advantageous properties as immunosuppressant drugs.

Various derivatives of mycophenolic acid, their synthesis and uses in the treatment of autoimmune disorders, psoriasis, inflammatory diseases, including, in particular, rheumatoid arthritis, tumors, viruses, and for treatment of allograft rejection, are described in U.S. Pat. Nos. 4,686,234; 4,725,622; 4,727,069; 4,748,173; 4,753,935; 4,786,637; 4,808,592; 4,861,776; 4,868,153; 4,948,793; 4,952,579; 4,959,387; 4,992,467; 5,247,083; and U.S. patent application Ser. No. 07/927,260, filed Aug.7, 1992.

As immunosuppressive agents, the previously described esters and derivatives of mycophenolic acid are useful in treating auto-immune related disorders, glomerulonephritis and hepatitis, and in preventing allograft rejection. As anti-inflammatory agents, they are useful in treating rheumatoid arthritis. As anti-tumor agents, they are useful in treating solid tumors and malignancies of lymphoreticular origins.

See also U.S. Pat. Nos. 3,825,571 and 3,853,919; Japanese Pat. No. J 01290667; *J. Med. Chem.,* 33(2), 833–8 (1990); *Austr. J. Chem.,* 31(2), 353–64, (1978); and *J. Antibiot.,* 29(3), 275–85, 286–91 (1976). The disclosed compounds are described as having anti-tumor, immunosuppressive, anti-viral, anti-arthritic and/or anti-psoriatic activities. The article by J. W. Patterson and G. Huang, *Chemical Communications,* 1579 (1991) describes synthetic methodology of interest with respect to such compounds.

The above-cited patents, publications, and the references/publications referenced therein, are all incorporated herein by reference.

SUMMARY OF THE INVENTION

One aspect of the present invention concerns mycophenolic acid derivatives, i.e., the compounds of Formula A:

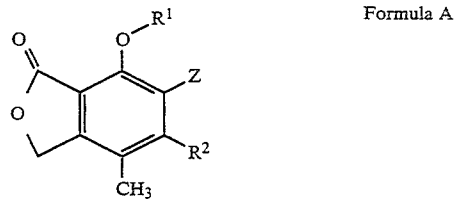

Formula A wherein:
$R^1$ is H or $C(O)R^{10}$, where $R^{10}$ is lower alkyl, aryl or NH-aryl;
$R^2$ is lower alkyl, cycloalkyl, vinyl, fluorovinyl, difluorovinyl, trifluorovinyl, alkenyl, —C≡C—$R^{11}$, allenyl, CHO or $CH_2OR^{12}$, where
$R^{11}$ is H or lower alkyl, and
$R^{12}$ is H or 4-methoxybenzyl; and
Z is a side chain selected from Formulae ZA, ZB, ZC, ZD, ZE, ZF, ZG and ZH:

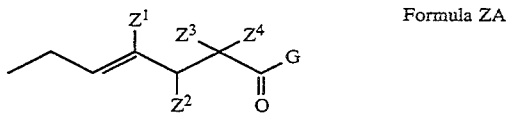

Formula ZA wherein:
$Z^1$ is H, lower alkyl, halo or $CF_3$;
$Z^2$ is H, lower alkyl, lower alkoxy, aryl, or $CH_2$—$Z^{11}$, where
$Z^{11}$ is halo, CN, aryl or heteroaryl;
$Z^3$ is H, lower alkyl, lower alkenyl, lower alkoxy, phenyl, or $S(O)_m$-lower alkyl, where m is 0, 1 or 2;
$Z^4$ is H, lower alkyl, or phenyl;
or $Z^3$ and $Z^4$ taken together with the carbon to which they are attached form cycloalkyl of three to five carbon atoms; and
G is OH, lower alkoxy, lower thioalkyl, $NG^1G^2$, O—$(CH_2)_n$—$NG^1G^2$, or O—$(CH_2)_n$—N=$G^3$, where
n is an integer from 1 to 6,
$G^1$ is H or lower alkyl,
$G^2$ is H or lower alkyl, and =G³ is lower alkylene of four to six carbon atoms, or lower alkylene of three to five carbon atoms plus one member that is —O—, —S—, or —N(G⁴)— where G⁴ is H or lower alkyl; or

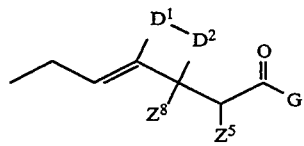

Formula ZB wherein:
Z⁵ is H or lower alkyl;
Z⁸ is H, lower alkyl or forms a double bond with D²;
D¹ and D² together with their adjacent carbon atoms form an optionally substituted, saturated or unsaturated carbocyclic or heterocyclic ring of 3 to 7 atoms; and
G is as defined above; or

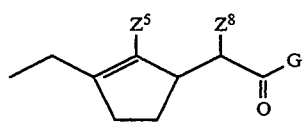

Formula ZC wherein:
Z⁸ is H or lower alkyl; and
Z⁵ and G are as defined above; or

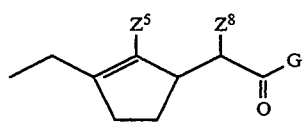

Formual ZD wherein:
D³ is —CH₂— or —CH₂—CH₂—; and
G is as defined above; or

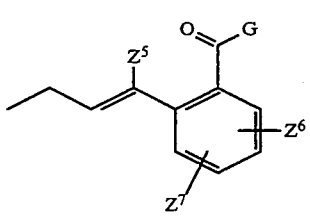

Formula ZE wherein:
Z⁶ is H, lower alkyl, COOH, NH₂, azido or halo;
Z⁷ is H, lower alkyl or halo; and
Z⁵ and G are as defined above; or

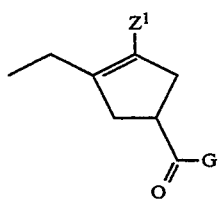

Formula ZF wherein:
Z¹ and G are as defined above; or

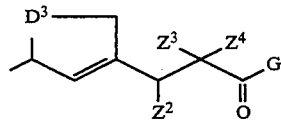

Formula ZG wherein:
D³, Z², Z³, Z⁴ and G are as defined above; or

Formula ZH wherein:
D⁴ is —CH₂—, —CH₂—CH₂—, —CH₂—CH₂—CH₂—, —O—, or —O—CH₂—; and
Z¹ and G are as defined above;
and the pharmaceutically acceptable salts thereof.

In another aspect, the invention relates to a pharmaceutical composition containing a therpeutically effective amount of a compound of Formula A or a pharmaceutically acceptable salt thereof admixed with at least one pharmaceutically acceptable excipient.

In still another aspect, the invention relates to a method of treating immune, inflammatory, tumor, proliferative, viral and psoriatic disorders in a mammal by administering to a mammal in need of such treatment a therapeutically effective amount of a compound of Formula A or a pharmaceutically acceptable salt thereof.

DETAILED DESCRIPTION OF THE INVENTION

Definitions and General Parameters

The following definitions are set forth to illustrate and define the meaning and scope of the various terms used to describe the invention herein. The term "alkyl" refers to a fully saturated monovalent radical containing only carbon and hydrogen, and which may be a cyclic, branched or straight chain radical. This term is further exemplified by radicals such as methyl, ethyl, t-butyl, pentyl, pivalyl, heptyl, cyclopropyl, cyclopentyl, cyclohexyl, cyclohexylmethyl, adamantyl, and the like.

The term "lower alkyl" refers to a cyclic, branched or straight chain monovalent alkyl radical of one to six carbon atoms. This term is further exemplified by such radicals as methyl, ethyl, n-propyl, isopropyl, n-butyl, t-butyl, i-butyl (or 2-methylpropyl), cyclopropyl-methyl, i-amyl, n-amyl, and hexyl.

The term "alkylene" refers to a fully saturated divalent radical containing only carbon and hydrogen, and which may be a branched or straight chain radical. This term is further exemplified by radicals such as methylene, ethylene, n-propylene, t-butylene, i-pentylene, and n-heptylene.

The term "lower alkylene" refers to a fully saturated divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "lower alkenyl" refers to an unsaturated monovalent hydrocarbon radical of one to six carbon atoms. This term is further exemplified by such radicals as vinyl, prop-2-enyl, pent-3-enyl, and hex-5-enyl.

The term "lower acyl" refers to the group —C(O)—R', where R' is lower alkyl.

The term "aryl" refers to a monovalent unsaturated aromatic carbocyclic radical having a single ring (e.g., phenyl) or two condensed rings (e.g., naphthyl), which can optionally be mono-, di- or tri-substituted, independently, with OH, COOH, lower alkyl, lower alkoxy, chloro, fluoro, trifluoromethyl and/or cyano.

The term "heteroatom" refers to oxygen, sulfur and nitrogen, unless otherwise specified.

The term "heteroaryl" refers to a monovalent aromatic carbocyclic radical having at least one heteroatom within the ring, such as quinolyl, benzofuranyl, pyridyl, morpholinyl and indolyl, which can optionally be mono-, di- or tri-substituted, independently, with OH, COOH, lower alkyl, lower alkoxy, chloro, fluoro, trifluoromethyl and/or cyano.

The term "optionally substituted, saturated or unsaturated carbocyclic or heterocyclic ring of 3 to 7 atoms" as used with reference to a side chain of Formula ZB encompases side chains of the following structures:

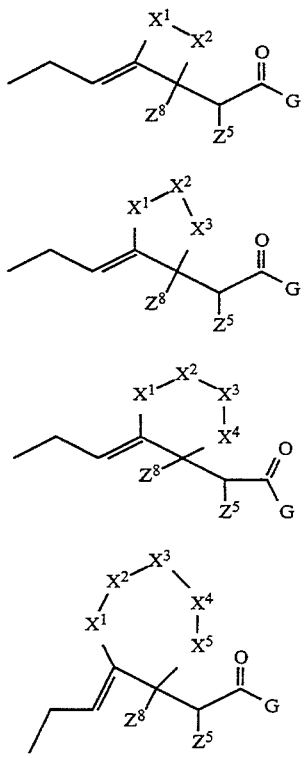

where the line inside each respective ring indicates the optional presence of a double bond and $X^1$, $X^2$, $X^3$, $X^4$ and $X^5$ can independently be —CHX$^a$—, —C(O)—, —C(N—X$^b$)—, —C(N—NX$^d$X$^e$)—, —O—, —S—, —S(O)—, —S(O)$_2$— or —NX$^c$—,
where
  $X^a$ is H, lower alkyl or forms a double bond;
  $X^b$ is acyl, carbamoyl or ureido;
  $X^c$ is lower alkyl, C(O)X$^d$, S(O)$_2$X$^d$ or C(O)NX$^d$X$^e$; and
  $X^d$ and $X^e$ are independently H or lower alkyl;
provided that if more than one heteroatom is present such heteroatoms are separated by at least one carbon atom.

The term "halo" refers to fluoro, bromo, chloro and iodo, unless otherwise specified.

The definition "=G$^3$ is lower alkylene of four to six carbon atoms, or lower alkylene of three to five carbon atoms plus one member that is —O—, —S—, or —N(G$^4$)—" means that —N=G$^3$ represents a heterocyclic derivative such as pyrrolidinyl, piperidinyl, hexamethyleneiminyl, imidazolidino, thiazolidino, morpholino, thiomorpholino, piperazino, thiopentamethyleneimino, and the like.

"Optional" or "optionally" means that the subsequently described event or circumstance may or may not occur, and that the description includes instances where said event or circumstance occurs and instances in which it does not.

A "pharmaceutically acceptable salt" is a salt that retains the biological effectiveness and properties of the compounds of formula I and which are not biologically or otherwise undesirable. Salts may be derived from acids or bases. The term "pharmaceutically acceptable anion" refers to the anion of acid addition salts. "Pharmaceutically acceptable cation" refers to the cation of base addition salts.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like.

The base addition salts may be derived from inorganic bases, and include sodium, potassium, lithium, ammonium, calcium, magnesium salts, and the like. Salts derived from organic bases include those formed from primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

The term "treatment" or "treating" means any treatment of a disease in a mammal, including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

The term "effective amount" means a dosage sufficient to provide treatment for the disease state being treated. This will vary depending on the patient, the disease and the treatment being effected.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The compounds of the invention may possess one or more asymmetric centers, and can be produced as a racemic mixture or as individual enantiomers or diastereoisomers. The number of stereoisomers present in any given compound of Formula A depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula A by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated. Specific examples of the separation of isomers are set forth in the Examples.

"Structure of Formula A" refers to the generic structure of the compounds of the invention. The chemical bonds indicated as a wavy line, for example for $Z^3$ and $Z^4$ in Formula 105 below, indicate a racemic mixture.

Nomenclature

The naming and numbering of the compounds of the present invention is illustrated below.

The isobenzofuranyl nucleus of the compounds of Formula A is numbered as follows:

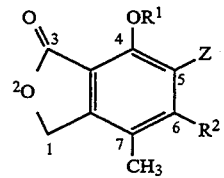

Side chains of Formula ZA are numbered as shown below:

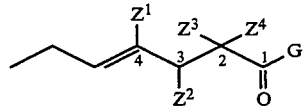

Representative compounds of Formula A where the side chain is ZA are as follows:

| # | $R^1$ | $R^2$ | $Z^1$ | $Z^2$ | $Z^3$ | $Z^4$ | G | Isomer |
|---|---|---|---|---|---|---|---|---|
| 1 | H | Methyl | Methyl | H | H | Methyl | OH | S |
| 2 | H | Cyclopropyl | Methyl | H | H | Ethyl | OH | S |
| 3 | H | Ethynyl | Cl | $CH_3$ | $SO_2CH_3$ | H | $O(CH_2)_2N=G^3$ | RS |
| 4 | C(O)Ph | $CH_2OH$ | H | $CH_3$ | $OCH_3$ | Cl | $SCH_3$ | (2) R | and are named:
1. (E)-6-(1,3-dihydro-4-hydroxy-6,7-dimethyl-3-oxoisobenzofuran-5-yl)-2-(S),4-dimethyl-4-hexenoic acid;
2. (E)-6-(6-cyclopropyl-1,3-dihydro-4-hydroxy-7-methyl-3-oxoisobenzofuran-5-yl)-2-(S)-ethyl-4-methyl-4-hexenoic acid;
3. 2-morpholinoethyl (E)-4-chloro-6-(1,3-dihydro-6-ethynyl-4-hydroxy-7-methyl-3-oxoisobenzofuran-5-yl)-3-methyl-2-methylsulfonyl-4-hexenoate (where $G^3$ is $-(CH_2)_2-O-(CH_2)_2-$);
4. thiomethyl (E)-2-(R)-chloro-6-(4-benzoyloxy-1,3-dihydro-6-hydroxymethyl-7-methyl-3-oxoisobenzofuran-5-yl)-2-methoxy-3-methyl-4-hexenoate.

Side chains of Formula ZB in which $D^1$ and $D^2$ do not contain a heteroatom are numbered as shown below:

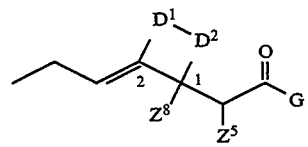

representative compounds of which are as follows:

| # | $R^1$ | $R^2$ | $D^1$-$D^2$ | $Z^5$ | $Z^8$ | G | Isomer |
|---|---|---|---|---|---|---|---|
| 1 | H | Ethyl | $(CH_2)_3$ | H | H | OH | S |
| 2 | H | 1-Fluorovinyl | $(CH_2)_4$ | H | Ethyl | OH | RS |
| 3 | $C(O)CH_3$ | Prop-2-enyl | $(CH_2)_5$ | Methyl | H | $NG^1G^2$ | RS |
| 4 | H | But-2-ynyl | $(CH_2)_2C(O)CH_2$ | H | H | OH | RS |
| 5 | H | Formyl | $(CH_2)_2$ | Hexyl | H | S-methyl | (1)-R | and are named:
1. (S)-2-{2-[2-[1,3-dihydro-6-ethyl-4-hydroxy-7-methyl-3-oxoisobenzofuran-5-yl]ethylidene]cyclopent-1-(S)-yl}acetic acid;

2. (E)-2-{2-[2-(1,3-dihydro-6-(1-fluorovinyl)-4-hydroxy-7-methyl-3-oxoisobenzofuran-5-yl)ethylidene]-1-ethylcyclohex-1-yl}acetic acid;
3. (E)-2-{2-[2-(4-acetoxy-1,3-dihydro-7-methyl-3-oxo-6-(prop-2-enyl)isobenzofuran-5-yl)ethylidene]cyclohept-1-yl}propionic acid dimethylamide (where G¹ and G² are both methyl);
4. (E)-2-{2-[2-(6-but-2-ynyl-1,3-dihydro-4-hydroxy-7-methyl-3-oxoisobenzofuran-5-yl)ethylidene]-5-oxocyclohex-1-yl}acetic acid;
5. thiomethyl (E)-2-{2-[2-(1,3-dihydro-6-formyl-4-hydroxy-7-methyl-3-oxoisobenzofuran-5-yl)ethylidene]cyclobut-1-(R)-yl}octanoate.

Side chains of Formula ZB that include a heteroatom are numbered starting with the heteroatom as position 1 of the ring, for example, as shown below for a 6-atom heterocycle.

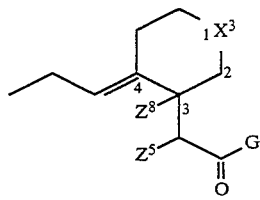

Representative compounds of Formula A where the side chain is ZB including a heteroatom are as follows:

| # | R¹ | R² | D¹-D² | Z⁵ | Z⁸ | G | Isomer |
|---|----|----|-------|----|----|---|--------|
| 1 | H | Methyl | CH₂—O—CH₂ | H | H | OH | RS |
| 2 | C(O)CH₃ | Vinyl | (CH₂)₂—NH—CH₂ | Methyl | Methyl | O-Hexyl | (3)-S |
| 3 | H | allenyl | (CH₂)₂—S—CH₂ | Hexyl | H | NG¹G² | RS | and are named:
1. (E)-2-{4-[2-(1,3-dihydro-6,7-dimethyl-4-hydroxy-3-oxoisobenzofuran-5-yl)ethylidene]tetrahydrofuran-3-yl}acetic acid;
2. hexyl (E)-2-{4-[2-(4-acetoxy-1,3-dihydro-7-methyl-3-oxo-6-vinylisobenzofuran-5-yl)ethylidene]-3-methylpiperidin-3(S)-yl}propionate;
3. (E)-2-{4-[2-(6-allenyl-1,3-dihydro-4-hydroxy-7-methyl-3-oxoisobenzofuran-5-yl)ethylidene]thiepan-3-yl}heptanoic acid dimethylamide (where G¹ and G² are both methyl).

Side chains of Formula ZC are numbered as shown below:

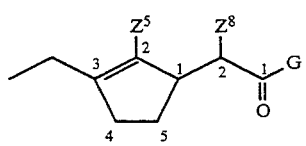

Representative compounds of Formula A where the side chain is ZC are as follows:

| # | R¹ | R² | Z⁵ | Z⁸ | G | Isomer |
|---|----|----|----|----|---|--------|
| 1 | H | i-Propyl | Methyl | H | OH | S |
| 2 | C(O)CH₃ | Trifluorovinyl | H | H | O-Hexyl | RS |
| 3 | H | 4-Methoxybenzyloxymethyl | Methyl | i-Propyl | OH | 2-S, 1-S |
| 4 | H | Ethyl | Hexyl | H | O(CH₂)₂NG¹G² | RS | and are named:
1. 3-(1,3-dihydro-4-hydroxy-6-i-propyl-7-methyl-3-oxoisobenzofuran-5-ylmethyl)-2-methylcyclopent-2-enyl-1-(S)-acetic acid;
2. hexyl 3-(4-acetoxy-1,3-dihydro-7-methyl-3-oxo-6-trifluorovinylisobenzofuran-5-ylmethyl)cyclopent-2-enyl-1-acetate;
3. 2-(S)-[3-(1,3-dihydro-4-hydroxy-6-(4-methoxybenzyloxymethyl)-7-methyl-3-oxoisobenzofuran-5-ylmethyl)-2-methyl cyclopent-2-en-1(S)-yl]-1-(S)-3-methylbutyric acid;
4. (2-dimethylamino)ethyl 3-(1,3-dihydro-6-ethyl-4-hydroxy-7-methyl-3-oxoisobenzofuran-5-ylmethyl)-2-hexylcyclopent-2-enyl-1-acetate (where G¹ and G² are both methyl).

Side chains of Formula ZD are numbered as shown below:

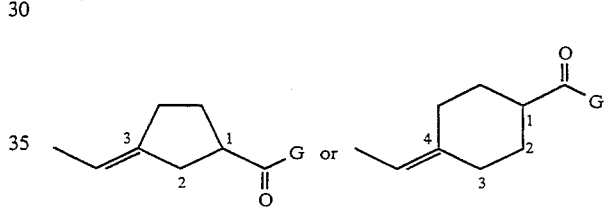

where D³ is CH₂          where D³ is CH₂CH₂

Representative compounds of Formula A where the side chain is ZD are as follows:

| # | R¹ | R² | D³ | G | Isomer |
|---|----|----|----|---|--------|
| 1 | H | Ethyl | CH₂ | OH | R |
| 2 | C(O)CH₃ | Cyclopropyl | CH₂CH₂ | O-Hexyl | RS |
| 3 | H | Vinyl | CH₂ | S-Methyl | RS | are named as follows:
1. (E)-3-[2-(1,3-dihydro-6-ethyl-4-hydroxy-7-methyl-3-oxoisobenzofuran-5-yl)ethylidene]cyclopentane-1-(R)-carboxylic acid;
2. hexyl (E)-4-[2-(4-acetoxy-6-cyclopropyl-1,3-dihydro-7-methyl-3-oxoisobenzofuran-5-yl)ethylidene]cyclohexane-1-carboxylate;
3. methyl (E)-3-[2-(1,3-dihydro-4-hydroxy-7-methyl-3-oxo-6-vinylisobenzofuran-5-yl)ethylidene]cyclopentane-1-thiocarboxylate.

Side chains of Formula ZE are numbered as shown below:

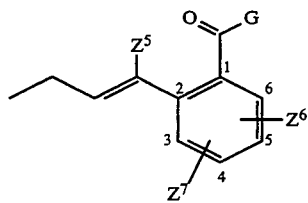

Representative compounds of Formula A where the side chain is ZE are as follows:

| # | R¹ | R² | Z⁵ | Z⁶ | Z⁷ | G |
|---|---|---|---|---|---|---|
| 1 | H | Methyl | Methyl | H | H | OH |
| 2 | C(O)CH₃ | 2,2-Difluoro-vinyl | H | 6-Methyl | H | NG¹G² |
| 3 | H | n-Butyl | Hexyl | 6-chloro | 4-methoxy | O-Hexyl | and are named:
1. (E)-2-[3-(1,3-dihydro-6,7-dimethyl-4-hydroxy-3-oxoisobenzofuran-5-yl)-1-methylprop-1-en-1-yl]benzoic acid;
2. (E)-2-[3-(4-acetoxy-1,3-dihydro-6-(2,2-difluorovinyl)-7-methyl-3-oxoisobenzofuran-5-yl)prop-1-en-1-yl]-6-methylbenzoic acid dimethylamide (where G¹ and G² are both methyl);
3. hexyl (E)-6-chloro-2-[3-(1,3-dihydro-4-hydroxy-7-methyl-6-n-butyl-3-oxoisobenzofuran-5-yl)-1-hexyl-prop-1-en-1-yl]-6-chlorobenzoate.

Side chains of Formula ZF are numbered as shown below:

![ZF structure]

Representative compounds of Formula A where the side chain is ZF are as follows:

| # | R¹ | R² | Z¹ | G | Isomer |
|---|---|---|---|---|---|
| 1 | H | Ethyl | Methyl | OH | S |
| 2 | C(O)CH₃ | Vinyl | Hexyl | O-Ethyl | RS |
| 3 | H | Ethynyl | H | S-Methyl | RS | and are named:
1. 4-(1,3-dihydro-6-ethyl-4-hydroxy-7-methyl-3-oxoisobenzofuran-5-ylmethyl)-3-methylcyclopent-3-ene-1-(S)-carboxylic acid;
2. ethyl 4-(4-acetoxy-1,3-dihydro-7-methyl-3-oxo-6-vinylisobenzofuran-5-ylmethyl)-3-hexylcyclopent-3-ene-1-carboxylate;
3. thiomethyl 4-(1,3-dihydro-6-ethynyl-4-hydroxy-7-methyl-3-oxoisobenzofuran-5-ylmethyl)cyclopent-3-ene-1-carboxylate.

Side chains of Formula ZG are numbered as shown below:

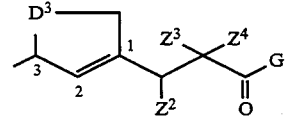

Representative compounds of Formula A where the side chain is ZG are as follows:

| # | R¹ | R² | D³ | Z² | Z³ | Z⁴ | G | Isomer |
|---|---|---|---|---|---|---|---|---|
| 1 | H | Methyl | CH₂ | H | H | H | OH | (3)-S |
| 2 | H | Ethyl | CH₂ | H | Methyl | Chloro | Methoxy | (3)-R |
| 3 | C(O)C₂H₅ | Cyclopentyl | CH₂ | Methyl | H | Phenyl | OH | RS |
| 4 | H | Vinyl | CH₂ | H | H | H | S-Methyl | (3)-R |
| 5 | C(O)Ph | Formyl | (CH₂)₂ | Methyl | O-Methyl | Methyl | OH | (2)-R | and are named:
1. 3-[3-(S)-(1,3-dihydro-6,7-dimethyl-4-hydroxy-3-oxoisobenzo-furan-5-yl)cyclopent-1-en-1-yl]-propionic acid;
2. methyl 3-[3-(R)-(1,3-dihydro-6-ethyl-4-hydroxy-7-methyl-3-oxoisobenzofuran-5-yl)cyclopent-1-en-1-yl]-2-chloro-2-methyl propionate;
3. 3-[3-(6-cyclopentyl-1,3-dihydro-7-methyl-3-oxo-4-propionyloxyisobenzo-furan-5-yl)cyclopent-1-en-1-yl]-3-methyl-2-phenyl propionic acid;
4. methyl 3-[3-(R)-(1,3-dihydro-4-hydroxy-7-methyl-3-oxo-6-vinylisobenzofuran-5-yl)cyclopent-1-en-1-yl]propionate;
5. 3-[3-(4-benzoyloxy-1,3-dihydro-6-formyl-7-methyl-3-oxoisobenzofuran-5-yl)cyclohex-1-en-1-yl]-2(R),3-dimethyl-2-methoxy propionic acid.

Side chains of Formula ZH are numbered as shown below:

![ZH structure]

Representative compounds of Formula A where the side chain is ZH are as follows:

| # | R² | D⁴ | Z¹ | G | Isomer |
|---|---|---|---|---|---|
| 1 | Methyl | CH₂ | Methyl | OH | RS |
| 2 | Ethyl | (CH₂)₂ | Methyl | O-Ethyl | 1-R |

| # | R² | D⁴ | Z¹ | G | Isomer |
|---|------|--------|----|----------|------|
| 3 | Vinyl | (CH₂)₃ | H | S-Methyl | RS | are named as follows:

1. (E)-2-[3-(1,3-dihydro-6,7-dimethyl-4-hydroxy-3-oxoisobenzofuran-5-yl)-1-methylprop-1-en-1-yl]cyclopentane-1-carboxylic acid;
2. Ethyl (E)-2-[3-(1,3-dihydro-6-ethyl-4-hydroxy-7-methyl-3-oxoisobenzofuran-5-yl)-1-methylprop-1-en-1-yl]cyclohexane-1R -carboxylate;
3. Thiomethyl (E)-2-[3-(1,3-dihydro-4-hydroxy-7-methyl-3-oxo-6-vinylisobenzofuran-5-yl)prop-1-en-1-yl]cycloheptane-1-carboxylate.

Compounds of Formula A where the side chain is ZH, in which D⁴ is a heteroatom, are numbered differently. For example, the compound where R² is ethyl, D⁴ is oxygen, Z¹ is methyl, and G is hydroxy, is named as follows:

4. (E)-2-[3-(1,3-dihydro-6-ethyl-4-hydroxy-7-methyl-3-oxoisobenzofuran-5-yl)-1-methylprop-1-en-1-yl]tetrahydrofuran-3-carboxylic acid.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents. The term "q.s." means adding a quantity sufficient to achieve a stated function, e.g., to bring a solution to a desired volume (for example, q.s. to 100%).

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used. Except as specified to the contrary, the compounds and intermediates are isolated and purified by conventional means.

As indicated above, compounds that have one asymmetric center can exist as R or S enantiomers or as mixtures thereof. If desired, the individual R and S enantiomers can be separated by known methods, or can be synthesized individually.

For example, an acidic racemic compound can be converted into a salt, ester or amide with a chiral base, alcohol or amine. The resulting mixture of diastereomers can be separated by conventional means such as crystallization, distillation or chromatography. The separated compounds can then be subjected to conventional reactions such as hydrolysis, to produce the individual enantiomers of the chiral acid. A chiral compound which is basic can be resolved analogously.

Alternatively, a chiral compound can be separated into enantiomers by selective reaction of one of the enantiomers, or of a derivative. For example, an ester or amide of a racemic compound can be selectively hydrolyzed by chemical or biological (e.g., enzymatic) reactions to produce the individual enantiomers of the racemic compound.

Compounds that have two asymmetric centers exist as two diastereomers. The diastereomers can be separated by conventional methods such as crystallization, distillation or chromatography. Each separate diastereomer exists as a pair of enantiomers which can be separated by conventional methods such as those described above. Alternatively, the diastereomers or enantiomers can be prepared separately, by means of stereospecific or diastereoselective reactions known to those skilled in the art.

Alternatively, chiral precursors to chiral compounds of this invention can be prepared using known procedures such as stereoselective or stereospecific reactions, after which the chiral precursor can be converted into the chiral product.

Synthesis of the Compounds of Formula A

The compounds of Formula A are synthesized starting from the precursors of Formula I:

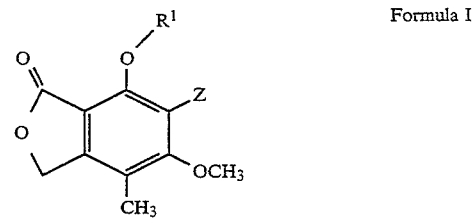

Formula I where R¹ is hydrogen and Z has the meanings set forth in the Summary of the Invention, where G is OH or lower alkoxy [designated as the group —Zᵃ—OH or —Zᵃ—lower alkyl in Reaction Schemes A and B, which follow Reaction Schemes ZA-A-1 through ZH-B (in other words, Zᵃ is any side chain of Formulae ZA, ZB, ZC, ZD, ZE, ZF, ZG or ZH without the substituent designated as G)].

The compounds of Formula I are prepared as illustrated with reference to Reaction Schemes ZA-A-1 through ZH-B below, the preparations of which are exemplified in copending application Ser. No. 08/198,749, Attorney Docket No. 27960, entitled "5-Substituted Derivatives Of Mycophenolic Acid," previously incorporated by reference.

As those skilled in the art will appreciate, the intermediates synthesized in the preparation of compounds of Formula I, e.g., where Rᵃ is tosyl and/or where G is lower alkoxy can be substituted in Reaction Scheme A for the compounds of Formula IA and 2 without need for conversion through corresponding compounds where $R^a$ is H and G is OH. For example, the compounds of Formula 105 where $R^a$ is aryl or alkylsulfonyl can be used directly as compound of Formula 2 in Reaction Scheme A.

Alternatively, when $R^2$ is lower alkyl or cycloalkyl, by using mycophenolic acid as the starting material and performing the syntheses described with reference to Reaction Schemes A and B, the correspondingly obtained 6-substituted derivatives can be further derivatized at the 4-and/or 5-position(s), e.g., as described with reference to Reaction Schemes ZA-A through ZH-B.

As used in the Reaction Schemes, the substituents (e.g., m, $D^1$, G, $Z^1$) have the same meaning as described in the Summary of the Invention unless otherwise specified in a particular instance. Substituents introduced for purposes of a particular reaction scheme (e.g., $R^a$ in Reaction Scheme ZA-A) are defined in the detailed description of the corresponding synthesis.

Starting Materials

Mycophenolic acid is commercially available, e.g., from Sigma Chemical Company, St. Louis, Mo. The mycophenolic acid lower alkyl esters of Formula 1 can be synthesized, for example, as described in *Synthetic Organic Chemistry* by Wagner and Zook (Wiley, New York) 1956, see pages 479–532. Other reactants, such as methoxyethoxy methyl chloride, t-butyldimethylsilyl chloride, and various orthoesters are likewise commercially available or may be readily prepared by those skilled in the art using commonly employed synthetic methodology.

Preparation of Compounds of Formula I-ZA

One method of preparing compounds of Formula I where Z is sidechain of Formula ZA, illustrated as compounds of Formula I-ZA, is shown below in Reaction Schemes ZA-A to ZA-M.

REACTION SCHEME ZA-A

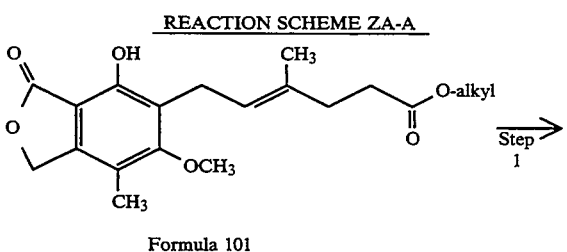

Formula 101

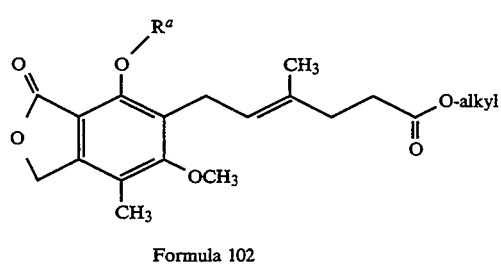

Formula 102

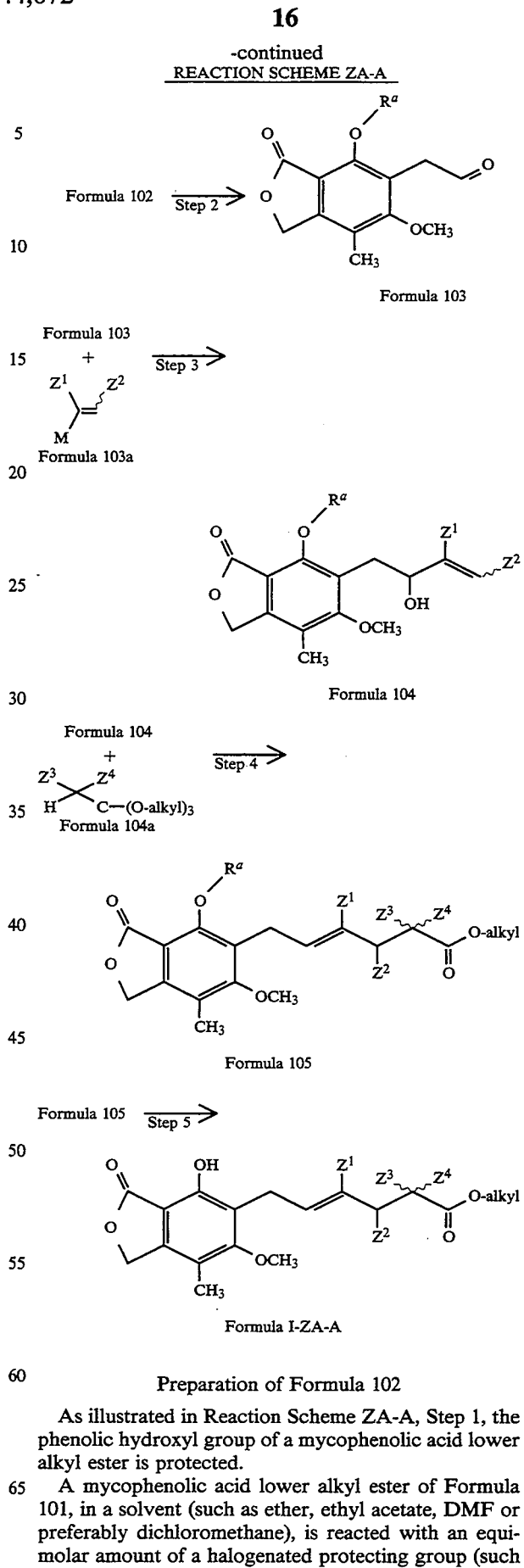

Preparation of Formula 102

As illustrated in Reaction Scheme ZA-A, Step 1, the phenolic hydroxyl group of a mycophenolic acid lower alkyl ester is protected.

A mycophenolic acid lower alkyl ester of Formula 101, in a solvent (such as ether, ethyl acetate, DMF or preferably dichloromethane), is reacted with an equimolar amount of a halogenated protecting group (such as: methoxyethoxymethyl chloride; a sulfonyl chloride, e.g., tosyl chloride, mesyl chloride; or a silyl chloride, e.g., trimethylsilyl chloride, diphenylmethylsilyl chloride, or preferably tert-butyldimethylsilyl chloride) in presence of an equimolar amount of an organic base (such as diisopropylethylamine, triethylamine or imidazole). The reaction takes place at −20° to 35° C. (preferably at 25° C.) for 1 to 24 hours (preferably 16 hours) to give the corresponding compound of Formula 102 (where $R^a$ is the protecting group).

Preparation of Formula 103

As illustrated in Reaction Scheme ZA-A, Step 2, the side chain double bond of a protected mycophenolic acid lower alkyl ester is ozonized to yield an aldehyde.

A stream of ozonized oxygen is passed through a solution of a protected compound of Formula 102 in a solvent (such as an alcohol, a halocarbon, or preferably a mixture of methanol and dichloromethane). The reaction takes place at −100° to −40° C. (preferably at −80° C.), and continues until the presence of excess ozone is detected by the development of a blue color, indicating the formation of an intermediate α-alkoxyhydroperoxide, which is reduced without further purification, by the addition of a reducing agent (such as zinc and acetic acid, dimethyl sulfide, or preferably thiourea). The reaction takes place at −80° C. to 25° C. (preferably 0° C.) over a period of 12 to 24 hours (preferably 16 hours), to give the corresponding aldehyde of Formula 103.

Preparation of Formula 104

As illustrated in Reaction Scheme ZA-A, Step 3, the aldehyde is converted to a carbinol by addition of an organometallic compound of Formula 103a [where M is MgBr or lithium, preferably MgBr (a Grignard reagent); $Z^1$ is H, lower alkyl or $CF_3$, and $Z^2$ is H or lower alkyl].

An organolithium reagent is formed by reaction of a halovinyl (preferably bromovinyl) compound of Formula 103a (where M is halo) with an alkyllithium (preferably n-butyllithium) in an ethereal solvent (such as ether, or preferably tetrahydrofuran). The reaction takes place at −100° to 0° C. (preferably −40° C.) over a period of 0.5 to 5 hours (preferably 1 hour).

Alternatively the halovinyl compound of Formula 103a is reacted with magnesium metal in an ethereal solvent (such as ether or preferably tetrahydrofuran). The reaction takes place at 30° to 60° C. (preferably 40° C.) over a period of 1 to 6 hours (preferably 2 hours).

The organometallic compound of Formula 103a where M is zinc or cadmium may be prepared by reaction of 103a where M is Li or MgBr with a zinc or cadmium halide, preferably chloride. The compound of Formula 103a where M is tin may be prepared by reaction of 103a where M is Li or MgBr with a trialkyl chlorostannane, preferably tributyltin chloride. The compound of Formula 103a where M is tin may also be prepared by reaction of 103a where M is trifluoromethanesulfonate by reaction with a compound of formula $(R_3Sn)_2$, where R is alkyl, preferably methyl, in the presence of a palladium catalyst, preferably tetrakis(triphenylphosphine)palladium. The compound of Formula 103a where M is trifluoromethanesulfonate may be prepared from a ketone of the formula:

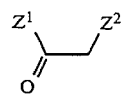

by reaction with a strong base (such as sodium hydride or potassium hexamethyldisilazide), followed by reaction of the anion thus produced with trifluoromethanesulfonic anhydride. Alternatively, the compound of Formula 103a where M is tin may be prepared by reacting a trialkyl tin hydride (preferably tributyl tin hydride) with an acetylene of the formula $Z^1—C≡C—Z^2$.

One molar equivalent of the resultant organometallic reagent is added to a solution of an aldehyde of Formula 103 (in the same solvent system used to make the organometallic reagent). The reaction takes place at −80° to 20° C. (preferably 0° C.) over a period of 5 to 60 minutes (preferably 10 minutes) to give the corresponding carbinol of Formula 104.

Preparation of Formula 105

As illustrated in Reaction Scheme ZA-A, Step 4, an alkyl ester of Formula 105 is formed by a Claisen ortho ester rearrangement reaction of a carbinol of Formula 104 and an orthoester of Formula 104a (where $Z^3$ is H, halo, lower alkyl, lower alkenyl, phenyl, alkoxy or -thio lower alkyl; and $Z^4$ is H or lower alkyl; or $Z^3$ and $Z^4$ taken together with the carbon to which they are attached form cycloalkyl).

A carbinol of Formula 104 is heated at 50° to 140° C. (preferably about 130° C.) with about 10 molar equivalents of an orthoester of Formula 104a, in the presence of from 0.05 to 0.25 molar equivalents (preferably 0.10 molar equivalents) of an organic acid catalyst (such as propionic, butyric, or preferably trimethylacetic acid). The reaction takes place over a period of 1 to 48 hours (preferably 3 hours) to give the corresponding alkyl ester of Formula 105.

Preparation of Formula I-ZA-A

Formula I-ZA-A is prepared as described below with reference to Reaction Scheme ZA-M, Step 1 (in which the compound of Formula I-ZA-A is named Formula I-ZA-M1). The compounds of Formula I-ZA-A are also employed as starting materials in Step 1 of Reaction Scheme ZA-K.

Preparation of Enantiomers of Formula I-ZA where $Z^2$ is Lower Alkyl

One method of preparing individual enantiomers of compounds of Formula I where Z is sidechain ZA, illustrated as compounds of Formula I-ZA, is from chiral compounds of Formula 104b, the preparation of which is shown below in Reaction Scheme ZA-A-1.

REACTION SCHEME ZA-A-1

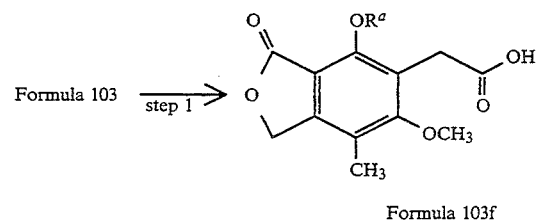

Formula 103f

-continued
REACTION SCHEME ZA-A-1

Formula 103f $\xrightarrow{\text{step 2}}$

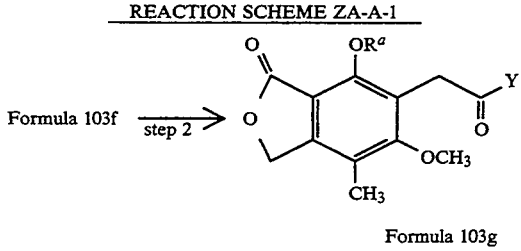

Formula 103g where Y is chloro or bromo.

Formula 103g
+ $\xrightarrow{\text{step 3}}$
Formula 103a

Formula 103h $\xrightarrow{\text{step 4}}$

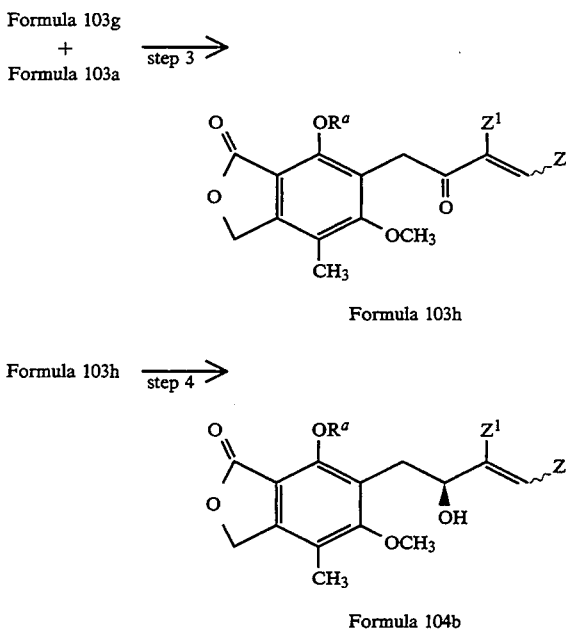

Preparation of Formula 103f

As illustrated in Reaction Scheme ZA-A-1, Step 1, an aldehyde of Formula 103 is oxidized to the corresponding carboxylic acid of Formula 103f.

An aldehyde of Formula 103 is reacted with about two molar equivalents of an oxidizing agent (for example, chromic acid, silver oxide, bleach, or preferably sodium periodate), in an inert solvent (such as toluene, or preferably ethyl acetate), in the presence of water [and, when using sodium periodate or bleach as the oxidizing agent, a catalytic amount (for example, about 0.01 molar equivalents) of ruthenium oxide, or preferably ruthenium trichloride]. The reaction takes place at 0° to 40° C. (preferably 25° C.) for 30 minutes to 8 hours (preferably 2 hours), to give the corresponding carboxylic acid of Formula 103f.

Preparation of Formula 103g

As illustrated in Reaction Scheme ZA-A-1, Step 2, a carboxylic acid of Formula 103f is converted to the corresponding acyl halide of Formula 103g.

A carboxylic acid of Formula 103f is reacted with about one molar equivalent, preferably 1.1 molar equivalents, of a thionyl or oxalyl halide (for example, thionyl chloride, thionyl bromide, or preferably oxalyl chloride), in an inert solvent (such as dichloromethane, or preferably ethyl acetate), in the presence of a catalytic amount (for example, about 0.05 molar equivalents) of dimethylformamide. The reaction takes place at 0° to 40° C. (preferably 25° C.) for 30 minutes to 8 hours (preferably 2 hours), to give the corresponding acyl halide of Formula 103g.

Preparation of Formula 103h

As illustrated in Reaction Scheme ZA-A-1, Step 3, an acyl halide of Formula 103g is converted to the corresponding keto olefin of Formula 103h by addition of an organometallic compound of Formula 103a.

An acyl halide of Formula 103g is reacted with about one molar equivalent of a organometallic compound of Formula 103a (where M is cadmium, zinc, tin, or the like, prepared as shown in the preparation of compounds of Formula 104), in an inert solvent (such as dichloromethane, ether or preferably tetrahydrofuran), optionally in the presence of a catalytic amount (for example, about 0.05 molar equivalents) of a palladium catalyst [preferably tetrakis(triphenylphosphine)palladium]. The reaction takes place at −10° to 20° C. (preferably 0° C.) for 30 minutes to 8 hours (preferably 4 hours), to give the corresponding keto olefin of Formula 103h.

Preparation of Formula 104b

As illustrated in Reaction Scheme ZA-A-1, Step 4, a keto olefin of Formula 103h is reduced stereospecifically to the corresponding carbinol of Formula 104b by reduction with borane methyl sulfide in the presence of a catalytic amount of (R)-tetrahydro-1-methyl-3,3-diphenyl-1H,3H-pyrrolo-[1,2-c][1,3,2]oxazaborole.

A keto olefin of Formula 103h is stereospecifically reduced with about one molar equivalent of borane methyl sulfide in the presence of a catalytic amount (0.05–0.3 molar equivalents) of (R)-tetrahydro-1-methyl-3,3-diphenyl-1H,3H-pyrrolo-[1,2-c][1,3,2]oxazaborole in an inert solvent (preferably a mixture of toluene and dichloromethane). The reaction takes place at −30° to 40° C. (preferably −20° C.) for 1–24 hours (preferably 12 hours), to give the corresponding carbinol of Formula 104b.

Preparation of Enantiomers of Compounds of Formula I-ZA

The chiral carbinol of Formula 104b is then converted to an enantiomer of a compound of Formula I-ZA in the same manner as shown above in Reaction Scheme ZA-A (conversion of compounds of Formula 104 to 105 to I-ZA).

REACTION SCHEME ZA-B

Formula 103
+
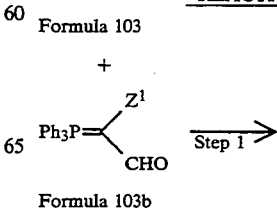 $\xrightarrow{\text{Step 1}}$

Formula 103b

-continued
REACTION SCHEME ZA-B

Formula 106

Formula 106
+
Formula 106a

Formula 107

Preparation of Formula 106

As illustrated in Reaction Scheme ZA-B, Step 1, an aldehyde of Formula 103 is transformed into an unsaturated aldehyde of Formula 106 by a Wittig reaction with an ylid of Formula 103b (where $Z^1$ is H or lower alkyl).

An aldehyde of Formula 103 is reacted with one molar equivalent of an ylid of Formula 103b, in an organic solvent (such as dichloromethane, dimethylformamide or preferably toluene). The reaction takes place at 0° to 110° C. (preferably 80° C.) for 1 to 24 hours (preferably 8 hours) to give the corresponding unsaturated aldehyde of Formula 106.

Preparation of Formula 107

As illustrated in Reaction Scheme ZA-B, Step 2, an unsaturated aldehyde of Formula 106 is condensed with the anion of an ester of Formula 106a (where $Z^3$ is H, lower alkyl, lower alkenyl, or phenyl and $Z^4$ is H, lower alkyl, or phenyl) to give a beta-hydroxy ester of Formula 107.

An ester of Formula 106a is converted to an alkali metal salt by reacting a solution of the ester in an ethereal solvent (such as ether or preferably tetrahydrofuran) with an equimolar amount of an alkali metal hydride, hexamethyldisilazide or amide (preferably lithium diisopropylamide) at a temperature of $-100°$ to $0°$ C. (preferably $-80°$ C.), for 30 minutes to 2 hours (preferably 30 minutes) to give a solution of the corresponding ester anion. The ester anion solution (1.0 to 1.5 molar equivalents, preferably 1.0 molar equivalents) is added to a solution of an unsaturated aldehyde of Formula 106 in the same ethereal solvent. The condensation reaction takes place at a temperature of $-100°$ C. to $0°$ C. (preferably $-80°$ C.) for 1 to 6 hours (preferably 2 hours) to give the corresponding beta-hydroxy ester of Formula 107.

REACTION SCHEME ZA-C

Formula 107 $\xrightarrow{\text{Step 1}}$

Formula 108

Preparation of Formula 108

As illustrated in Reaction Scheme ZA-C, Step 1, the beta-hydroxy group of an ester of Formula 107 is O-alkylated to give the corresponding beta-alkoxy ester ($R^b$) of Formula 108.

An ester of Formula 107 is reacted with 1 to 3 (preferably 1.5) molar equivalents of an alkyl halide (preferably an alkyl iodide, such as methyl iodide or n-butyl iodide, preferably methyl iodide) and 1 to 3 (preferably 1.25) molar equivalents of silver oxide, in a polar organic solvent (such as dioxane, dimethylformamide or preferably acetonitrile). The reaction takes place at 25° to 100° C. (preferably 70° C.) for 1 to 24 hours (preferably hours) to give the corresponding beta-alkoxy ester of Formula 108.

REACTION SCHEME ZA-E

Formula 106 $\xrightarrow{\text{Step 1}}$

Formula 109

Formula 109
+

Formula 109a

-continued
REACTION SCHEME ZA-E

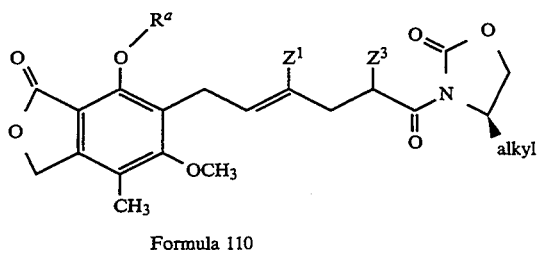

Formula 110

Formula 110 $\xrightarrow{\text{Step 3}}$

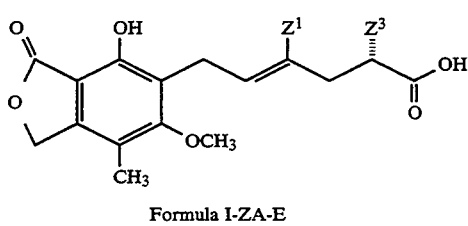

Formula I-ZA-E

Preparation of Formula 109

As illustrated in Reaction Scheme ZA-E, Step 1, an unsaturated aldehyde of Formula 106 is reduced and then converted to the corresponding compound of Formula 109 in which $R^b$ is a leaving group (a sulfonate or halide, preferably a bromide).

An unsaturated aldehyde of Formula 106 is reacted with from 0.5 to 2 (preferably 1) molar equivalents of a reducing agent (such as sodium cyanoborohydride or preferably sodium borohydride) in an alcoholic solvent (such as ethanol, isopropanol or preferably methanol). The reaction takes place at 0° to 50° C. (preferably 25° C.) for 1 to 12 hours (preferably 2 hours) to give the corresponding allylic alcohol (not shown) which is used without isolation or further purification.

The allylic alcohol is reacted with from 1 to 1.5 (preferably 1.25) molar equivalents of a sulfonating agent (such as p-toluenesulfonyl chloride) and an organic base, or preferably reacted with a halogenating reagent (such as carbon tetrachloride/triphenylphosphine or preferably N-bromosuccinimide/triphenylphosphine) in an inert organic solvent (such as ether or preferably dichloromethane). The reaction takes place at a temperature of −40° to 40° C. (preferably −10° C.) for 1 to 12 hours (preferably 2 hours) to afford the corresponding compound of Formula 109.

Preparation of Formula 110

An allylic halide or sulfonate of Formula 109 is alkylated with a chiral 4-alkyl N-acyl oxazolidinone of Formula 109a to give the corresponding chiral substituted acyl oxazolidinone of Formula 110.

An alkali metal (preferably lithium) salt of a chiral 4-alkyl N-acyl oxazolidinone of Formula 109a (the alkyl group preferably being 4-isopropyl) by reaction of the N-acyl oxazolidinone with 1 to 1.25 (preferably 1.05) molar equivalents of an alkali metal hydride, hexamethyldisilazide or dialkylamide (preferably lithium diisopropylamide) in an inert organic solvent (such as ether or preferably tetrahydrofuran). The reaction takes place at −100° to −20° C. (preferably −80° C.) for 5 to 120 minutes (preferably 30 minutes). The solution of the allylic compound of Formula 109 in the same solvent is added to the salt (1 to 3, preferably 3 molar equivalents). The alkylation reaction takes place at −100° to 0° C. (preferably −10° C.) for 30 minutes to 6 hours (preferably 1 hour) to afford the corresponding chiral substituted acyl oxazolidinone of Formula 110.

Preparation of Formula I-ZA-E

As illustrated in Reaction Scheme ZA-E, Step 3, a chiral substituted acyl oxazolidinone of Formula 110 is hydrolyzed to the corresponding chiral acid of Formula I-ZA-E. Use of an acyl oxazolidinone of Formula 109a having a 4-alkyl substituent of the opposite configuration in Reaction Scheme ZA-E, Step 2, followed by hydrolysis as described in Step 3 results in the corresponding chiral acid where $Z^3$ has the opposite configuration.

An acyl oxazolidinone of Formula 110 is reacted with from 1.25 to 3.5 (preferably 3.0) molar equivalents of lithium hydroxide, in a mixture of water and a water-miscible organic solvent (such as dioxane or preferably tetrahydrofuran) containing from 6 to 10 (preferably 8) molar equivalents of 30% aqueous hydrogen peroxide. The reaction takes place at −20° to 40° C. (preferably 20° C.) for 1 to 24 hours (preferably 12 hours) to afford the corresponding chiral acid of Formula I-ZA-E.

REACTION SCHEME ZA-H

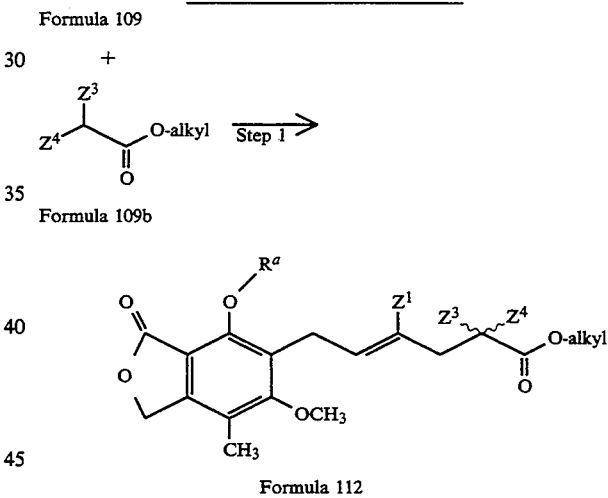

Preparation of Formula 112

As illustrated in Reaction Scheme ZA-H, Step 1, an allylic compound of Formula 109 in which $R^b$ is a leaving group (a sulfonate or halide, preferably a bromide) is condensed with an ester of Formula 109b to give the mono- or di-alkyl ester of Formula 112 (where $Z^3$ is H, lower alkyl, lower alkenyl, or phenyl and $Z^4$ is H, lower alkyl, or phenyl).

An ester of Formula 109b is converted to an alkali metal salt by reaction with 1.05 to 1.25 (preferably 1.1) molar equivalents of an alkali metal amide (such as sodium hexamethyldisilazide, potassium tetramethylpiperidide or preferably lithium diisopropylamide) in an organic solvent (such as ether, dioxane or preferably tetrahydrofuran). The reaction takes place at −40° to 30° C. (preferably 0° C.) for 15 minutes to 3 hours (preferably 30 minutes). Without isolation or further purification, the resulting solution of the alkali metal salt of the ester of Formula 109b (1.2 to 1.6, preferably about 1.3 molar equivalents) is then reacted with an allylic compound of Formula 109, in the same solvent, optionally in the presence of from 2% to 10% (preferably about 5%) by volume of hexamethyl phosphoric triamide. The reaction takes place at $-100°$ to $-40°$ C. (preferably $-80°$ C.) for 30 minutes to 6 hours (preferably 1 hour) to afford the corresponding alkyl ester of Formula 112.

REACTION SCHEME ZA-K

Formula I-ZA-A $\xrightarrow{\text{Step 1}}$

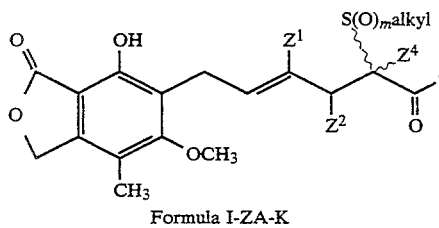

Formula I-ZA-K

Preparation of Formula I-ZA-K

As illustrated in Reaction Scheme ZA-K, Step 1, a 2-(alkylthio)-4-hexenoic acid ester of Formula I-ZA-A (where $Z^3$ is S-lower alkyl, and $Z^4$ is H or lower alkyl) is oxidized to give the corresponding 2-(alkylsulfinyl)- or 2-(alkylsulfonyl)-4-hexenoic acid ester of Formula I-ZA-K (where m is 1 or 2). Alternatively, the reaction can be performed with an acid of Formula I-ZA-M2 where $Z^3$ is S-lower alkyl, to give the corresponding acid where $Z^3$ is 2-(alkylsulfinyl) or 2-(alkylsulfonyl).

An alkylthio-4-hexenoic acid ester of Formula I-ZA-A is reacted with 1.0 to 1.25 (preferably 1.05) molar equivalents of an oxidizing agent (such as Oxone®) optionally in the presence of an inert support (such as alumina), in a solvent (such as chloroform or preferably dichloromethane). The reaction takes place at 0° to 55° C. (preferably 35° C.) for 1 to 10 hours (preferably 2 hours) to afford the corresponding 2-(alkylsulfinyl)-4-hexenoic acid ester of Formula I-ZA-K (where m is 1).

By repeating the foregoing procedure under the same conditions [starting with the 2-(alkylsulfinyl)-4-hexenoic acid ester so-produced], or by conducting the reaction with the 2-(alkylthio)-4-hexenoic acid ester starting material [and using 2.0 to 2.5 (preferably 2.25) molar equivalents of oxone] the corresponding 2-alkylsulfonyl-4-hexenoic acid esters are produced.

A 2-(alkylsulfinyl)- or 2-(alkylsulfonyl)-4-hexenoic acid ester of Formula I-ZA-K is hydrolyzed to give the corresponding acid as described with reference to Reaction Scheme ZA-M, Step 2. Alternatively, the acid can be obtained by substituting the corresponding 2-(alkylthio)-4-hexenoic acid for the ester starting material as described in Reaction Scheme ZA-K, Step 1.

REACTION SCHEME ZA-L

Formula 103
+
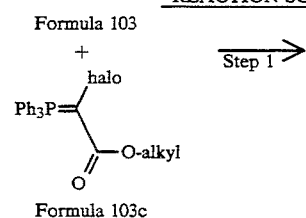

Formula 103c

-continued
REACTION SCHEME ZA-L

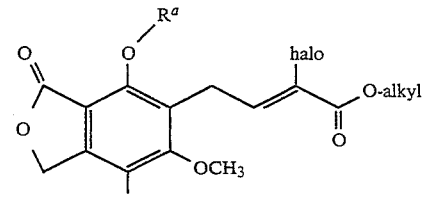

Formula 114

Formula 114 $\xrightarrow{\text{Step 2}}$

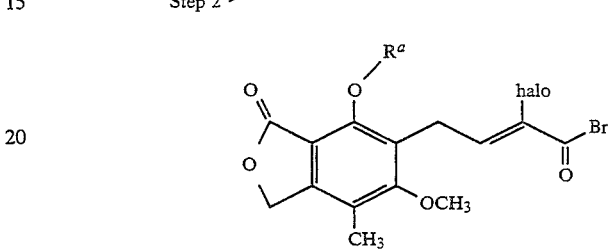

Formula 115

Formula 115
+
$Z^4CH(CO_2Et)_2$ $\xrightarrow{\text{Step 3}}$
Formula 116

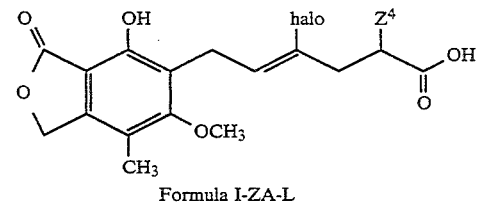

Formula I-ZA-L

Preparation of Formula 114

As illustrated in Reaction Scheme ZA-L, Step 1, a protected aldehyde of Formula 103 and a triphenylphosphoranylideneacetate of Formula 103c are combined in a Wittig reaction to give the corresponding alkyl-2-halobutenoate ester of Formula 114.

An aldehyde of Formula 103 is reacted with 1.0 to 1.5 (preferably 1.1) molar equivalents of an alkyl 2-halo-2-triphenylphosphoranylideneacetate of Formula 103c (the halo group preferably being chloro) in an organic solvent (such as acetonitrile, or preferably dimethylformamide or toluene). The reaction takes place at 0° to 120° C. (preferably 110° C.) for 4 to 48 hours (preferably 24 hours) to afford the corresponding alkyl 2-halo-4-aryl-2-butenoate ester of Formula 114.

Preparation of Formula 115

As illustrated in Reaction Scheme ZA-L, Step 2, a protected alkyl 2-halo-4-aryl-2-butenoate ester of Formula 114 is converted to the corresponding bromide of Formula 115 via conversion to the corresponding acid (not shown) and reduction to the corresponding alcohol (not shown).

A 2-halo-4-aryl-2-butenoate ester of Formula 114 (preferably a t-butyl ester) is converted to the corresponding acid (preferably by dissolution in trifluoroacetic acid at room temperature for 1 to 2 hours). The acid is isolated and purified by conventional means, then reacted with 0.5 to 3 (preferably 1.6) molar equivalents of a reducing agent (such as sodium cyanoborohydride, sodium borohydride, or preferably borane dimethyl disulfide complex) in a solvent (such as methanol, ethanol, isopropanol or preferably THF). The reaction takes place at 0° to 50° C. (preferably 25° C.) for 1 to 48 hours (preferably 24 hours) to give the corresponding alcohol (not shown) which is used after purification.

The allylic alcohol so-produced is reacted with from 1 to 1.5 (preferably 1.25) molar equivalents of a sulfonating agent (such as p-toluenesulfonyl chloride) and an organic base, or preferably reacted with a halogenating reagent (such as carbon tetrachloride/triphenylphosphine or preferably N-bromosuccinimide/triphenylphosphine) in an inert organic solvent (such as ether or preferably dichloromethane). The reaction takes place at a temperature of −40° to 40° C. (preferably −10° C.) for 1 to 12 hours (preferably 2 hours) to afford the corresponding 2-halo-4-aryl-2-butenyl bromide compound of Formula 115.

Preparation of Formula I-ZA-L

As illustrated in Reaction Scheme ZA-L, Step 3, a protected 2-halo-4aryl-2-butenyl bromide compound of Formula 115 is condensed with a dialkyl malonate of Formula 116, substituted by $Z^4$ (where $Z^4$ is hydrogen, lower alkyl, or phenyl), which is hydrolyzsed and decarboxylated to give the corresponding 4-halo-4-hexenoic acid derivative of Formula I-ZA-L.

An ester of Formula 116 (where $Z^4$ is H, lower alkyl, or phenyl) is converted to an alkali metal salt by reaction with 1.05 to 1.25 (preferably 1.1) molar equivalents of an alkali metal hydride (preferably sodium hydride) in an organic solvent (such as ether, dioxane or preferably tetrahydrofuran). The reaction takes place at −40° to 30° C. (preferably 0° C.) for 15 minutes to 3 hours (preferably 30 minutes). Without isolation or further purification, the resulting solution of the alkali metal salt of the ester of Formula 116 (1.2 to 1.6, preferably about 1.3 molar equivalents) is then reacted with an allylic bromo compound of Formula 115 in the same solvent. The reaction takes place at −20° to 50° C. (preferably 25° C.) for 30 minutes to 6 hours (preferably 2 hours) to afford the corresponding dialkyl ester derivative.

The dialkyl ester thus produced is then hydrolyzsed conventionally, using a strong base, preferably aqueous sodium hydroxide, in a protic solvent, preferably ethanol, heating to reflux. The dicarboxylic acid thus produced is separated conventionally, and then decarboxylated by heating, preferably in a high-boiling inert solvent, most preferably 1,2-dichlorobenzene, to give the corresponding 4-halo-4-hexenoic acid derivative of Formula I-ZA-L.

REACTION SCHEME ZA-M

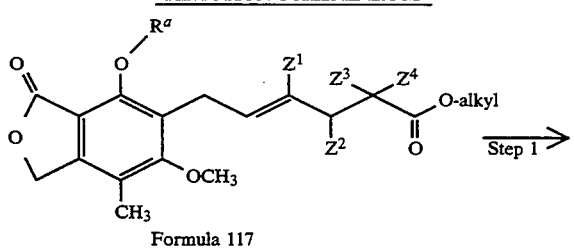

Formula 117

-continued
REACTION SCHEME ZA-M

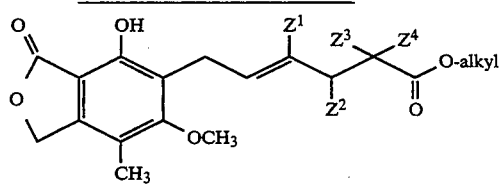

Formula I-ZA-M1

Formula I-ZA-M1 $\xrightarrow{\text{Step 2}}$

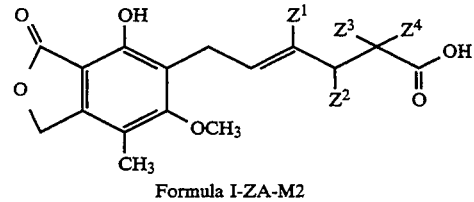

Formula I-ZA-M2

Preparation of Formula I-ZA-M1

As illustrated in Reaction Scheme ZA-M, Step 1, an alkyl ester of Formula 117 (which can be any of the corresponding protected esters of Reaction Schemes ZA-A to ZA-L, such as Formulae 105, 107, 108, and 112) is deprotected to give the corresponding alkyl ester of Formula I-ZA-M1.

An alkyl ester of Formula 117 (having either an acetal-type or a silyl-type protecting group) is treated with from 0.05 to 0.2 molar equivalents (preferably 0.1 molar equivalents) of an aqueous mineral acid (such as sulfuric, perchloric, or preferably hydrochloric acid), in a water-miscible organic solvent (such as methanol, acetone, or preferably ethanol). The reaction takes place at 0° to 50° C. (preferably 25° C.) over a period of 1 to 6 hours (preferably 2 hours) to give the corresponding free phenol of Formula I-ZA-M1.

Alternatively, to remove acetal-type protecting groups (such as MEM) a compound of Formula 117 is treated with 0.05 to 0.25 molar equivalents (preferably 0.1 molar equivalents) of a Lewis acid (such as zinc chloride or preferably zinc bromide), in a solvent (such as benzene, chloroform, or preferably dichloromethane). The reaction takes place at 0° to 50° C. (preferably 25° C.) over a period of 1 to 12 hours (preferably 3 hours) to give the corresponding free phenol of Formula I-ZA-M1.

Alternatively, to remove silyl-type protecting groups (such as t-butyldimethylsilyl) a compound of Formula 117 is reacted with 1.0 to 1.5 (preferably 1.25) moles of a tetraalkyl ammonium fluoride (preferably tetrabutylammonium fluoride;) in an ethereal solvent (such as dioxane or preferably tetrahydrofuran). The reaction takes place at −10° to 25° C. (preferably 0° C.) over a period of 0.1 to 2 hours (preferably 0.5 hours) to give the corresponding free phenol of Formula I-ZA-M1.

Preparation of Formula I-ZA-M2

As illustrated in Reaction Scheme ZA-M, Step 2, an alkyl ester of Formula I-ZA-M1 (prepared as described above, or which can be any of previously described deprotected esters, such as Formulae I-ZA-A, I-ZA-G, I-ZA-I, I-ZA-J, and I-ZA-K) is hydrolyzed to give the corresponding acid of Formula I-ZA-M2.

An alkyl ester of Formula I-ZA-M1 is reacted with from 1.5 to 4 molar equivalents (preferably 2 molar equivalents) of an inorganic hydroxide (such as potassium, sodium, or preferably lithium hydroxide) in a mixture of water and an organic solvent (such as tetrahydrofuran, methanol, or preferably dimethoxyethane). The reaction takes place at 0° to 60° C. (preferably 40° C.) over a period of 1 to 12 hours (preferably 3 hours). The resulting anion is acidified with an aqueous mineral acid (such as hydrochloric acid). The acidification takes place at 0° to 40° C. (preferably 25° C.) over a period of 1 to 10 minutes (preferably 2 minutes) to give the corresponding acid of Formula I-ZA-M2.

Preparation of Compounds of Formula I-ZB

One method of preparing compounds of Formula I where Z is sidechain of Formula ZB, illustrated as compounds of Formula I-ZB, is shown below in Reaction Schemes ZB-A to ZB-A-1.

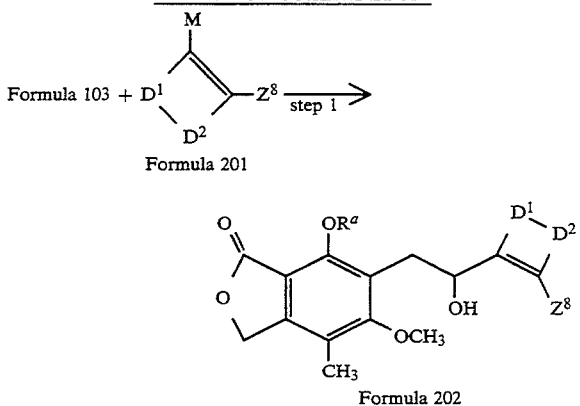

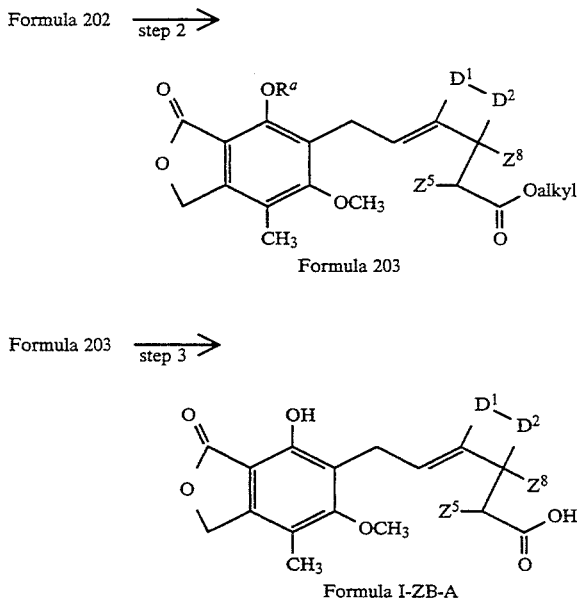

Preparation of Formula 202

As illustrated in Reaction Scheme ZB-A, Step 1, the aldehyde of Formula 103 is converted to a carbinol of Formula 202 by addition of an unsaturated cyclic organometallic compound of Formula 201 where M is Li or MgBr, prepared for example as described above with reference to Reaction Scheme ZA-A, Step 3.

One molar equivalent of the organometallic reagent 201 is added to a solution of an aldehyde of Formula 103 (in the same solvent system used to make the organometallic reagent). The reaction takes place at −80° to −20° C. (preferably −40° C.) over a period of 5 to 60 minutes (preferably 15 minutes) to give the corresponding carbinol of Formula 202.

Resolution of Formula 202

The racemic compound of Formula 202 may be separated into its two enantiomers by conventional means, for example by conversion into two diastereoisomers that are then separated by crystallization, chromatography, or by any conventional separation technique. Preferably, the carbinol is reacted with a chiral isocyanate to give a mixture of diastereoisomeric carbamates, which are separated by chromatography and cleaved to give the pure enantiomers.

A carbinol of Formula 202 is heated at 30° to 100° C. (preferably about 60° C.) with 2 to 6 molar equivalents (preferably 4 molar equivalents) of a chiral isocyanate in the presence of 1 to 1.5 molar equivalents (preferably 1.2 molar equivalents) of a strong organic base, for example 4-dimethylaminopyridine, in a hindered tertiary amine (for example diisopropylethylamine) as a solvent. The reaction takes place over a period of 1 to 24 hours (preferably 7 hours) to give the corresponding carbamate as a mixture of diastereoisomers.

The mixture of diastereoisomeric carbamates is separated by conventional means, preferably chromatography. The individual diastereoisomers are then separately cleaved by treatment with 1 to 1.5 molar equivalents (preferably 1.2 molar equivalents) of a trihalosilane, for example trichlorosilane, in the presence of an excess of a tertiary amine, for example triethylamine, in an inert solvent, for example toluene. The reaction takes place at a temperature of 90°–120° C. (preferably 110° C.) over a period of 5 minutes to 2 hours (preferably 15 minutes) to give the corresponding enantiomer of the carbinol of Formula 202.

Preparation of Formula 203

As illustrated in Reaction Scheme ZB-A, Step 2, an alkyl ester of Formula 203 is formed by a Claisen ortho ester reaction of a carbinol of Formula 201 (or an enantiomer thereof) with an appropriately substituted orthoester.

A carbinol of Formula 202 is heated at 50° to 140° C. (preferably 130° C.) with a large excess of an orthoester of Formula 104a (see Reaction Scheme ZA-A, step 4), in the presence of from 0.05 to 0.25 molar equivalents (preferably 0.10 molar equivalents) of an organic acid catalyst (such as propionic, butyric, or trimethylacetic acid, preferably trimethylacetic acid). The reaction takes place over a period of 1 to 24 hours (preferably 2.5 hours) to give the corresponding alkyl ester of Formula 203.

Preparation of Formula I-ZB-A

Compounds of Formula I-ZB-A are prepared as described above with reference to Reaction Scheme ZA-M, Step 1 (deprotection to afford the corresponding alkyl ester), and Step 2 (hydrolysis to afford the corresponding acid of Formula I-ZB-A).

Alternative Preparation of Enantiomers of Compounds of Formula I-ZB

Another method of preparing individual enantiomers of compounds of Formula I where Z is sidechain ZB, illustrated as compounds of Formula I-ZB, is from chiral compounds of Formula 202b, the preparation of which is shown below in Reaction Scheme ZB-A-1.

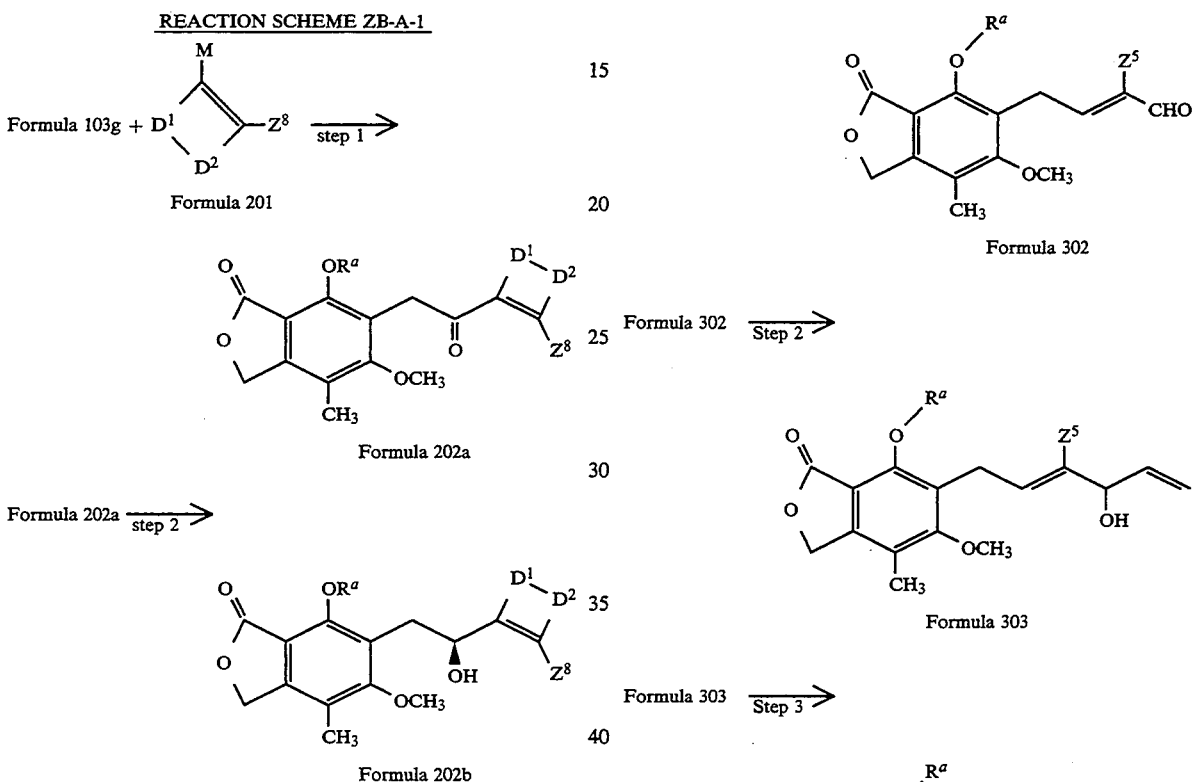

Preparation of Formula 202a

Compounds of Formula 202a are prepared as described above with reference to Reaction Scheme ZA-A-1, Step 3 (conversion of 103g to 103h).

Preparation of Formula 202b

Compounds of Formula 202b are prepared as described above with reference to Reaction Scheme ZA-A-1, Step 4 (conversion of 103h to 104b).

Preparation of Enantiomers of Compounds of Formula I-ZB

The chiral carbinol of Formula 202b is then converted to an enantiomer of a compound of Formula I-ZB in the same manner as shown above in Reaction Scheme ZB-A (conversion of Formula 202 to 203 to I-ZB-A).

Preparation of Compounds of Formula I-ZC

One method of preparing compounds of Formula I where Z is sidechain of Formula ZC, illustrated as compounds of Formula I-ZC, is shown below in Reaction Scheme ZC-A.

-continued
REACTION SCHEME ZC-A

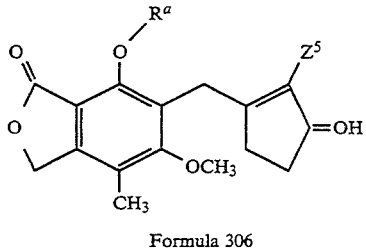

Formula 306

Formula 306 $\xrightarrow{\text{Step 6}}$

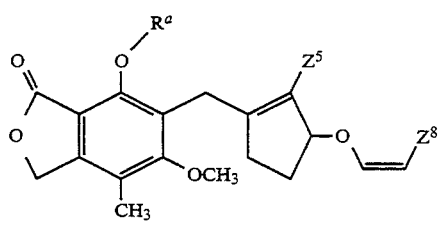

Formula 307

Formula 307 $\xrightarrow{\text{Step 7}}$

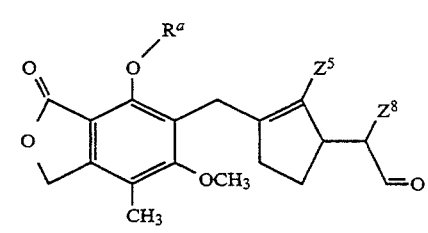

Formula 308

Formula 308 $\xrightarrow{\text{Step 8}}$

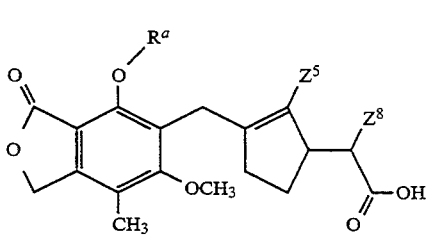

Formula 309

Formula 309 $\xrightarrow{\text{Step 9}}$

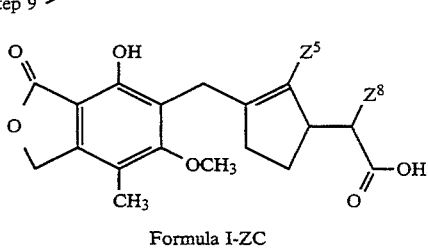

Formula I-ZC

Preparation of Formula 302

As illustrated in Reaction Scheme ZC-A, Step 1, an aldehyde of Formula 103 (prepared, for example as described above with reference to Reaction Scheme ZA, Steps 1 and 2) is transformed into an unsaturated aldehyde of Formula 302 by a Wittig reaction with an ylid of Formula 301 (where $Z^5$ is H or lower alkyl).

An aldehyde of Formula 103 is reacted with one molar equivalent of an ylid of Formula 301, in an organic solvent (such as dichloromethane, dimethylformamide or preferably toluene). The reaction takes place at 0° to 110° C. (preferably 80° C.) for 1 to 24 hours (preferably 8 hours) to give the corresponding unsaturated aldehyde of Formula 302.

Preparation of Formula 303

As illustrated in Reaction Scheme ZC-A, Step 2, an unsaturated aldehyde of Formula 302 is converted to the corresponding vinyl carbinol of Formula 303.

An aldehyde of Formula 302 is reacted with from 1.0 to 1.25 (preferably 1.1) molar equivalents of an organovinyl compound (preferably vinylmagnesium bromide) in a solvent (such as ether or preferably tetrahydrofuran). The reaction takes place at −30° to 20° C. (preferably at 0° C.) for 0.1 to 4 hours (preferably 0.5 hours) to give the corresponding vinyl carbinol of Formula 303.

Preparation of Formula 304

As illustrated in Reaction Scheme ZC-A, Step 3, a vinyl carbinol of Formula 303 is oxidized to give the corresponding dienone of Formula 304.

A vinyl carbinol of Formula 303 is reacted with 1.0 to 1.5 (preferably 1.1) molar equivalents of an oxidizing agent (such as manganese dioxide, pyridinium chlorochromate or preferably pyridinium dichromate) in a solvent (such as pyridine or preferably dichloromethane). The reaction takes place at 0° to 30° C. (preferably 25° C.) for 30 minutes to 4 hours (preferably 1 hour) to give the corresponding dienone of Formula 304.

Preparation of Formula 305

As illustrated in Reaction Scheme ZC-A, Step 4, a dienone of Formula 304 is cyclized to give the corresponding cyclopentenone of Formula 305.

A dienone of Formula 304 reacted with 0.3 to 1.5 (preferably 1.0) molar equivalents of a Lewis acid (such as boron trichloride, tin (IV) chloride or preferably boron trifluoride etherate) in a solvent (such as tetrachloroethane or preferably dichloromethane). The reaction takes place at 0° to 30° C. (preferably 25° C.) for 1 to 6 hours (preferably 2 hours) to give the corresponding cyclopentenone of Formula 305.

Preparation of Formula 306

As illustrated in Reaction Scheme ZC-A, Step 5, a cyclopentenone of Formula 305 is reduced to give the corresponding cyclopentenol of Formula 306.

A cyclopentenone of Formula 305 is reacted with 1.0 to 1.5 (preferably 1.1) molar equivalents of a reducing agent (such as lithium tri-tert-butoxyaluminium hydride or preferably sodium borohydride in the presence of an equimolar amount of cerium trichloride) in a mixture of an ethereal solvent (preferably tetrahydrofuran) and a lower alkanol (preferably methanol). The reaction takes place at 0° to 40° C. (preferably at 25° C.) for 1 to 6 hours (preferably 2 hours) to give the cyclopentenol of Formula 306.

Preparation of Formula 307

As illustrated in Reaction Scheme ZC-A, Step 6, a cyclopentenol of Formula 306 is transformed to the corresponding vinyl ether of Formula 307.

A cyclopentenol of Formula 306 is reacted with from 10 to 100 (preferably 50) molar equivalents of a 1-alkenyl ether, optionally in the presence of a co-solvent (such as ether or tetrahydrofuran), in the presence of from 0.1 to 0.5 (preferably 0.3) molar equivalents of a mercury (II) salt (preferably mercury (II) acetate). The reaction takes place at 0° to 50° C. (preferably 25° C.) for 1 to 5 days (preferably 2 days) to give the corresponding vinyl ether of Formula 307.

Preparation of Formula 308

As illustrated in Reaction Scheme ZC-A, Step 7, a vinyl ether of Formula 307 is rearranged to the corresponding acetaldehyde of Formula 308.

A vinyl ether of Formula 307 is reacted with from 10 to 100 (preferably 50) molar equivalents of a lithium salt (such as the tetrafluoroborate or preferably the perchlorate) in a solvent (such as tetrahydrofuran or preferably ether). The reaction takes place at 0° to 35° C. (preferably 25° C.) for 0.1 to 2 hours (preferably 0.5 hours) to give the corresponding acetaldehyde of Formula 308.

Preparation of Formula 309

As illustrated in Reaction Scheme ZC-A, Step 8, an acetaldehyde of Formula 308 is oxidized to give the corresponding acid of Formula 309.

An acetaldehyde of Formula 308 is reacted with 1 to 3 (preferably 1.5) molar equivalents of a suitable oxidizing agent [such as silver oxide, Jones reagent or sodium chlorite, preferably sodium chlorite in the presence of an equimolar amount of a phenol (such as quinol or preferably resorcinol)]. The reaction is conducted in a mixture of water and a water-miscible organic solvent (such as tetrahydrofuran or preferably dioxane) at a pH of from 4 to 6 (preferably 5) at −10° to 25° C. (preferably 0° C.) for 10 minutes to 2 hours (preferably 30 minutes) to give the corresponding acid of Formula 309.

Preparation of Formula I-ZC

As illustrated in Reaction Scheme ZC-A, Step 9, an acid of Formula is deprotected to give the corresponding acid of Formula I-ZC.

An acid of Formula 309 where $R^a$ is a sulphonyloxy protecting group hydrolyzed under basic conditions, using from 1 to 5 (preferably 3) molar equivalents of an alkali metal hydroxide (preferably lithium hydroxide) in a mixture of water and a water-miscible organic solvent (such as dioxane or preferably methanol). The reaction takes place at 40° to 100° C. (preferably 60° C.) for 1 to 48 hours (preferably 12 hours) to afford the corresponding cyclopentene carboxylic acid of Formula I-ZC.

Alternatively, for other protecting groups, the deprotection reaction takes place as described above with reference to Reaction Scheme ZA-M, Step 1.

Preparation of Compounds of Formula I-ZD

One method of preparing compounds of Formula I where Z is sidechain of Formula ZD, illustrated as compounds of Formula I-ZD, is shown below in Reaction Scheme ZD-A.

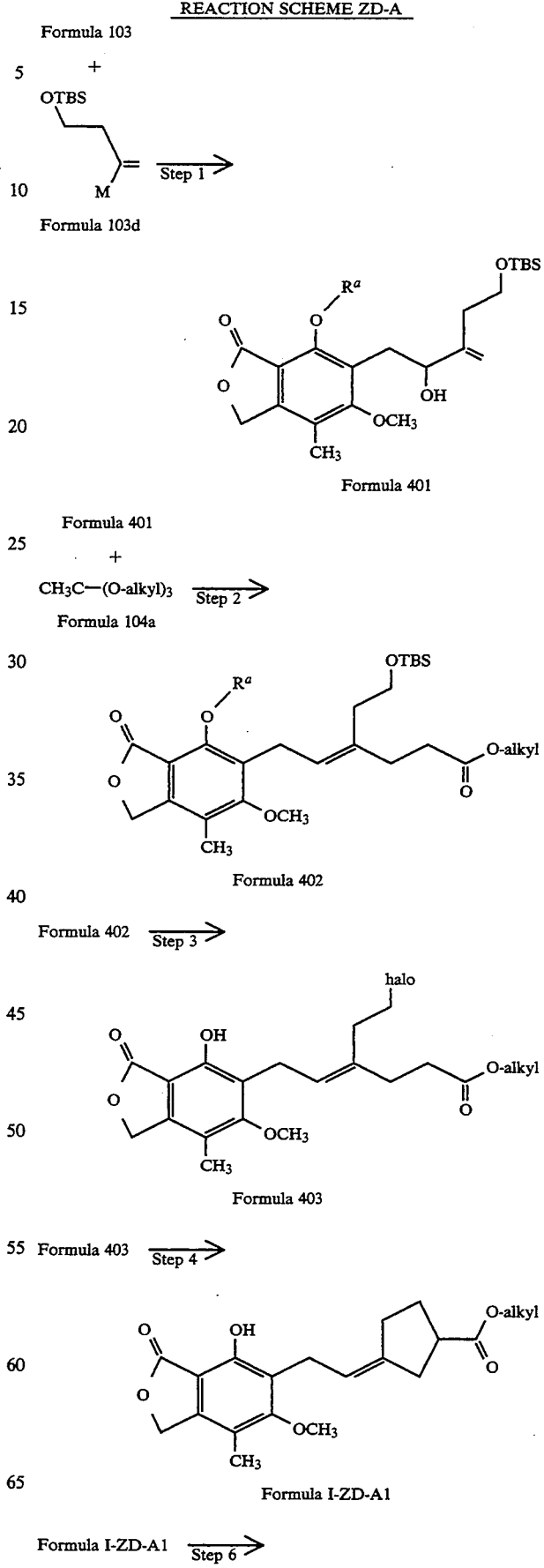

-continued
REACTION SCHEME ZD-A

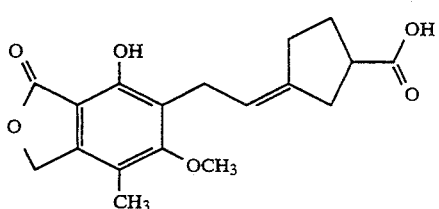

Formula I-ZD-A2

Preparation of Formula 401

As illustrated in Reaction Scheme ZD-A, Step 1, an aldehyde of Formula 103 (where $R^a$ is a silyl protecting group) is converted to a carbinol by addition of an organometallic compound of Formula 103d (such as a substituted vinyl organolithium, or preferably a Grignard reagent where: M is MgBr or Li; $Z^2$ is H or lower alkyl; and TBS is a tert-butyldimethylsilyl protecting group).

The aldehyde of Formula 103 is reacted with from 1.1 to 1.5 (preferably 1.25) molar equivalents of an organometallic, preferably organolithium, derivative of a protected 2-halo(2-bromo or preferably 2-iodo)but-1-en-4-ol. The reaction is performed at from $-100°$ to $-40°$ C. (preferably at $-78°$ C.) for from 30 minutes to 6 hours (preferably 1 hour) to afford the corresponding compound of Formula 401.

Preparation of Formula 402

As illustrated in Reaction Scheme ZD-A, Step 2, an alkyl ester of Formula 402 is formed by a Claisen ortho ester rearrangement reaction of a carbinol of Formula 401 and a trialkyl orthoacetate of Formula 104a.

A carbinol of Formula 401 is heated at 50° to 120° C. (preferably about 100° C.) with about 10 molar equivalents of an orthoester of Formula 104a, in the presence of from 0.05 to 0.25 (preferably 0.10) molar equivalents of an organic acid catalyst (such as propionic, butyric, or preferably trimethylacetic acid). The reaction takes place over a period of 1 to 48 hours (preferably 8 hours) to give the corresponding alkyl ester of Formula 402.

Preparation of Formula 403

As illustrated in Reaction Scheme ZD-A, Step 3, an alkyl ester of Formula 402 is reacted with a tetraalkylammonium fluoride and then halogenated to give a protected ester of Formula 403.

A compound of Formula 402 is reacted with from 2.0 to 3.0 (preferably 2.0) molar equivalents of a tetraalkylammonium (preferably tetrabutylammonium) fluoride, in a solvent (such as dioxane or preferably tetrahydrofuran or dichloromethane) at from 0° to 25° C. (preferably 10° C.), for from 30 minutes to 4 hours (preferably 1 hour). The product so obtained is reacted with from 1.0 to 1.5 (preferably 1.25) molar equivalents of a halogenating agent (preferably a brominating agent, such as triphenylphosphine/carbon tetrabromide or preferably triphenylphosphine/N-bromosuccinimide) in a solvent such as ether or preferably dichloromethane. The reaction takes place at from $-40°$ to 0° C. (preferably $-10°$ C.) for from 1 to 6 hours (preferably 4 hours) to give the corresponding halogenated ester of Formula 403.

Preparation of Formula I-ZD-A1

As illustrated in Reaction Scheme ZD-A, Step 4, a halogenated ester of Formula 403 is cyclized to give a protected cycloalkyl ester of Formula I-ZD-A1.

A compound of Formula 403 is reacted with from 2.0 to 2.5 (preferably 2.25) molar equivalents of a strong base (such as lithium diisopropylamide, sodium hydride or preferably sodium hexamethyldisilazide) in an ethereal solvent (such as ether, dioxane or preferably tetrahydrofuran) The reaction takes place at from $-100°$ to $-60°$ C. (preferably $-78°$ C.) for 1 to 12 hours (preferably 4 hours) to give the protected cycloalkyl ester of Formula I-ZD-A1.

Preparation of Formula I-ZD-A2

As illustrated in Reaction Scheme ZD-A, Step 6, a cycloalkyl ester of Formula I-ZD-A1 is hydrolyzed to give the corresponding acid of Formula I-ZE-D2. The hydrolysis reaction takes place as described above with reference to Reaction Scheme ZA-M, Step 2.

Preparation of Compounds of Formula I-ZE

One method of preparing compounds of Formula I where Z is sidechain of Formula ZE, illustrated as compounds of Formula I-ZE, is shown below in Reaction Schemes ZE-A to ZE-E.

REACTION SCHEME ZE-A

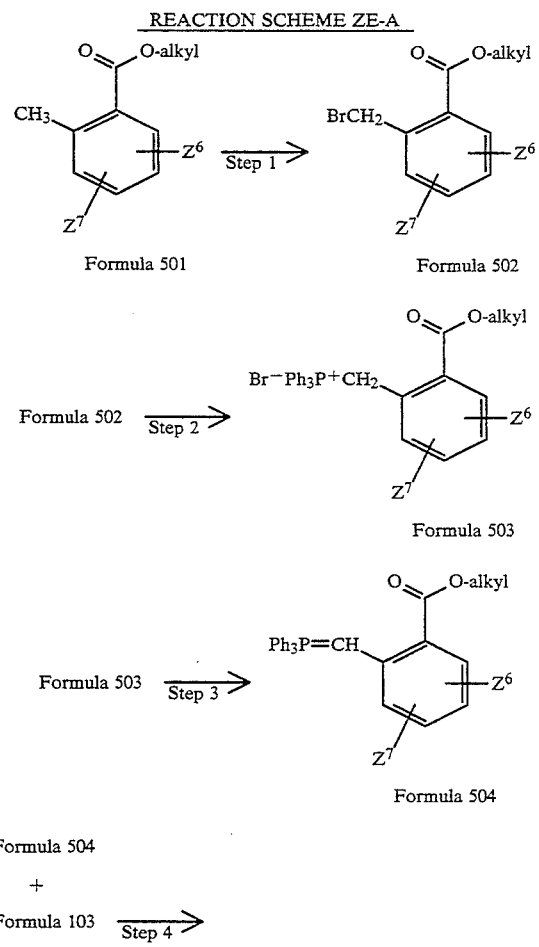

-continued
REACTION SCHEME ZE-A

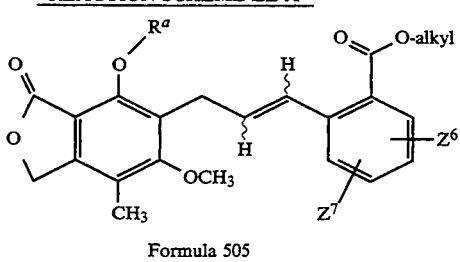

Formula 505

Formula 505 $\xrightarrow{\text{Step 5}}$

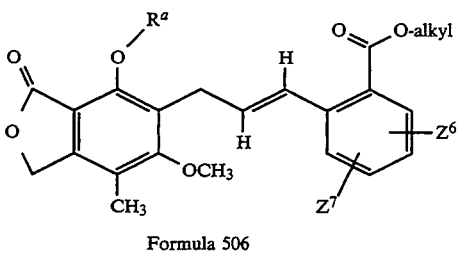

Formula 506

Preparation of Formula 502

As illustrated in Reaction Scheme ZE-A, Step 1, the 2-methyl group of an alkyl 2-methylbenzoate of Formula 501 (where $Z^6$ and $Z^7$ are selected from H, lower alkyl, halo and nitro) is brominated to give the corresponding compound of Formula 502.

An ester of Formula 501 is reacted with 1.0 to 1.2 (preferably 1.05) molar equivalents of a brominating agent (such as N-bromoacetamide or preferably N-bromosuccinimide), optionally in the presence of an initiator (such as visible light) or from 0.001 to 0.01 (preferably 0.005) molar equivalents of a chemical initiator (such as azobisisobutyronitrile or preferably benzoyl peroxide) in a solvent (such as ethyl formate or preferably carbon tetrachloride). The reaction takes place at 40° to 80° C. (preferably 75° C.) for 30 minutes to to 6 hours (preferably 2 hours) to afford the corresponding alkyl 2-bromomethylbenzoate of Formula 502, which can be purified by conventional means or preferably used directly for the next step.

Preparation of Formula 503

As illustrated in Reaction Scheme ZE-A, Step 2, a 2-bromomethyl group of Formula 502 is converted to the corresponding phosphonium salt of Formula 503.

A 2-bromomethylbenzoate of Formula 502 is reacted with 1.0 to 1.25 (preferably 1.05) molar equivalents of a triaryl phosphine (preferably triphenyl phosphine) in a solvent (such as dimethylformamide or preferably acetonitrile). The reaction takes place at 25° to 90° C. (preferably 50° C.) for 1 to 24 hours (preferably 2 hours) to afford the corresponding phosphonium salt of Formula 503.

Preparation of Formula 504

As illustrated in Reaction Scheme ZE-A, Step 3, a phosphonium salt of Formula 503 is converted to the corresponding substituted benzylidenetriphenylphosphorane ylid of Formula 504.

A phosphonium salt of Formula 503 is dissolved or suspended in a solvent (such as dioxane, ether or preferably dimethylformamide) and reacted with 1.0 to 1.25 (preferably 1.05) molar equivalents of a base (such as sodium hydride, triethylamine or preferably 1,5-diazabicyclo-[4.3.0]non-5-ene). The reaction takes place at 0° to 60° C. (preferably 25° C.) for 1 to 6 hours (preferably 2 hours) to afford the corresponding ylid of Formula 504, which can be isolated by conventional means or its solution can be used directly for the next step.

Preparation of Formulae 505 and 506

As illustrated in Reaction Scheme ZE-A, Step 4, an ylid of Formula and a protected aldehyde of Formula 103 (prepared, for example, as described in connection with Reaction Scheme ZA-A, Step 2) are employed in a Wittig reaction to give the corresponding protected substituted benzoic acid alkyl ester of Formula 505 as a mixture of E and Z isomers, from which the desired E isomer of Formula 506 is isolated, as illustrated in Reaction Scheme ZE-A, Step 5.

A solution of 0.8 to 1.0 (preferably 0.95) molar equivalents of a protected aldehyde of Formula 103 in a solvent (such as ether, dioxane or preferably dimethylformamide) is added to a solution of an ylid of Formula 504 in the same solvent. The reaction takes place at 0° to 50° C. (preferably 25° C.) for 1 to 24 hours (preferably 12 hours) to afford the corresponding protected substituted benzoic acid alkyl ester of Formula 505 as a mixture of E and Z isomers, from which the desired E-isomer of Formula 506 can be isolated by conventional means (such as distillation, chromatography or preferably fractional crystallization).

REACTION SCHEME ZE-B

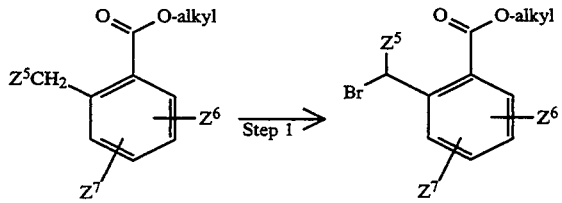

Formula 507       Formula 508

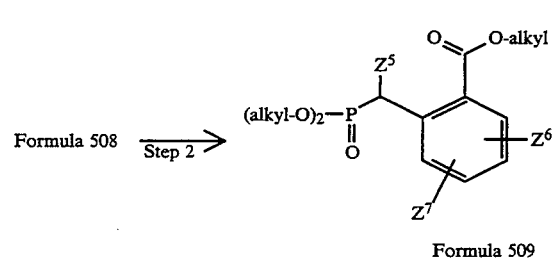

Formula 508 $\xrightarrow{\text{Step 2}}$

Formula 509

Formula 509

+

Formula 103 $\xrightarrow{\text{Step 3}}$

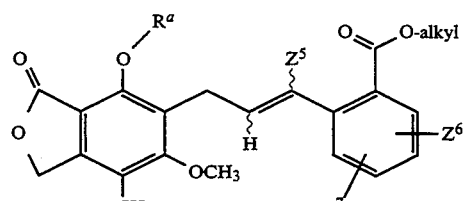

Formula 510

-continued
REACTION SCHEME ZE-B

Formula 510 $\xrightarrow{\text{Step 4}}$

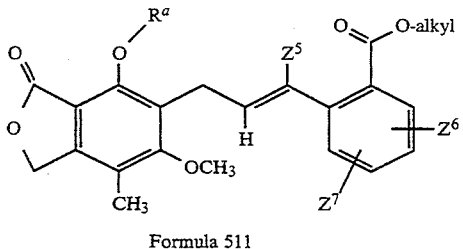

Formula 511

Preparation of Formula 508

As illustrated in Reaction Scheme ZE-B, Step 1, the alpha carbon of an alkyl 2-alkylbenzoate of Formula 507 (where $Z^5$ is H or lower alkyl, and $Z^6$ and $Z^7$ are selected from H, lower alkyl, halo and nitro) is brominated to give the corresponding compound of Formula 508. The reaction takes place under conditions described with reference to Reaction Scheme ZE-A, Step 1.

Preparation of Formula 509

As illustrated in Reaction Scheme ZE-B, Step 2, an alkyl 2-bromoalkylbenzoate of Formula 508 and a trialkyl phosphite are combined in an Arbuzov reaction to give the corresponding phosphonate of Formula 509.

A compound of Formula 508 is reacted with from 5 to 20 (preferably 10) molar equivalents of a trialkyl phosphite (preferably triethyl phosphite). The reaction takes place at 100° to 200° C. (preferably 150° C.) for 1 to 24 hours (preferably 6 hours) to afford the corresponding phosphonate of Formula 509.

Preparation of Formulae 510 and 511

As illustrated in Reaction Scheme ZE-B, Step 3, a phosphonate of Formula 509 and a protected aldehyde of Formula 103 (prepared, for example, as described in connection with Reaction Scheme ZA-A, Step 2) are reacted to give the corresponding protected substituted benzoic acid alkyl ester of Formula 510 as a mixture of E and Z isomers, from which the desired E isomer of Formula 511 is isolated, as illustrated in Reaction Scheme ZE-B, Step 4.

A phosphonate of Formula 509 is reacted with 1.0 to 1.5 (preferably 1.1) molar equivalents of a base such (as sodium amide, potassium tert-butoxide or preferably sodium hydride) for from 1 to 4 hours (preferably 2 hours) at 0° to 50° C. (preferably 25° C.) in a solvent (such as dioxane, dimethylformamide or preferably dimethoxyethane), to give a solution or suspension of the corresponding alkali metal salt of Formula 509, which is employed without isolation or further purification. The alkali metal salt is reacted with from 0.9 to 1.1 (preferably 1.0) molar equivalents of a protected aldehyde of Formula 103, dissolved in the same solvent. The reaction takes place at 0° to 60° C. (preferably 40° C.) for 1 to 6 hours (preferably 2 hours) to afford the corresponding protected optionally substituted benzoic acid alkyl ester of Formula 510 as a mixture of E and Z isomers, from which the desired E-isomer of Formula 511 can be isolated by conventional means (such as distillation, chromatography or preferably fractional crystallization).

REACTION SCHEME ZE-C

Formula 103
+
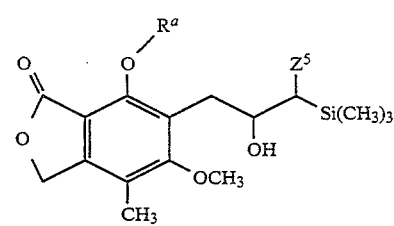
Formula 512

$\xrightarrow{\text{Step 1}}$

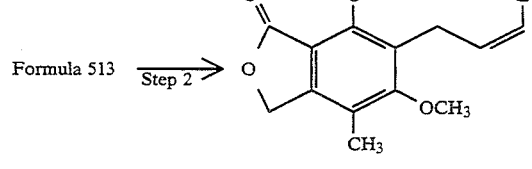

Formula 513

Formula 513 $\xrightarrow{\text{Step 2}}$

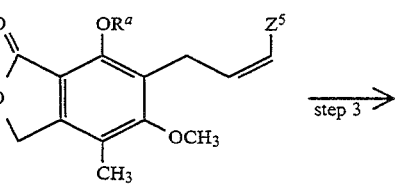

Formula 514

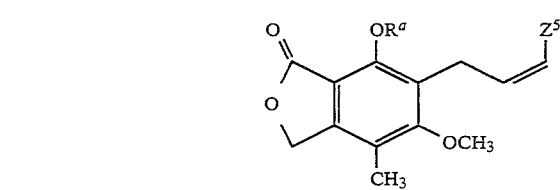

Formula 514
where $R^a$ is TBDMS step 3 $\longrightarrow$

Formula 515
where $R^a$ is acyl

Formula 515
+
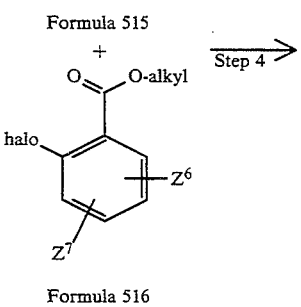

Formula 516

$\xrightarrow{\text{Step 4}}$

-continued
REACTION SCHEME ZE-C

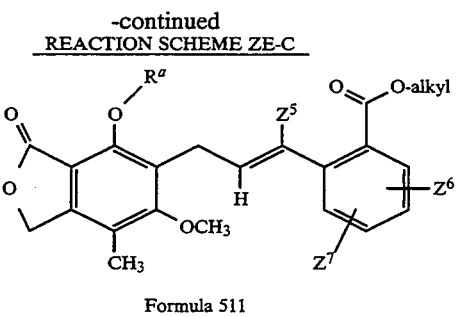

Formula 511

Preparation of Formula 513

As illustrated in Reaction Scheme ZE-C, Step 1, a protected aldehyde of Formula 103 is converted to a trialkylsilylcarbinol of Formula 513 in a Grignard reaction.

An aldehyde of Formula 103 is reacted with from 1.0 to 1.25 (preferably 1.1) molar equivalents of a trialkylsilylalkylmagnesium bromide (such as trimethylsilylpropylmagnesium bromide, or preferably trimethylsilylmethylmagnesium bromide) of Formula 512, in an ethereal solvent (such as ether, dimethoxyethane or preferably tetrahydrofuran). The reaction takes place at −40° to 40° C. (preferably 0° C.) for 30 minutes to 4 hours (preferably 1 hour) to give the corresponding trialkylsilylcarbinol of Formula 513.

Preparation of Formula 514

As illustrated in Reaction Scheme ZE-C, Step 2, a protected trialkylsilylcarbinol of Formula 513 is dehydrated to give the corresponding protected alkene as a mixture of E and Z isomers, from which the desired Z isomer of Formula 514 is isolated.

A carbinol of Formula 513 is reacted with from 1.0 to 1.5 (preferably 1.05) molar equivalents of a sulphonyl chloride (such as p-toluenesulphonyl chloride or preferably methanesulphonyl chloride) in the presence of the same molar proportion of a tertiary organic base (such as N-methylpyrrolidine or preferably triethylamine). The reaction takes place at 0° to 40° C. (preferably 15° C.) for 30 minutes to 4 hours (preferably 2 hours) to afford the corresponding protected alkene of Formula 514 as a mixture of E and Z isomers, from which the desired Z-isomer of Formula 514 can be isolated by conventional means (such as distillation, chromatography or preferably fractional crystallization).

Preparation of Formula 515

As illustrated in Reaction Scheme ZE-C, Step 3, an alkene of Formula 514 where $R^a$ is a silyl protecting group is converted to an alkene of Formula 515 where $R^a$ is an acyl group.

An alkene of Formula 514 is heated at 50°–130° C. (preferably about 118° C.) with a large excess of a mixture (preferably about equimolar) of a carboxylic acid of Formula $R^aOH$ and an anhydride of Formula $(R^a)_2O$ (where $R^a$ is the desired acyl group), preferably a mixture of acetic acid and acetic anhydride. The reaction takes place over a period of 6 to 48 hours (preferably 18 hours) to give the corresponding alkene of Formula 515 where $R^a$ is the acyl group.

Preparation of Formula 511

As illustrated in Reaction Scheme ZE-C, Step 4, a protected alkene of Formula 515 is converted to a protected optionally substituted benzoic acid alkyl ester of Formula 511 in a Heck reaction with an alkyl-2-halobenzoate of Formula 515.

An alkene of Formula 515 is reacted with 1.0 to 2.0 (preferably 1.25) molar equivalents of an alkyl 2-halobenzoate (such as an alkyl 2-bromobenzoate or preferably 2-iodobenzoate). The reaction is conducted in the presence of from 0.001 to 0.1 (preferably 0.05) molar equivalents of a palladium catalyst [such as tetrakis(tri-o-tolylphosphine)palladium, or tetrakis(triphenylphosphine)palladium or preferably palladium (II) acetate] optionally in the presence of from 1.0 to 1.25 (preferably 1.05) molar equivalents of a base (such silver carbonate, sodium bicarbonate or preferably triethylamine), in a solvent (such as acetonitrile or preferably dimethylformamide). The reaction is conducted at from 0° to 120° C. (preferably 60° C.) for 1 to 48 hours (preferably 6 hours) to yield the corresponding protected optionally substituted benzoic acid alkyl ester of Formula 511.

REACTION SCHEME ZE-D

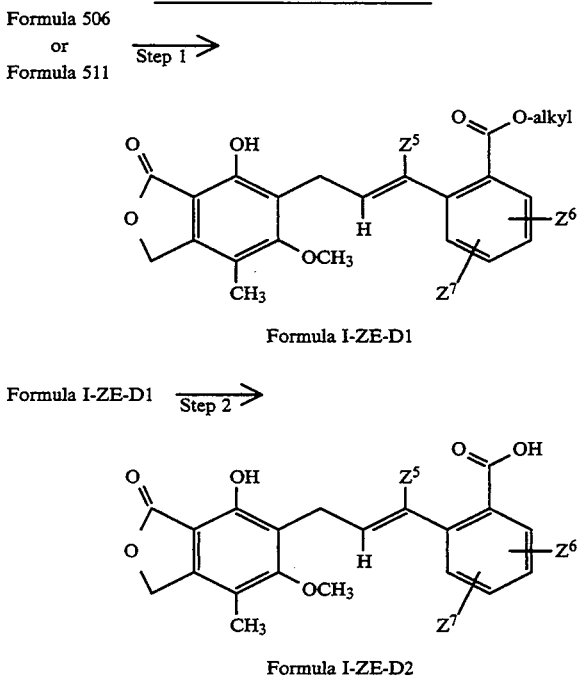

Preparation of Formula I-ZE-D1

As illustrated in Reaction Scheme ZE-D, Step 1, a protected optionally substituted benzoic acid ester of Formula 506 or Formula 511 is deprotected to give the corresponding ester of Formula I-ZE-D1. The deprotection reaction takes place as described above with reference to Reaction Scheme ZA-M, Step 1.

Preparation of Formula I-ZE-D2

As illustrated in Reaction Scheme ZE-D, Step 2, a deprotected optionally substituted benzoic acid ester of Formula I-ZE-D1 is hydrolyzed to give the corresponding acid of Formula I-ZE-D2. The hydrolization reaction takes place as described above with reference to Reaction Scheme ZA-M, Step 2. The compounds of Formula I-ZE-D2 where $Z^6$ is nitro are employed as precursors to the corresponding compounds of Formula I-ZE-E where $Z^6$ is amino (as illustrated in Reaction Scheme ZE-E, Step 1); the nitro compounds are also active as IMPDH inhibitors when tested as described below.

REACTION SCHEME ZE-E

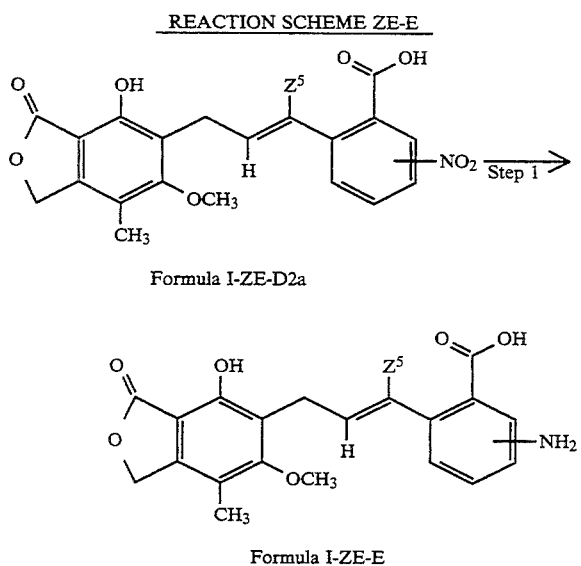

Formula I-ZE-D2a

Formula I-ZE-E

Preparation of Formula I-ZE-E

As illustrated in Reaction Scheme ZE-E, Step 1, a benzoic acid of Formula I-ZE-D2a (a compound of Formula I-ZE-D2 where $Z^6$ is $NO_2$) is reduced to the corresponding amino-substituted benzoic acid of Formula I-ZE-E.

A nitrobenzoic acid of Formula I-ZE-D2a is reacted with 1.0 to 3.0 (preferably 2.0) molar proportions of a reducing agent (such as sodium hydrosulfite or preferably tin (II) chloride) in hydrochloric acid solution, optionally in the presence of a water-miscible co-solvent (such as methanol or preferably acetic acid). The reaction takes place at 25° to 100° C. (preferably 75° C.) for 1 to 24 hours (preferably 4 hours) to afford the corresponding amino,substituted benzoic acid of Formula I-ZE-E.

REACTION SCHEME ZE-F

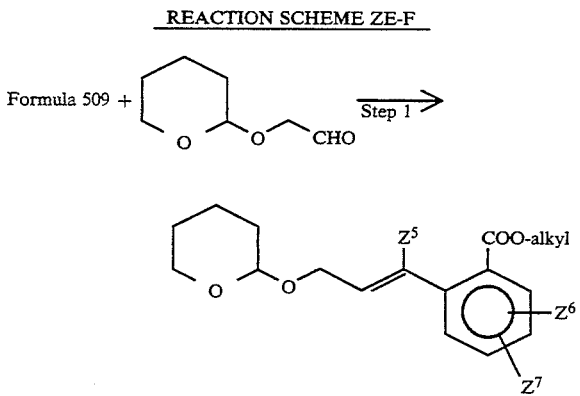

Formula 517

-continued
REACTION SCHEME ZE-F

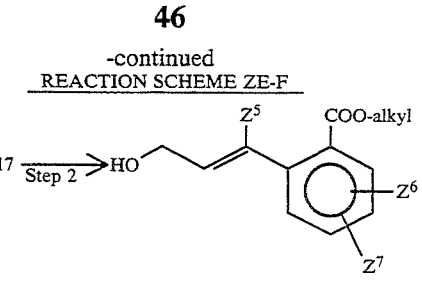

Formula 518

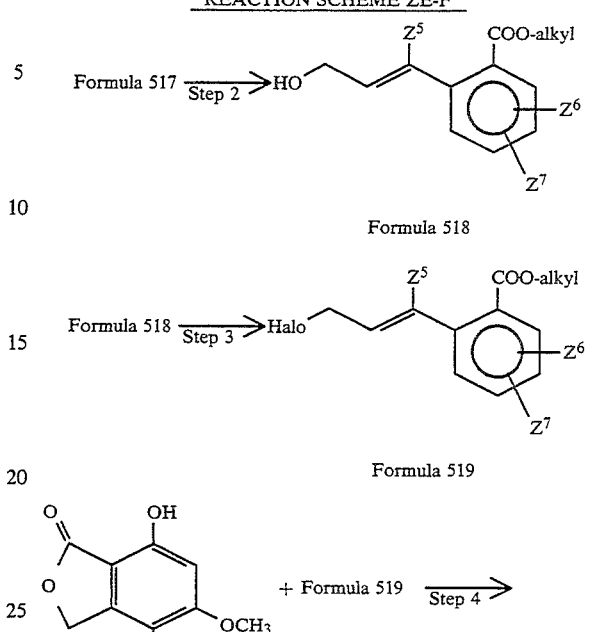

Formula 519

+ Formula 519 $\xrightarrow{\text{Step 4}}$

Formula 520

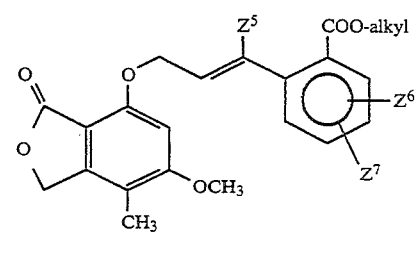

Formula 520 $\xrightarrow{\text{Step 5}}$

Formula I-ZE-D1 $\xrightarrow{\text{Step 6}}$ Formula I-ZE-D2

Preparation of Formula 517

As illustrated in Reaction Scheme ZE-F, Step 1, a phosphonate of Formula 509 undergoes a base catalyzed condensation (e.g., using 1 molar equivalent of sodium hydride) with tetrahydropyranyloxyacetaldehyde, in a solvent such as dimethylformamide. The reaction takes place at 25° C. over a period of 1 to 4 hours, to give E/Z mixture from which the desired product of Formula 517 can be isolated by conventional means, such as chromatography.

Preparation of Formula 518

As illustrated in Reaction Scheme ZE-F, Step 2, the tetrahydropyranyloxy group of a compound of Formula 517 is hydrolyzed in the presence of a catalytic amount of a dilute acid (e.g., HCl) in aqueous tetrahydrofuran. The reaction takes place at 25° C. over a period of 1 to 4 hours, to give the corresponding carbinol of Formula 518.

Preparation of Formula 519

As illustrated in Reaction Scheme ZE-F, Step 3, a carbinol of Formula 518 is converted to the halo (e.g., chloro or bromo) derivative of Formula 519 using 1 molar equivalent of triphenylphosphine and either carbon tetrachloride or carbon tetrabromide, in dichloromethane. The reaction takes place at 25° C. over a period of 2 hours.

Preparation of Formula 520

As illustrated in Reaction Scheme ZE-F, Step 4, a halo derivative of Formula 519 undergoes a base-catalyzed ether formation with the indicated phenol, using 5 molar equivalents of potassium carbonate, in dimethylformamide. The reaction takes place at 25° C. over a period of 4 hours.

Preparation of Formula I-ZE-D1 and Formula I-ZE-D2

As illustrated in Reaction Scheme ZE-F, Step 5, an ether of Formula 520 is rearranged to give the corresponding ester of Formula I-ZE-D1 (shown in Reaction Scheme ZE-D) by a thermal rearrangement catalyzed by Florisil ©. The rearrangement takes place in toluene at 110° C. over a period of one to four days.

As illustrated in Reaction Scheme ZE-F, Step 6, the ether so-produced is hydrolyzed to the corresponding acid of Formula I-ZE-D2 as described with reference to Reaction Scheme ZA-M, Step 2.

Preparation of Compounds of Formula I-ZF

One method of preparing compounds of Formula I where Z is sidechain of Formula ZF, illustrated as compounds of Formula I-ZF, is shown below in Reaction Scheme ZF-A.

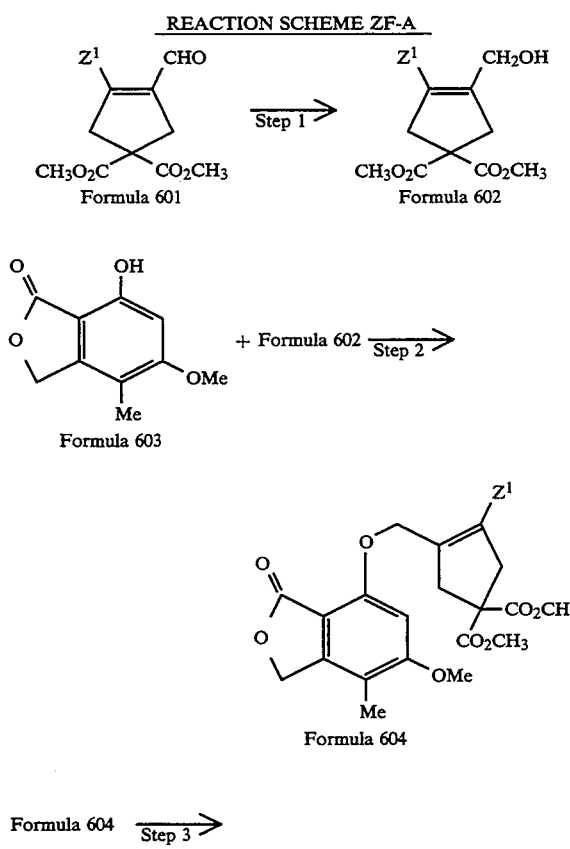

-continued
REACTION SCHEME ZF-A

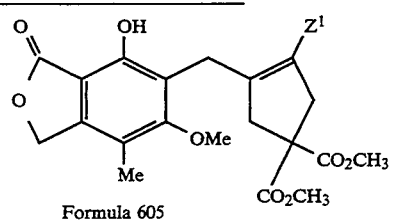

Formula 605

Formula 605 $\xrightarrow{\text{Step 4}}$

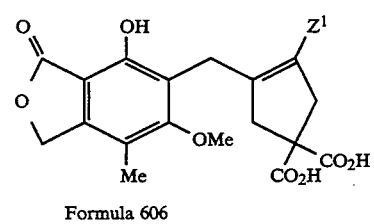

Formula 606

Formula 606 $\xrightarrow{\text{Step 5}}$

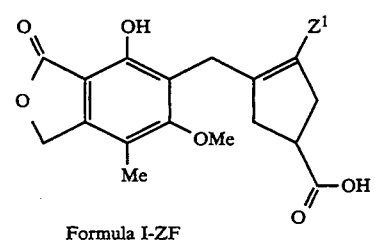

Formula I-ZF

Preparation of Formula 602

As illustrated in Reaction Scheme ZF-A, Step 1, an aldehyde of Formula 601, prepared for example as shown in *J. Org. Chem.*, 3408 (1977), is reduced to a carbinol of Formula 602.

An aldehyde of Formula 601 is reacted with a reducing agent capable of selectively reducing an aldehyde in the presence of ester groups, preferably from 1 to 2 (preferably 1.5) molar equivalents of sodium borohydride in the presence of from 1 to 2 (preferably 1.5) molar equivalents of cerium chloride trihydrate, in an alcoholic/ethereal solvent mixture (preferably 4:1 tetrahydrofuran:methanol). The reaction takes place at 0° to 40° C. (preferably 25° C.) for 10 minutes to 2 hours (preferably 30 minutes) to give the corresponding carbinol of Formula 602.

Preparation of Formula 604

As illustrated in Reaction Scheme ZF-A, Step 2, a phenol of Formula 603 is alkylated with a carbinol of Formula 602 by means of the Mitsonobu reaction to give an ether of Formula 604.

A carbinol of Formula 602 is reacted with an equimolar amount of a phenol of Formula 603 in the presence of from 1 to 3 (preferably 2) molar equivalents of a triarylphosphine, preferably triphenylphosphine, plus from 1 to 3 (preferably 1.5) molar equivalents of diethyl azodicarboxylate in an ethereal solvent (preferably tetrahydrofuran). The reaction takes place at 0° to 40° C. (preferably 25° C.) for 1 to 10 hours (preferably 3 hours) to give the corresponding ether of Formula 604.

Preparation of Formula 605

As illustrated in Reaction Scheme ZF-A, Step 3, a phenol of Formula 604 is thermally rearranged to give a diester of Formula 605.

An ether of Formula 604 is heated in an inert solvent (preferably toluene) in the presence of about 10 parts by weight of an activated magnesium silicate, preferably Florisil ©. The reaction takes place at reflux temperature for 1 to 10 days (preferably 4 days) to give the corresponding diester of Formula 605.

Preparation of Formula 606

As illustrated in Reaction Scheme ZF-A, Step 4, a diester of Formula 605 is hydrolyzed to give a dicarboxylic acid of Formula 606.

A diester of Formula 605 is reacted with an excess of an inorganic base, preferably about 50 molar equivalents of lithium hydroxide, in an aqueous solvent (preferably 5:1 methanol:water). The reaction takes place at 0° to 40° C. (preferably 25° C.) for 1 to 10 days (preferably 2 days) to give the corresponding dicarboxylic acid of Formula 606.

Preparation of Formula I-ZF

As illustrated in Reaction Scheme ZF-A, Step 5, a dicarboxylic acid of Formula 606 is decarboxylated to give a monocarboxylic acid of Formula I-ZF.

A dicarboxylic acid of Formula 606 is heated (optionally in the presence of a high boiling inert solvent, for example tetramethylbenzene, but preferably in the absence of any solvent). The reaction takes place at 160° to 240° C. (preferably 195° C.) for about 5 minutes to give the corresponding monocarboxylic acid of Formula I-ZF.

Preparation of Compounds of Formula I-ZG

One method of preparing compounds of Formula I where Z is sidechain of Formula ZG, illustrated as compounds of Formula I-ZG, is shown below in Reaction Scheme ZG-A.

REACTION SCHEME ZG-A

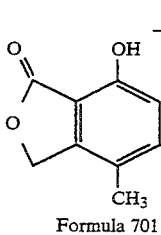

Formula 701

Formula 702

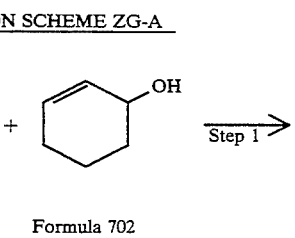

Step 1

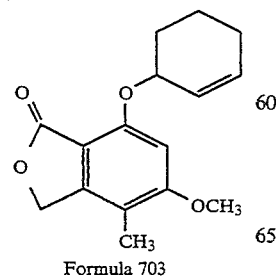

Formula 703

-continued
REACTION SCHEME ZG-A

Formula 703 $\xrightarrow{\text{Step 2}}$ 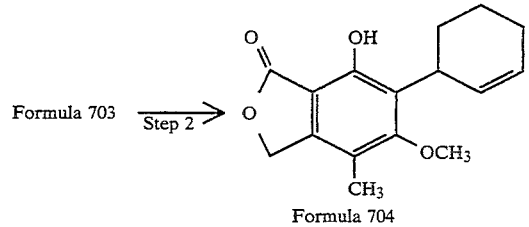

Formula 704

Formula 704 $\xrightarrow{\text{Step 3}}$ 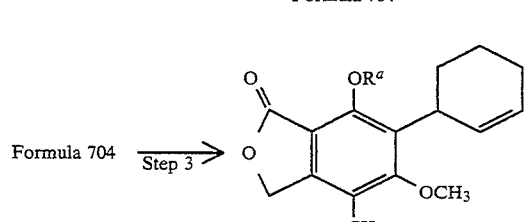

Formula 705

Formula 705 $\xrightarrow{\text{Step 4}}$ 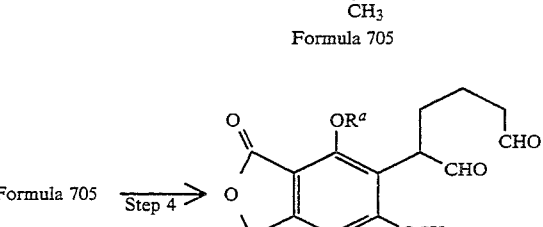

Formula 706

Formula 706 $\xrightarrow{\text{Step 5}}$ 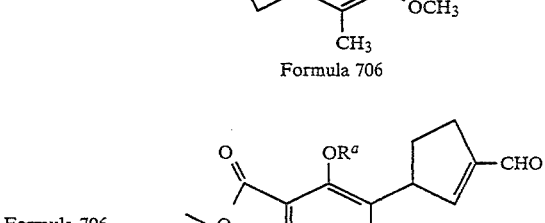

Formula 707

Formula 707 $\xrightarrow{\text{Step 6}}$

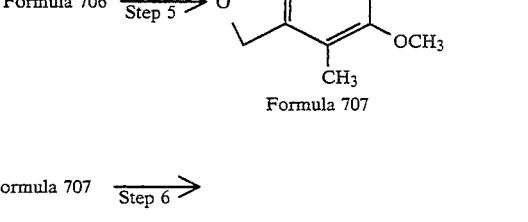

Formula 708

Formula 708 $\xrightarrow{\text{Step 7}}$

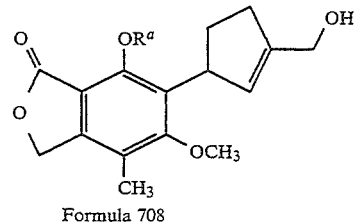

Formula 709

-continued
REACTION SCHEME ZG-A

Formula 709 →[Step 8]

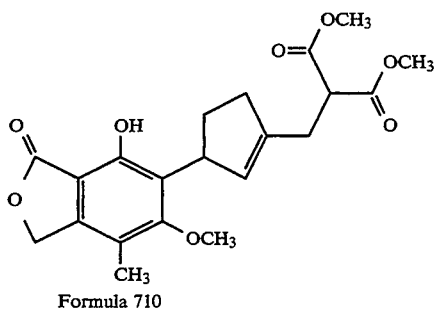

Formula 710

Formula 710 →[Step 9]

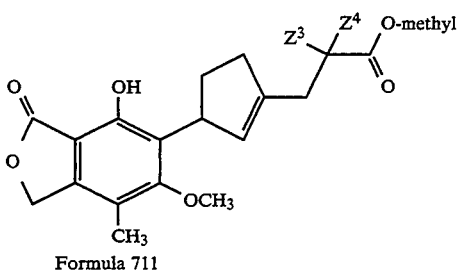

Formula 711

Formula 711 →[Step 10]

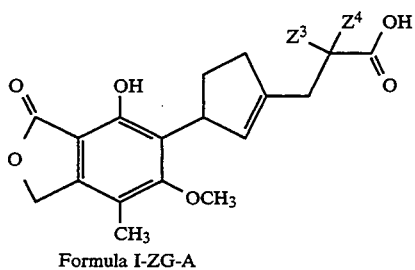

Formula I-ZG-A

Preparation of Formula 703

As illustrated in Reaction Scheme ZG-A, Step 1, the phenol of Formula 701 is alkylated with 3-hydroxycyclohexene to give the corresponding ether of Formula 703, by means of the Mitsonobu reaction. The Mitsonobu reaction takes place as described with reference to Reaction Scheme ZF-A, Step 2.

Similarly, by substituting 3-hydroxy-cyclohexene with 3-hydroxycycloheptene, and carrying out the procedures of Reaction Scheme ZG-A, the corresponding compounds where Z is a side chain of Formula ZG where $D^3$ is —$CH_2$—$CH_2$— are obtained.

Preparation of Formula 704

As illustrated in Reaction Scheme ZG-A, Step 2, a Claisen rearrangement of the ether of Formula 703 gives the alkylated phenol of Formula 704. The reaction takes place, e.g., at 200° C. for 12 to 16 hours in the presence of N,N-diethylaniline.

Preparation of Formula 705

As illustrated in Reaction Scheme ZG-A, Step 3, the alkylated phenol of Formula 704 is protected to give a protected phenol of Formula 705 (where $R^a$ is silyl or tosyl).

An alkylated phenol of Formula 704 is reacted with an equimolar amount of t-butyl dimethylsilyl chloride or p-toluenesulfonyl chloride, in the presence of an equimolar amount, respectively, of imidazole or 4-dimethylaminopyridine. The reaction takes place in dichloromethane at a temperature of 25° C. for 1 to 4 hours to give the corresponding protected phenol of Formula 705.

Preparation of Formula 706

As illustrated in Reaction Scheme ZG-A, Step 4, a protected phenol of Formula 705 is converted to the corresponding dialdehyde of Formula 706 by ozonolysis. The ozonolysis reaction takes place as described with reference to Reaction Scheme ZA-A, Step 2.

Preparation of Formula 707

As illustrated in Reaction Scheme ZG-A, Step 5, an intramolecular base-catalyzed aldol reaction with a dialdehyde of Formula 706 produces the corresponding formyl cyclopentene of Formula 707. The reaction is conducted with 0.1 moles oft dibenzylamine or N-methylaniline trifluoroacetate in benzene, taking place at 50° C. for 30 minutes.

Preparation of Formula 708

As illustrated in Reaction Scheme ZG-A, Step 6, a formyl cyclopentene of Formula 707 is reduced to the corresponding carbinol. The reaction employs sodium borohydride/cerium chloride, as described with reference to Reaction Scheme ZF-A, Step 1.

Preparation of Formula 709

As illustrated in Reaction Scheme ZG-A, Step 7, a carbinol of Formula 708 is converted to the corresponding acetate of Formula 709. The reaction is conducted with equimolar amounts of acetyl chloride and triethylamine, taking place in methylene chloride at 0° C. for 1 hour.

Preparation of Formula 710

As illustrated in Reaction Scheme ZG-A, Step 8, an acetate of Formula 709 is converted to the corresponding diester of Formula 710. The reaction is conducted as described in J. Am. Chem. Soc., 102:4730 (1980), with 4 moles of sodium dimethylmalonate, 0.5 moles triphenylphosphine and 0.25 moles of tetrakis triphenylphosphine palladium at 50° C. in tetrahydrofuran.

Preparation of Formula 711

As illustrated in Reaction Scheme ZG-A, Step 9, a diester of Formula 710 is converted to give the corresponding ester of Formula 711, by reaction with cesium acetate in hexamethylphosphoric triamide at 120° C. for 1 to 3 hours. Similarly, by use in Step 8 of an alternative for sodium dimethylmalonate suitably substituted to introduce $Z^3$ or $Z^4$, the correspondingly substituted ester of Formula 711 is obtained in Step 9.

Preparation of Formula I-ZG-A

As illustrated in Reaction Scheme ZG-A, Step 10, an ester of Formula 711 is hydrolyzed to give the corresponding compound of Formula I-ZG-A. The reactions take place as described with reference to Reaction Scheme ZA-M, Steps 1 and 2 respectively.

Preparation of Compounds of Formula I-ZH

One method of preparing compounds of Formula I where Z is sidechain of Formula ZH, illustrated as compounds of Formula I-ZH, is shown below in Reaction Scheme ZH-A.

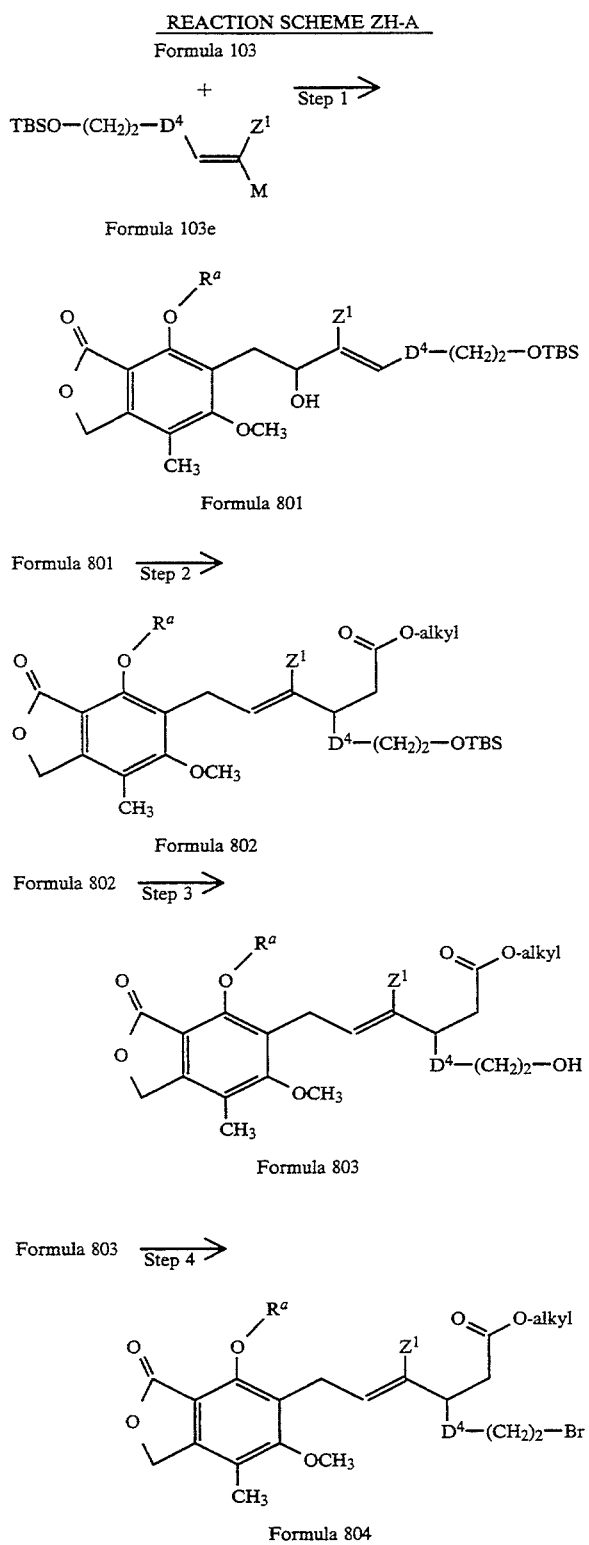

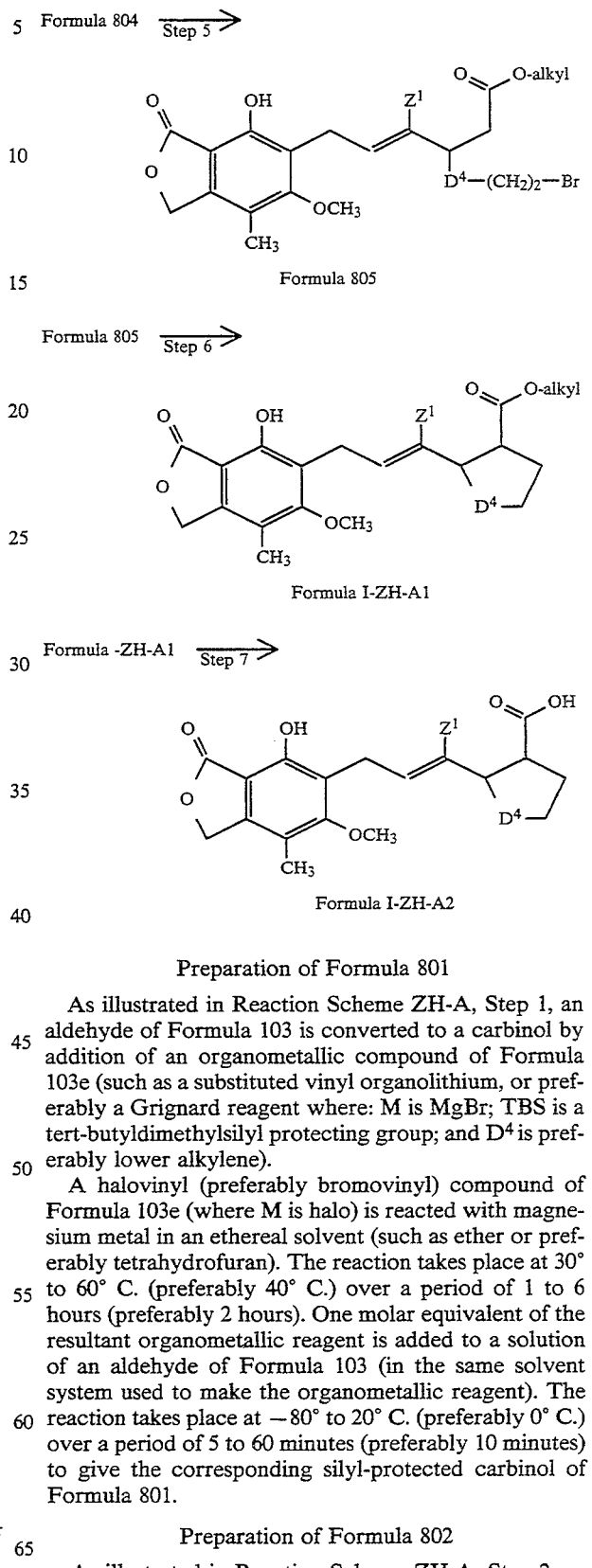

Preparation of Formula 801

As illustrated in Reaction Scheme ZH-A, Step 1, an aldehyde of Formula 103 is converted to a carbinol by addition of an organometallic compound of Formula 103e (such as a substituted vinyl organolithium, or preferably a Grignard reagent where: M is MgBr; TBS is a tert-butyldimethylsilyl protecting group; and $D^4$ is preferably lower alkylene).

A halovinyl (preferably bromovinyl) compound of Formula 103e (where M is halo) is reacted with magnesium metal in an ethereal solvent (such as ether or preferably tetrahydrofuran). The reaction takes place at 30° to 60° C. (preferably 40° C.) over a period of 1 to 6 hours (preferably 2 hours). One molar equivalent of the resultant organometallic reagent is added to a solution of an aldehyde of Formula 103 (in the same solvent system used to make the organometallic reagent). The reaction takes place at −80° to 20° C. (preferably 0° C.) over a period of 5 to 60 minutes (preferably 10 minutes) to give the corresponding silyl-protected carbinol of Formula 801.

Preparation of Formula 802

As illustrated in Reaction Scheme ZH-A, Step 2, an alkyl ester of Formula 802 is formed by a Claisen ortho ester rearrangement reaction of a carbinol of Formula 801 and an orthoester compound of Formula 104a (as illustrated in Reaction Scheme ZA-A, where $Z^3$ and $Z^4$ are H).

A silyl-protected carbinol of Formula 801 is heated at 50° to 120° C. (preferably about 100° C.) with about 10 molar equivalents of an orthoester of Formula 104a, in the presence of from 0.05 to 0.25 molar equivalents (preferably 0.10 molar equivalents) of an organic acid catalyst (such as propionic, butyric, or preferably trimethylacetic acid). The reaction takes place over a period of 1 to 48 hours (preferably 8 hours) to give the corresponding alkyl ester of Formula 802.

Preparation of Formula 803

As illustrated in Reaction Scheme ZH-A, Step 3, the silyl-protected carbinol of an alkyl ester of Formula 802 is deprotected.

A compound of Formula 803 is reacted with from 5 to 30 (preferably 20) molar equivalents of hydrogen fluoride, in a mixture of water and a water-miscible organic solvent (preferably acetonitrile). The reaction takes place at −20° to 40° C. (preferably 25° C.) for 5 to 60 minutes (preferably 30 minutes) to afford the corresponding unprotected carbinol/alkyl ester of Formula 803.

Preparation of Formula 804

As illustrated in Reaction Scheme ZH-A, Step 4, a carbinol of Formula 803 is converted to a halide (preferably a bromide) of Formula 804, by means of a one-step or a two-step procedure.

In the one-step procedure, a carbinol of Formula 803 is reacted with from 1.0 to 1.3 (preferably 1.1) molar equivalents of a triaryl (preferably triphenyl) phosphine, and from 1.0 to 1.3 (preferably 1.1) molar equivalents of a halogen source (such as N-bromosuccinimide or preferably carbon tetrabromide). The reaction is conducted in an inert solvent (such as ether or preferably tetrahydrofuran). The reaction takes place at 0° to 50° C. (preferably 25° C.) for 1 to 12 hours (preferably 3 hours) to afford the corresponding halide of Formula 804.

Alternatively, in the two-step procedure, which is preferred, a carbinol of Formula 803 is converted first into a sulphonate ester (such as a p-toluenesulphonate or preferably a methanesulphonate) by reaction with from 1.0 to 1.5 (preferably 1.3) molar equivalents a sulphonyl halide (preferably methanesulphonyl chloride) in the presence of an equimolar amount of a tertiary organic base (preferably diisopropylethylamine) in a solvent (such as chloroform or preferably dichloromethane). The reaction takes place at −20° to 30° C. (preferably 0° C.) for 10 to 60 minutes (preferably 30 minutes). The so-obtained sulphonate ester is then reacted with from 5 to 20 (preferably 20) molar equivalents of an alkali metal halide (preferably lithium bromide) in a solvent (such as 2-butanone or preferably acetone). The reaction takes place at 0° to 56° C. (preferably at reflux) for 30 to 180 minutes (preferably 90 minutes) to afford the corresponding halide of Formula 804.

Preparation of Formula 805

As illustrated in Reaction Scheme ZH-A, Step 5, a halogenated carbinol/alkyl ester of Formula 804 is deprotected at the phenolic group to give the corresponding halogenated carbinol/alkyl ester of Formula 805. The deprotection reaction takes place as described above with reference to Reaction Scheme ZA-M, Step 1.

Preparation of Formula I-ZH-A1

As illustrated in Reaction Scheme ZH-A, Step 6, a halogenated carbinol/alkyl ester of Formula 805 is subjected to a base-induced cyclization reaction to afford the product of Formula I-ZH-A1.

A compound of Formula 805 is reacted with from 2.0 to 2.5 (preferably 2.3) molar equivalents of a strong base (such as lithium diisopropylamide, sodium hydride or preferably sodium hexamethyldisilazide) in a solvent (such as dioxane or preferably tetrahydrofuran). The reaction takes place at −20° to 30° C. (preferably at 0° C.) for 5 to 60 minutes (preferably 15 minutes) to afford the corresponding cycloalkylester of Formula I-ZH-A1.

Preparation of Formula I-ZH-A2

As illustrated in Reaction Scheme ZH-A, Step 7, a cycloalkyl ester of Formula I-ZH-A1 is hydrolyzed to give the corresponding acid of Formula I-ZH-A2. The hydrolysis takes place as described above with reference to Reaction Scheme ZA-M, Step 2.

Compounds of Formula I where Z is a sidechain of Formula ZH in which $D^4$ is O or O—$CH_2$ are preferably prepared as described below in Reaction Scheme ZH-B.

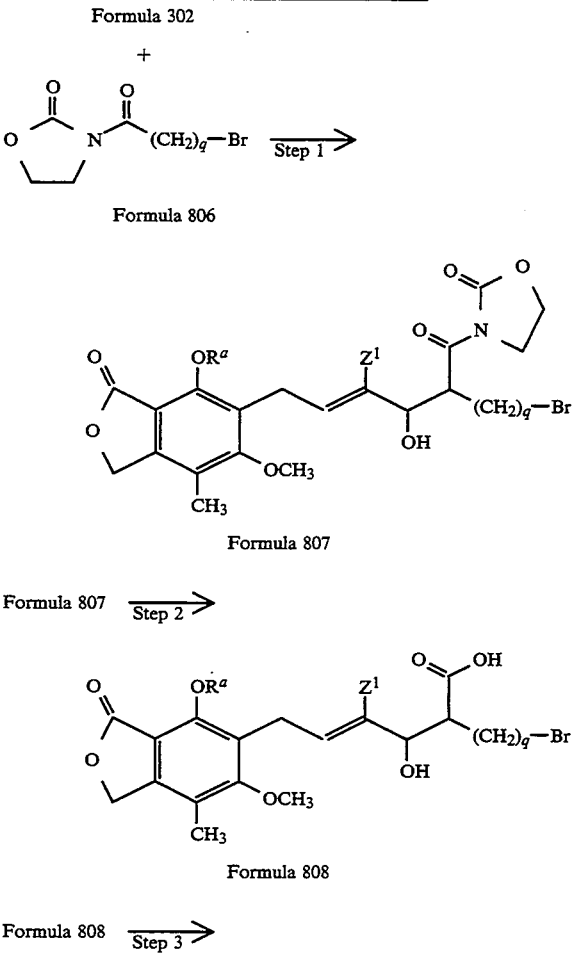

-continued
REACTION SCHEME ZH-B

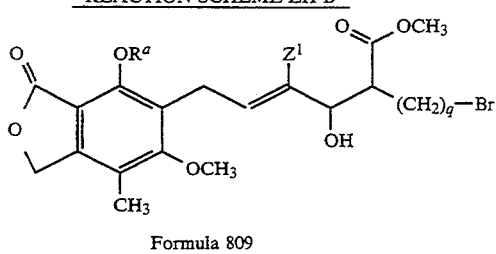

Formula 809

Formula 809 $\xrightarrow{\text{Step 4}}$

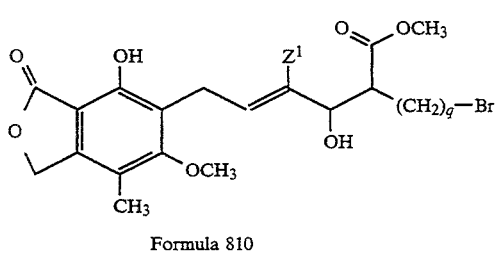

Formula 810

Formula 810 $\xrightarrow{\text{Step 5}}$

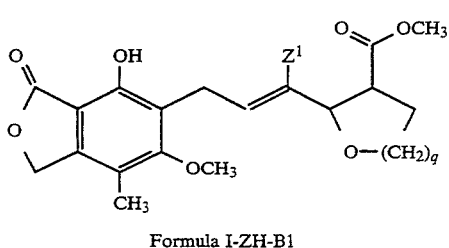

Formula I-ZH-B1

Formula I-ZH-B1 $\xrightarrow{\text{Step 6}}$

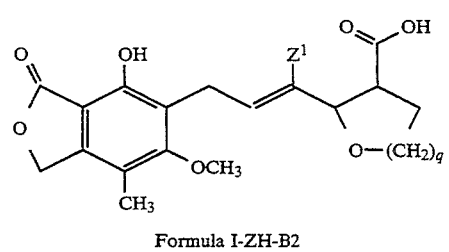

Formula I-ZH-B2

Preparation of Formula 807

As illustrated in Reaction Scheme ZH-B, Step 1, an aldehyde of Formula 302 (where $Z^5$ is methyl) undergoes an aldol reaction with the bromo-alkyl oxazolidinone of Formula 806 (where q is 1 or 2), which can be prepared by analogy with the reactions described in *J. Am. Chem. Soc.*, 103:2127 (1981), to give the acyloxazolidinone of Formula 807.

An oxazolidinone of Formula 806 is reacted with an equimolar amount of a base (such as lithium diisopropylamide or preferably di-n-butylboryl trifluoromethane sulphonate/triethylamine), and then with an aldehyde of Formula 302. The reaction takes place at −78° C. to 0° C. (preferably −40° C.) for 1 to 12 hours (preferably 3 hours) to afford the corresponding acyloxazolidinone of Formula 807.

Preparation of Formula 808

As illustrated in Reaction Scheme ZH-B, Step 2, an acyloxazolidinone of Formula 807 is hydrolyzed to the carboxylic acid of Formula 808.

An acyloxazolidinone of Formula 807 is reacted with 1–5 (preferably 3 molar equivalents of lithium hydroxide in 3:1 tetrahydrofuran containing 5–20 (preferably 12) molar equivalents of hydrogen peroxide. The reaction takes place at −10° to 25° C. (preferably 0°) for 5 to 60 minutes (preferably 30 minutes) to give the corresponding carboxylic acid of Formula 808.

Preparation of Formula 809

As illustrated in Reaction Scheme ZH-B, Step 3, a carboxylic acid of Formula 808 is deprotected to give the corresponding phenol of Formula 809, using the method described, with respect to Reaction Scheme ZA-M, Step 1.

Preparation of Formula 810

A phenol of Formula 809 is esterified to give the corresponding ester of Formula 810.

A phenol of Formula 809 is treated with methanol in the presence of 0.05 to 0.2 (preferably 0.1) molar equivalents of an acid catalyst (preferably p-toluenesulphonic acid). The reaction takes place at 0° to 50° C. (preferably 25° C.) for 1 to 24 hours (preferably 12 hours) to give the corresponding methyl ester of Formula 810.

Preparation of Formula I-ZH-B1

A methyl ester of Formula 810 undergoes an intramolecular cyclization reaction to give the corresponding cyclized ester of Formula I-ZH-B1.

A methyl ester of Formula 810 is treated with 1.9 to 2.5 (preferably 2.0) molar equivalents of a strong base (such as lithium diisopropylamide or preferably sodium hydride) in tetrahydrofuran (or preferably dimethylformamide). The reaction takes place at −10° to 25° C. (preferably 0°) for 1–12 hours (preferably 2 hours) to give the corresponding cyclized ester of Formula I-ZH-B1.

Preparation of Formula I-ZM-B2

As illustrated in Reaction Scheme ZH-B, Step 6, a cyclized ester of Formula I-ZH-B1 is hydrolyzed to give the corresponding acid of Formula I-ZH-B2, using the method described with respect to Reaction Scheme ZA-M, Step 2.

Preparation of Esters of Formula I

The esters of Formula I (compounds where G is not OH) can be prepared as described in U.S. Pat. Nos. 4,727,069 and 4,753,935, incorporated herein by reference, by deprotection of a precursor (e.g., as described with reference to Reaction Scheme ZA-M, Steps 1) or as described below by attachment of a leaving group and its replacement by the desired ester.

Attachment of Leaving Group

A carboxylic acid of Formula I is reacted with from 1.0 to 3.0, preferably about 1.5, molar equivalents of oxalyl chloride or preferably thionyl chloride, in a solvent (such as chloroform or preferably dichloromethane) optionally containing from 0.01 to 0.05 (preferably 0.03) molar equivalents of dimethylformamide. The reaction takes place at −10° to 30° C. (preferably 0° C.)

for 1 to 12 hours (preferably 2 hours) to give the corresponding acid chloride (where the leaving group is Cl).

Alternatively, a carboxylic acid of Formula I is reacted with 1.0 to 1.5 (preferably 1.25) molar equivalents of carbonyldiimidazole, in a solvent (such as tetrahydofuran or preferably dichloromethane). The reaction takes place at 0° to 40° C. (preferably 25° C.) for 1 to 12 hours (preferably 2 hours) to give the corresponding acyl imidazole (where the leaving group is 1-imidazolyl).

Esterification

A compound of Formula I where G has been replaced by a halide or imidazolide is reacted with from 1.0 to 5.0 (preferably 2) molar equivalents of a lower alkanol, optionally in the presence of from 1.0 to 1.5 (preferably 1.25) molar equivalents of a tertiary organic base (such as 4-dimethylaminopyridine or preferably triethylamine) in an organic solvent (such as dioxane, tetrahydrofuran or preferably dichloromethane). The reaction takes place at −10° to 50° C. (preferably 25° C.) for 1 to 24 hours (preferably 4 hours) to afford the corresponding lower alkyl ester of Formula I, which is employed in synthesis of the compounds of Formula A.

PREPARATION OF FORMULA A

The compounds of Formula A [where $R^2$ is lower alkyl, cycloalkyl, vinyl, fluorovinyl, difluorovinyl, trifluorovinyl, alkenyl, —C≡C—$R^{11}$, allenyl or $CH_2$—O—(4-methoxybenzyl), collectively designated as Formula AA] are prepared as described with reference to Reaction Scheme A.

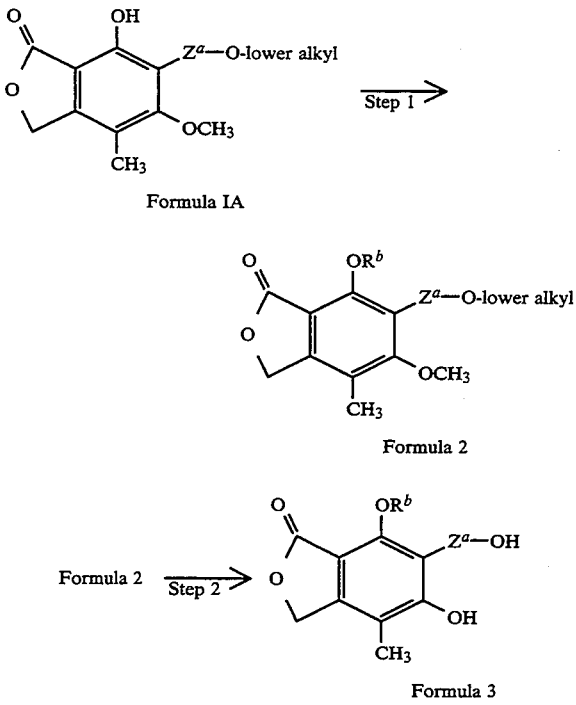
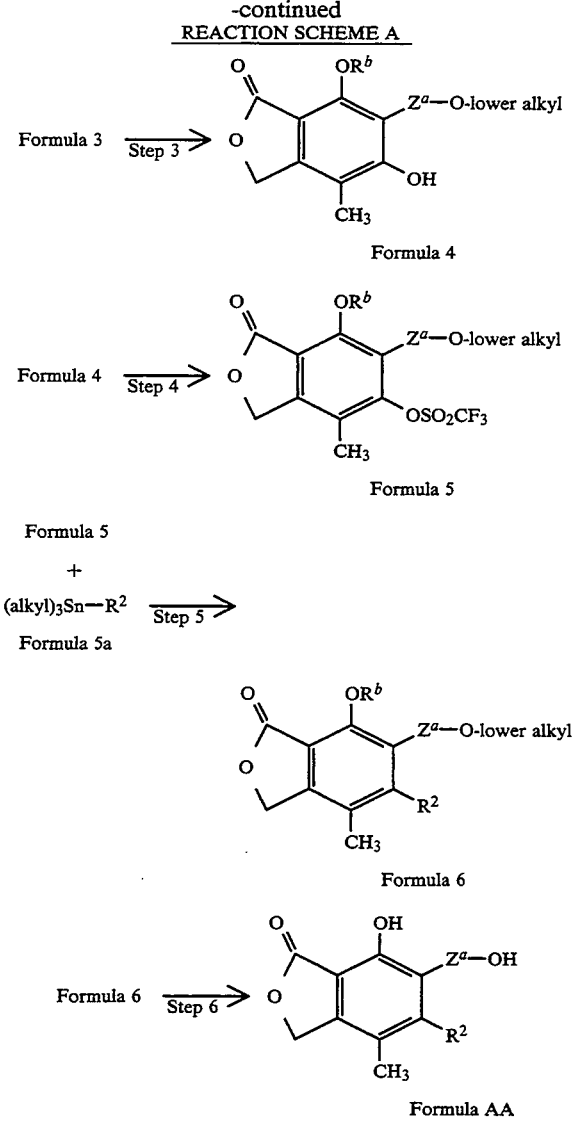

Preparation of Formula 2

As illustrated in Reaction Scheme A, Step 1, a lower alkyl ester of Formula IA, prepared as described above, is protected at the phenolic hydroxyl with an arylsulfonyl or alkylsulfonyl group.

A compound of Formula IA is reacted with 1.0 to 1.1 (preferably 1.05) molar equivalents of an arylsulfonyl or alkylsulfonyl halide (preferably p-toluenesulfonyl chloride) in pyridine. The reaction takes place at −10° C. to 30° C. (preferably room temperature) for 1 to 24 hours (preferably 12 hours). The protected corresponding compound of Formula 2 is isolated by conventional means (such as evaporation).

Preparation of Formula 3

As illustrated in Reaction Scheme A, Step 2, a protected lower alkyl ester of Formula 2 is demethylated in a cleavage reaction with 5 moles of anhydrous lithium iodide in a pyridine solvent (preferably collidine). The reaction takes place at 60° to 75° C. (preferably 60° C.) for 10 hours to 8 days (preferably 4 days). The corresponding protected 6-hydroxy acid of Formula 3 is isolated by conventional means (such as evaporation).

Preparation of Formula 4

As illustrated in Reaction Scheme A, Step 3, a protected 6-hydroxy acid of Formula 3 is esterified in an acid-catalyzed esterification. The reaction takes place in a lower alkanol solvent (corresponding to the desired lower alkyl ester, such as methanol) with an acid (such as p-toluenesulfonic acid) at room temperature for 12 to 24 hours (preferably 18 hours). The corresponding protected 6-hydroxy lower alkyl ester of Formula 4 is isolated and purified by conventional means (such as chromatography).

Preparation of Formula 5

As illustrated in Reaction Scheme A, Step 4, a protected 6-hydroxy lower alkyl ester of Formula 4 is converted to the corresponding 6-triflate. The reaction takes place with the addition of 1.05 to 1.3 (preferably 1.2) molar equivalents of trifluoromethanesulfonic anhydride in a solvent (such as methylene chloride and/or pyridine) at $-10°$ C. to $10°$ C. (preferably $0°$ C.) for 15 minutes to 10 hours (preferably 30 minutes). The corresponding protected 6-triflate is isolated by conventional means (such as evaporation).

Preparation of Trialkylstannanes of Formula 5a

The trialkylstannanes of Formula 5a, which are used in Step 5 of Reaction Scheme A, are prepared as illustrated below, by reaction of an organolithium or organomagnesium (Grignard) reagent with a trialkyl (preferably tributyl) tin chloride. The organolithium or organomagnesium reagents are either commercially available, or are made by conventional methods such as halogen-metal exchange. Compounds in which $R^2$ contains a terminal triple bond, (e.g., where $R^2$ is —C≡CH or —C≡C—CH$_3$) can be reacted directly with butyllithium to afford the organolithium compound $R^2$-Li.

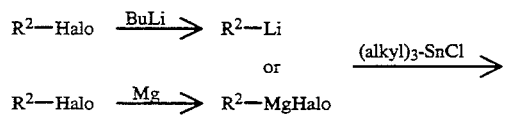

The butyl lithium reaction takes place at $-100°$ C. to $0°$ C. (preferably $-78°$ C.) for 1 to 8 hours (preferably 2 hours) to give the corresponding lithium derivative.

The halide starting material is reacted with magnesium metal in a solvent (preferably THF) under standard Grignard reaction conditions to give the magnesium halide derivative.

The lithium or magnesium halide derivative is reacted with a trialkylchlorostannane (preferably tributylchlorostannane) in an ethereal solvent (preferably THF). The reaction takes place at $-78°$ C. to $0°$ C. for 1 to 4 hours (preferably 2 hours) to give the corresponding trialkylstannane of Formula 5a, which is isolated and used in Reaction Scheme A, Step 5 without further purification.

Tetramethyl, vinyltributyltin and phenyltributyl are all commercially available, e.g., from Aldrich.

Preparation of Formula 6

As illustrated in Reaction Scheme A, Step 5, a protected 6-triflate of Formula 5 is converted to the corresponding compound of Formula 6 where $R^2$ is methyl, cycloalkyl, vinyl, fluorovinyl, difluorovinyl, trifluorovinyl, alkenyl, —C≡C—$R^{11}$, allenyl or CH$_2$—O—(4-methoxybenzyl) by reaction with a trialkylstannane of Formula 5a in the presence of 6 moles of lithium chloride and a palladium catalyst [such as tris(dibenzylidineacetone)dipalladium (O) chloroform adduct, or preferably tetrakis(triphenylphosphine)palladium]. The reaction takes place in a polar aprotic solvent (preferably N-methylpyrrolidinone) at $50°$ C. to $100°$ C. (preferably $80°$ C.) for 3 to 10 hours (preferably 6 hours). The 6-substituted protected lower alkyl ester of Formula 6 is isolated and purified by conventional methods.

The compounds of Formula 6 where $R^2$ is lower alkyl of 2 or more carbon atoms can be made by hydrogenation of the corresponding alkenyl compounds of Formula 6, e.g., as described below in Example 7.

Preparation of Formula AA

As illustrated in Reaction Scheme A, Step 6, a 6-substituted protected lower alkyl ester of Formula 6 is deprotected and converted to the corresponding acid by base hydrolysis. The compound of formula 6 is reacted with 5 moles of a strong base (preferably lithium hydroxide) in an aqueous/lower alkanol solvent (such as methanol:water). The reaction takes place at $50°$ to $70°$ C. (preferably $60°$ C.) for 10 to 24 hours (preferably 16 hours) followed by acidification. The 6-substituted acid of Formula AA is isolated and purified by conventional means.

Preparation of Formula A where $R^2$ is CH$_2$OH and CHO

The compounds of Formula A where $R^2$ is CH$_2$OH and CHO (respectively designated Formulae AB-1 and AB-2) are prepared as described with reference to Reaction Scheme B.

REACTION SCHEME B

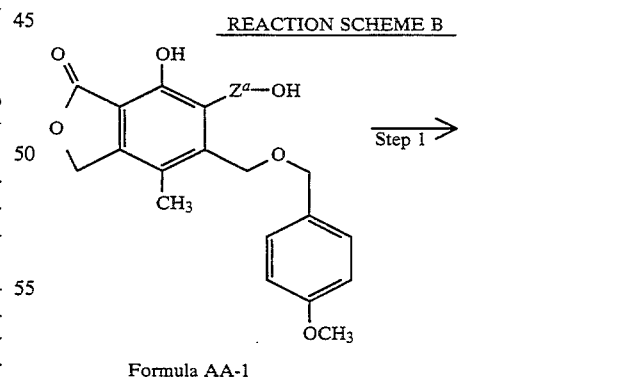

Formula AA-1

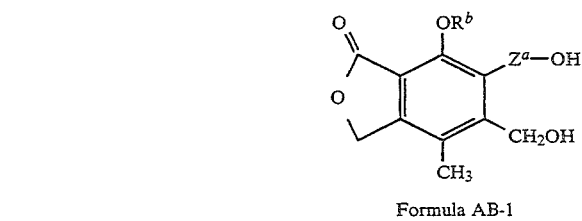

Formula AB-1

-continued
REACTION SCHEME B

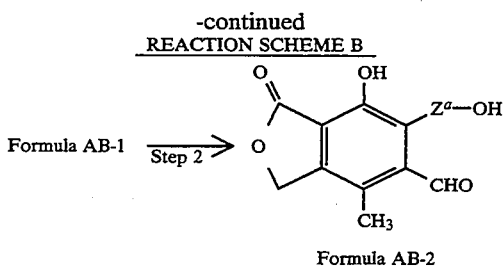

Formula AB-1 →(Step 2) Formula AB-2

Preparation of Formula AB-1

As illustrated in Reaction Scheme B, Step 1, a 6-(4-methoxy)benzyloxymethyl substituted compound of Formula AA (shown as Formula AA-1) is debenzylated by reaction with 1 mole of a Lewis acid (such as boron tribromide or preferably boron trifluoride etherate) or 20 moles of trifluoroacetic acid. The reaction takes place in dichloromethane at −10° C. to 5° C. (preferably 0° C.) for 30 minutes to 2 hours (preferably 1 hour). Alternatively, when using trifluoroacetic acid, the reaction takes place at room temperature. The corresponding 6-hydroxymethyl compound of Formula AB-1 is isolated and purified by conventional means.

Preparation of Formula AB-2

As illustrated in Reaction Scheme B, Step 2, a 6-hydroxymethyl compound of Formula AB-1 is oxidized (using magnesium dioxide or preferably one mole of pyridine chlorochromate). The reaction takes place in methylene chloride at −10° C. to 5° C. (preferably 0° C.) for 8 to 24 hours (preferably 12 hours). The corresponding 6-formyl compound of Formula AB-2 is isolated and purified by conventional means.

Alternative Preparation of Formula A where $R^2$ is Lower Alkyl

A compound of Formula A where $R^2$ is vinyl or alkenyl is converted to the corresponding lower alkyl compound by catalytic reduction in the presence of 0.01 to 0.10 (preferably 0.02) moles of tris(triphenylphosphine)rhodium chloride. The reaction takes place in an inert organic solvent (preferably 1:1 ethanol:benzene) at 20° C. to 30° C. (preferably 25° C.) for 1 to 12 hours (preferably 2 hours). The corresponding compound of Formula A where $R^2$ is lower alkyl (other than methyl) is isolated and purified by conventional means.

Preparation of Formula A where $R^1$ is Acyl

A compound of Formula A, e.g., prepared as described above, is reacted with 1.0 to 1.5 (preferably 1.1) molar equivalents of an acylating agent [such as an acyl halide (e.g., benzoyl chloride) or an acyl anhydride (e.g., acetic anhydride)] in a solvent (such as ether, tetrahydrofuran, or preferably pyridine) optionally in the presence of from 1.0 to 2.0 (preferably 1.25) molar equivalents of an inorganic or organic base (such as sodium carbonate, cesium carbonate or dimethylaminopyridine). The reaction takes place at 0° to 60° C. (preferably 25° C.) for 1 to 12 hours (preferably 2 hours) to afford the corresponding compound of Formula A where $R^1$ is acyl.

Preparation of Formula A where $R^1$ is C(O)—NH-aryl

The compounds of Formula A where $R^1$ is C(O)—NH-aryl are prepared, e.g., as described in previously incorporated U.S. Pat. No. 3,853,919.

Preparation of Esters of Formula A

The esters of Formula A (compounds where G is not OH) can be prepared as described in U.S. Pat. Nos. 4,727,069 and 4,753,935, incorporated herein by reference, or as described below by attachment of a leaving group and its replacement by the desired ester.

Attachment of Leaving Group

A carboxylic acid of Formula A is reacted with from 1.0 to 3.0, preferably about 1.5, molar equivalents of oxalyl chloride or preferably thionyl chloride, in a solvent (such as chloroform or preferably dichloromethane) optionally containing from 0.01 to 0.05 (preferably 0.03) molar equivalents of dimethylformamide. The reaction takes place at −10° to 30° C. (preferably 0° C.) for 1 to 12 hours (preferably 2 hours) to give the corresponding acid chloride (where the leaving group is Cl).

Alternatively, a carboxylic acid of Formula A is reacted with 1.0 to 1.5 (preferably 1.25) molar equivalents of carbonyldiimidazole, in a solvent (such as tetrahydofuran or preferably dichloromethane). The reaction takes place at 0° to 40° C. (preferably 25° C.) for 1 to 12 hours (preferably 2 hours) to give the corresponding acyl imidazole (where the leaving group is 1-imidazolyl).

Esterification

A compound of Formula. A where G has been replaced by a halide or imidazolide is converted to the corresponding alkyl (where G is O-alkyl), thioalkyl (where G is S-alkyl), aminoalkyl (where G is O—(CH$_2$)$_n$—NG$^1$G$^2$) or heterocyclic aminoalkyl (where G is O—(CH$_2$)$_n$—N=G$^3$) compounds, or to the corresponding amides (where G is NG$^1$G$^2$).

A compound of Formula A where G has been replaced by a halide or imidazolide is reacted with from 1.0 to 5.0 (preferably 2) molar equivalents of an alkanol, a thiol or ammonia, a monoalkyl or dialkylamine, or a heterocyclic aminoalkanol, optionally in the presence of from 1.0 to 1.5 (preferably 1.25) molar equivalents of a tertiary organic base (such as 4-dimethylaminopyridine or preferably triethylamine) in an organic solvent (such as dioxane, tetrahydrofuran or preferably dichloromethane). The reaction takes place at −10° to 50° C. (preferably 25° C.) for 1 to 24 hours (preferably 4 hours) to afford the corresponding compound of Formula A where G is other than OH.

Preparation of the Salts of Formula A

Some of the compounds of Formula A can be converted to corresponding acid addition salts. The conversion is accomplished by treatment with a stoichiometric amount of an appropriate acid, such as hydrochloric acid (e.g., 3 molar equivalents to form the trihydrochloride salt). Typically, the free base is dissolved in a polar organic solvent, such as methanol or ethanol, and the acid is added in methanol or ethanol. The temperature is maintained at 0° C. to 50° C. The corresponding salt precipitates spontaneously or can be brought out of solution with a less polar solvent.

The acid addition salts of the compounds of Formula A can be decomposed to the corresponding free bases by treatment with an excess of a suitable base, such as ammonia or sodium bicarbonate, typically in the presence of an aqueous solvent, and at a temperature between 0° C. and 50° C. The free base form is isolated by conventional means, such as extraction with an organic solvent.

Some of the compounds of Formula A can be converted to corresponding base addition salts. The conversion is accomplished by treatment with a stoichiometric amount of an appropriate base, such as sodium carbonate, potassium bicarbonate, lithium hydroxide, ethanolamine, tromethamine, and the like. Typically, the free acid is dissolved in a polar organic solvent, such as methanol or ethanol, and the base is added in water, methanol or ethanol. The temperature is maintained at 0° C. to 50° C. The corresponding salt precipitates spontaneously or can be brought out of solution with a less polar solvent, or the salt can be isolated by evaporation of all solvents, and optionally recrystallizing the residue thus obtained from a suitable solvent, or a mixture of solvents, for example, methanol, ethanol, propanol, ethyl acetate, acetonitrile, tetrahydrofuran, diethyl ether, and the like.

Preferred Processes and Last Steps

A compound of Formula A where $R^1$ is replaced by a protecting group is deprotected.

A compound of Formula A where G is lower alkoxy is hydrolyzed to the corresponding acid where G is OH.

A compound of Formula A where G is OH is esterified to give the corresponding compound where G is lower alkoxy, lower thioalkyl, $NG^1G^2$, $O-(CH_2)_n-NG^1G^2$, or $O-(CH_2)_n-N=G^3$.

A compound of Formula A is contacted with a pharmaceutically acceptable acid or base to form the corresponding acid or base addition salt.

A pharmaceutically acceptable acid addition salt of Formula A is contacted with a base to form the corresponding free base of Formula A.

Preferred Compounds

Generally preferred are the compounds of Formula A where $R^1$ is H, G is OH, and Z is a side chain of Formulae ZA, ZB, ZE, or ZH, particularly those where $R^2$ is lower alkyl, cycloalkyl or vinyl (especially methyl, ethyl, cyclopropyl and vinyl).

Of the compounds of Formula A where Z is a side chain of Formula ZA, preferred are those compounds where $Z^1$ is methyl, $Z^2$ is H or methyl, $Z^3$ is methyl or ethyl, and $Z^4$ is H; particularly the compounds where $Z^2$ and $Z^3$ are methyl, and where $Z^2$ is H and $Z^3$ is methyl or ethyl especially in the (S) configuration.

Of the compounds of Formula A where Z is a side chain of Formula ZB, preferred are those compounds where $D^1-D^2$ is $-CH_2-CH_2-$ or $-CH_2-CH_2-CH_2-$, and $Z^5$ is H, methyl or ethyl; particularly the compounds where $Z^5$ is methyl or ethyl, especially methyl in the (S) configuration.

At present, the most preferred compounds are:
(E) 6-(1,3-dihydro-4-hydroxy-6,7-dimethyl-3-oxoisobenzofuran-5-yl)-4-methyl-4-hexenoic acid;
(E) 6-(1,3-dihydro-6-ethyl-4-hydroxy-7-methyl-3-oxoisobenzofuran-5-yl)-4-methyl-4-hexenoic acid;
(E) 6-(6-cyclopropyl-1,3-dihydro-4-hydroxy-7-methyl-3oxoisobenzofuran-5-yl)-4-methyl-4-hexenoic acid;
(E) 6-(1,3-dihydro-4-hydroxy-7-methyl-3-oxo-6-vinylisobenzofuran-5-yl)-4-methyl-4-hexenoic acid;
(E) 6-(1,3-dihydro-6-ethyl-4-hydroxy-7-methyl-3-oxoisobenzofuran-5-yl)-3,4-dimethyl-4-hexenoic acid; and
(E)-2-[2-[2-[1,3-dihydro-6-ethyl 4-hydroxy-7-methyl-3-oxoisobenzofuran-5-yl]ethylidene]cyclopent-1-yl]acetic acid.

Utility, Testing and Administration

General Utility

The compounds of the present invention, the pharmaceutically acceptable salts thereof and pharmaceutical compositions therewith (collectively the "compounds" for purposes of the following description) are useful as immunosuppressive agents, anti-inflammatory agents, anti-tumor agents, anti-proliferative agents, anti-viral agents and anti-psoriatic agents in mammals, whether domestic (cattle, pigs, sheep, goats, horses), pets (cats, dogs), or preferably humans. The compounds are inhibitors of inosine monophosphate dehydrogenase (IMPDH) and thus inhibit de novo purine synthesis; they have anti-proliferative effects (e.g., against smooth muscle cells and both B and T lymphocytes) and inhibit antibody formation and the glycosylation of cell adhesion molecules in lymphocytes and endothelial cells.

As immunosuppressive agents, the compounds are useful in treating auto-immune related disorders, for example: Type I Diabetes Mellitus; Inflammatory Bowel Disease (e.g., Crohn's Disease and Ulcerative Colitis); Systemic Lupus Erythematosus; Chronic Active Hepatitis; Multiple Sclerosis; Grave's Disease; Hashimoto's Thyroiditis; Behcet's Syndrome; Myasthenia Gravis; Sjogren's Syndrome; Pernicious Anemia; Idiopathic Adrenal Insufficiency; and Polyglandular Autoimmune Syndromes Type I and II.

The compounds are also useful as therapeutic immunosuppressive agents in the treatment of Asthma, Immunohemolytic Anemia, Glomerulonephritis, and Hepatitis. Preventative uses of the compounds as immunosuppressive agents include the treatment of allograft rejection, for example, in cardiac, lung, pancreatic, renal, liver, skin and corneal allografts, and prevention of Graft vs. Host Disease.

The compounds are useful for inhibiting proliferative responses to vascular injury, for example, stenosis following an insult to a blood vessel wall in post-angioplasty restenosis, and post-cardiac by-pass surgery restenosis.

The compounds are useful as anti-inflammatory agents, for example, in treating Rheumatoid Arthritis, Juvenile Rheumatoid Arthritis and Uveitis.

As anti-tumor agents, the compounds are useful in treating solid tumors and malignancies of lymphoreticular origin. For example, the compounds' utility for treatment of solid tumors includes: cancers of the head and neck, including squamous cell carcinoma; lung cancer, including small cell and non-small cell lung carcinoma; mediastinal tumors; esophageal cancer, including squamous cell carcinoma and adenocarcinoma; pancreatic cancer; cancer of the hepatobiliary system, including hepatocellular carcinoma, cholangiocarcinoma, gall bladder carcinoma and biliary tract carcinoma; small intestinal carcinoma, including adenocarcinoma, sarcoma, lymphoma and carcinoids; colorectal cancer, including colon carcinoma and rectal carcinoma; metastatic carcinoma; cancers of the genitourinary system, including ovarian cancer, uterine sarcoma, and renal cell, ureteral, bladder, prostate, urethral, penile, testicular, vulvar, vaginal, cervical, endometrial, and fallopian tube carcinoma; breast cancer; endocrine system cancer; soft tissue sarcomas; malignant mesotheliomas; skin cancer, including squamous cell carcinoma, basal cell carcinoma and melanoma; cancer of the central nervous system; malignant bone tumors; and plasma cell neoplasms.

As anti-tumor agents for the treatment of malignancies of lymphoreticular origin, the compounds are useful in treating, for example: Lymphomas and Leukemias, including B, T and promonocyte cell line malignancies, Mycoses Fungoides, Non-Hodgkins nymphoma, Malignancies of Burkitt Lymphoma Cells and other EBV-transformed B-lymphocytes, Lymphomas resulting from Epstein-Bart viral infections in allograft recipients, Chronic Lymphocytic Leukemia, Acute Lymphocytic Leukemia and Hairy Cell Leukemia.

As anti-viral agents, the compounds are useful in treating, for example: retroviruses, including Human T-leukemia Viruses, Types I and II (HTLV-1 and HTLV-2), Human Immuno Deficiency Viruses, Types I and II (HIV-1, HIV-2) and, Human Nasopharyngeal Carcinoma Virus (NPCV) and in treating Herpes Viruses, including EBV infected B-lymphocytes, CMV infection, Herpes Virus Type 6, Herpes Simplex, Types 1 and 2, (HSV-1, HSV-2) and Herpes Zoster.

As anti-psoriatic agents, the compounds are useful in treating, for example, psoriasis and psoriatic arthritis.

Testing

Activity testing is conducted as described in the following references, and by modifications thereof.

General anti-inflammatory, anti-viral, anti-tumor, anti-psoriatic and/or immunosuppressive activity is associated with the inhibition of Inosine 5'-Monophosphate Dehydrogenase ("IMPDH"). In vitro assays measuring the inhibition of IMPDH, for example, by determining the level of NADH formation according to the method of Anderson, J. H. and Sartorelli, A. C., *J. Biol. Chem.*, 243:4762–4768 (1968) are predictive of such activity.

Initial animal screening tests to determine anti-inflammatory activity potential include the adjuvant arthritis assay, e.g., according to the method of Pearson, *Proc. Soc. Exp. Biol. Med.*, 91:95–101 (1956). Also, in vitro tests, for example those using synovial explants from patients with rheumatoid arthritis, Dayer, et al., *J. Exp. Med.*, 145:1399–1404 (1977), are useful in determining whether compounds exhibit anti-inflammatory activity.

Autoimmune activity is determined, for example, utilizing experimental allergic encephalomyelitis, by a modification of a procedure initially described by Grieg, et. al., *J. Pharmacol. Exp. Ther.*, 173:85 (1970).

Human clinical trials for efficacy in the treatment of asthma are conducted, e.g., as described by Erzurum, Leff, Cochran, et al. "Lack of benefit of methotrexate in severe, steroid-dependent asthma. A double-blind, placebo controlled study." *Ann. Int. Med.*, 114:353–360 (1991).

Activity to prevent the rejection of organ or tissue allografts in experimental animals is determined, for example, as described by Hao, et al., *J. Immunol.*, 139:4022–4026 (1987). In addition, U.S. Pat. No. 4,707,443 and EP 226062, incorporated herein by reference, also describe assays for activity in prevention of allograft rejection by detection of IL-2R levels. Human clinical trials to establish efficacy in preventing rejection of solid organ transplants (such as renal) are conducted, e.g., as described by Lindholm, Albrechtsen, Tufveson, et al., "A randomized trial of cyclosporin and prednisolone versus cyclosporin, azathioprine and prednisolone in primary cadaveric renal transplantation," *Transplantation*, 54:624–631 (1992). Human clinical trials for graft vs. host disease are conducted, e.g., as described by Storb, Deeg, Whitehead, et al., "Methotrexate and cyclosporin compared with cyclosporin alone for prophylaxis of acute graft versus host disease after marrow transplantation for leukemia." *New England J. Med.*, 314:729–735 (1986).

Immunosuppressive activity is determined by both in vivo and in vitro procedures. In vivo activity is determined, e.g., utilizing a modification of the Jerne hemolytic plaque assay, [Jerne, et al., "The agar plaque technique for recognizing antibody producing cells," *Cell-bound Antibodies*, Amos, B. and Kaprowski, H. editors (Wistar Institute Press, Philadelphia) 1963, p. 109]. In vitro activity is determined, e.g., by an adaptation of the procedure described by Greaves, et al., "Activation of human T and B lymphocytes by polyclonal mitogens," *Nature*, 248:698–701 (1974).

Anti-viral activity is determined, for example, by the procedure described by Smee, et al. ["Anti-Herpesvirus Activity of the Acyclic Nucleoside 9-(1,3-Dihydroxy-2-Propoxymethyl)Guanine," *Antimicrobial Agents and Chemotherapy*, 23(5):676–682 (1983)], or as described by Planterose ["Antiviral and cytotoxic effects of mycophenolic acid," *Journal of General Virology*, 4:629 (1969)].

Anti-viral activity can likewise be determined by measurement of reverse transcriptase activity, for example, according to the method described by Chen et al., *Biochem. Pharm.*, 36:4361 (1987).

Human clinical trials for anti-HIV efficacy (together with clinical treatment scenarios) are described and cited, for example, by Sande, et al., "Antiretroviral Therapy for Adult HIV-Infected Patients," *JAMA*, 270(21):2583–2589 (1993). A large scale clinical trial can be conducted, e.g., as described by Volberding, P. A., et al. "Zidovudine in asymptomatic human immunodeficiency virus infection: a controlled trial in persons with fewer than 500 CD4 positive cells per cubic millimeter," *New England J. Med.*, 322(14):941–949 (1990). A smaller scale (Phase I) clinical trial can be conducted, e.g., as described by Browne, et al., "2',3'-Didehydro-3'-deoxythymidine (d4T) in Patients with AIDS or AIDS-Related Complex: A Phase I Trial," *J. Infectious Diseases*, 167:21–29 (1993).

Tests for systemic activity in psoriasis can be carried out, for example, as described by Spatz, et al., "Mycophenolic acid in psoriasis," *British Journal of Dermatology*, 98:429 (1978).

Tests for anti-tumor activity can be performed, for example, as described by Carter, et al. ["Mycophenolic acid: an anticancer compound with unusual properties," *Nature*, 223:848 (1969)].

In vitro activity for treating stenosis is demonstrated, for example, by inhibiting the proliferation of smooth muscle cells, as established by the following human arterial smooth muscle cell proliferation assay. Human smooth muscle cells are grown in culture. A test group is treated with the test compound added at selected concentrations in fresh media. Both groups receive 2 $\mu$Ci tritiated thymidine ($^3$HTdR), a radioisotope label. After 24 hours, the cells are harvested and the amount of label incorporated into DNA is counted by scintillation; this is compared for the test and control groups, the amount being proportional to cell proliferation. Inhibition of smooth muscle proliferation is established when the test group has a lower radioisotope count than the control group. The concentrations of test compound required to inhibit proliferation by 50% (the $IC_{50}$), and to inhibit proliferation by more than 95% are determined.

In vivo activity for treating stenosis is demonstrated, for example, in rat and pig models for arterial stenosis. In the rat model, a test group is treated with the test compound, starting 6 days before and continuing for 14 days after injury to the left carotid artery; the test group is compared to a control group receiving vehicle without the test compound. Injury is achieved by a gentle perfusion of air through a 10 mm long section of the left artery. The right artery is left intact. Arterial cross-sections (10 μm) are taken from both the left and right arteries of each subject, and the area of the vessel wall (endothelium, intima, media) is measured. The amount of vascular proliferation is calculated by subtracting the mean area of the intact, right carotid artery from the mean area of the injured, left carotid artery. Reduction in vascular proliferation is established when the test group shows less proliferation than the control group.

Human clinical trials for restenosis after coronary angioplasty are conducted, e.g., as described by Serruys, Rutsch, Heyndrickx, et al., "prevention of restenosis after percutaneous transluminal coronary antioplasty with thromboxane $A_2$-receptor blockade: a randomozed, double-blind, placebo-controlled trial." *Circulation*, 84:1568–80 (1991).

Administration

The compounds of Formula A are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities. The compounds can be used both prophylactically (e.g., to prevent allograft rejection) and therapeutically.

While human dosage levels have yet to be optimized for the compounds of the invention, generally, a daily dose is from about 0.01 to 100.0 mg/kg of body weight, preferably about 0.1 to 64.3 mg/kg of body weight, and most preferably about 0.3 to 43.0 mg/kg of body weight. Thus, for administration to a 70 kg person, the dosage range would be about 0.7 mg to 7 g per day, preferably about 7.0 mg to 4.5 g per day, and most preferably about 21 mg to 3.0 g per day. The amount of active compound administered will, of course, be dependent on the subject and disease state being treated, the severity of the affliction, the manner and schedule of administration (e.g., oral administration one day prior to cancer chemotherapy and intravenous administration during cancer chemotherapy) and the judgment of the prescribing physician.

In employing the compounds of this invention for treatment of the above conditions, any pharmaceutically acceptable mode of administration can be used. The compounds of Formula A can be administered either alone or in combination with other pharmaceutically acceptable excipients, including solid, semi-solid, liquid or aerosol dosage forms, such as, for example, tablets, capsules, powders, liquids, injectables, suspensions, suppositories, aerosols or the like. The compounds of Formula A can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula A or a pharmaceutically acceptable salt thereof. In addition, these compositions may include other medicinal agents, pharmaceutical agents, carriers, adjuvants, etc., such as multidrug resistance modifying agents, steroids, immunosuppressants such as cyclosporine A, azathioprene, rapamycin, FK-506, brequinar, leflunomide and vincrystine.

Generally, depending on the intended mode of administration, the pharmaceutically acceptable composition will contain about 0.1% to 90%, preferably about 0.5% to 50%, by weight of a compound or salt of Formula A, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable composition is formed by the incorporation of any of the normally employed excipients, such as, for example, mannitol, lactose, starch, povidone, magnesium stearate, sodium saccharine, talcum, cellulose, croscarmellose sodium, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; a disintegrant such as croscarmellose sodium or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from pharmaceutically acceptable carrier may be prepared.

For oral administration, a pharmaceutically acceptable composition is formed by the incorporation of any of the normally employed excipients, such as, for example pharmaceutical grades of mannitol, lactose, starch, magnesium stearate, talcum, povidone, cellulose derivatives, croscarmellose sodium, glucose, sucrose, magnesium carbonate, sodium saccharin, talcum and the like. Such compositions take the form of solutions, suspensions, tablets, capsules, powders, sustained release formulations and the like. Such compositions may contain 0.01%-95% active ingredient, preferably 0.1-50%.

For a solid dosage form containing liquid, the solution or suspension, in for example propylene carbonate, vegetable oils or triglycerides, is preferably encapsulated in a gelatin capsule. Such ester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, polyoxyethylene, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be hitcher if the composition is a solid which will be subsequently diluted to the above percentages. Preferably the composition will comprise 0.2-2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1

1A. Formula 2 where $Z^a$ is a Side Chain of Formula ZA and $Z^1$ is Methyl, $Z^2$, $Z^3$, and $Z^4$ are H, $R^b$ is Tosyl and Lower Alkyl is Methyl p-Toluenesulfonyl chloride (30 g) was added to a solution of methyl (E) 6-(1,3-dihydro-4-hydroxy-6-methoxy-7-methyl-3-oxoisobenzofuran-5-yl)-4-methyl-4-hexenoate (40 g) in pyridine (200 ml) at 0° C. After 6 hours the solution was poured on to ice and acidified to pH 3 with dilute hydrochloric acid. The solution was extracted with ethyl acetate and the extract was dried and evaporated to afford methyl (E) 6-(1,3-dihydro-6-methoxy-7-methyl-3-oxo-4-p-toluenesulfonyloxyisobenzofuran-5-yl)-4-methyl-4-hexenoate.

1B. Formula 2 varying $Z^a$

By following the procedure of part A and substituting methyl (E) 6-(1,3-dihydro-4-hydroxy-6-methoxy-7-methyl-3-oxoisobenzofuran-5-yl)-4-methyl-4-hexenoate with:

methyl (E)-2-[2-[2-[1,3-dihydro-4-hydroxy-6-methoxy-7-methyl-3-oxoisobenzofuran-5-yl]ethylidene]cyclopent-1-yl]acetate;

methyl 3-(1,3-dihydro-4-hydroxy-6-methoxy-7-methyl-3-oxo-5-isobenzofuranylmethyl)-2-methylcyclopent-2-en-1-ylacetate;

ethyl (E)-3-[2-(1,3-dihydro-4-hydroxy-6-methoxy-7-methyl-3-oxoisobenzofuran-5-yl)ethylidene]cyclopentane-1-carboxylate;

methyl (E)-2-[3-(1,3-dihydro-4-hydroxy-6-methoxy-7-methyl-3-oxoisobenzofuran-5-yl)-prop-1-en-1-yl]-3-methylbenzoate;

methyl 4-(1,3-dihydro-4-hydroxy-6-methoxy-7-methyl-3-oxoisobenzofuran-5-ylmethyl)-3-methylcyclopent-3-ene-1-carboxylate;

methyl 3-[3-(1,3-dihydro-4-hydroxy-6-methoxy-7-methyl-3-oxoisobenzofuran-5-yl)cyclopent-1-en-1-yl]-propionate;

methyl (E)-2-[-3-(1,3-dihydro-4-hydroxy-6-methoxy-7-methyl-3-oxoisobenzofuran-5-yl)-1-methylpropenyl]-cyclopentanecarboxylate;

and the compounds of Formula IA where $Z^a$ corresponds to the side chains identified in the following tables:

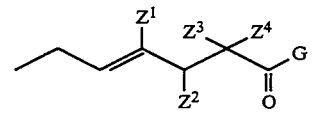

| $Z^1$ | $Z^2$ | $Z^3$ | $Z^4$ | Isomer |
|---|---|---|---|---|
| Methyl | H | H | Methyl | |
| Methyl | Methyl | H | Ethyl | |
| Ethyl | H | H | H | |
| Ethyl | H | H | Methyl | |
| n-Propyl | H | H | Methyl | |
| $CF_3$ | H | H | Methyl | |
| $CF_3$ | H | H | H | |
| H | H | H | H | |
| H | H | H | Methyl | |
| Methyl | Methyl | H | H | |
| H | Methyl | H | Methyl | |
| Methyl | Methyl | H | Methyl | Diastereoisomer A |
| Methyl | Methyl | H | Methyl | Diastereoisomer B |
| Methyl | Methyl | H | Methyl | (+) Single Isomer |
| Methyl | H | H | Methyl | 2-(R) Isomer |
| Methyl | H | H | Methyl | 2-(S) Isomer |
| Methyl | H | H | Ethyl | 2-(S) Isomer |

-continued

| | | | |
|---|---|---|---|
| Methyl | H | H | Vinyl |
| Methyl | H | H | Allyl |
| Methyl | H | H | n-Propyl |
| Methyl | H | H | iso-Propyl |
| Methyl | H | H | Cyclopropyl |
| Methyl | H | H | Cyclopropyl methyl |
| Methyl | H | H | n-Butyl |
| Methyl | H | H | sec-Butyl |
| Methyl | H | H | 2-Methoxy-ethyl |
| Methyl | H | Phenyl | H |
| Methyl | H | Phenyl | Methyl |
| Methyl | H | Methoxy | H |
| Methyl | H | Ethoxy | Ethyl |
| Methyl | H | Methylthio | H |
| Methyl | H | Ethylthio | Methyl |
| Methyl | Methyl | H | H |
| Methyl | Ethyl | H | H |
| H | Ethoxy | H | H |
| Methyl | Ethoxy | Methyl | H |
| Methyl | Ethoxy | H | H |
| Methyl | Ethoxy | H | Phenyl |
| Methyl | Ethoxy | H | Ethyl |
| Ethyl | Methoxy | H | H |
| $CF_3$ | n-Propoxy | H | H |
| Cl | Ethoxy | H | H |
| Ethyl | H | t-Butyl | H | 2-(S) Isomer |
| n-Propyl | H | Methyl | H | 2-(R) Isomer |
| H | H | SO-Methyl | H |
| Methyl | H | SO-Methyl | H |
| Methyl | H | SO-Ethyl | H |
| Methyl | Methyl | SO-Methyl | Methoxy |
| Methyl | Methoxy | SO-Ethyl | Phenyl |
| $CF_3$ | H | SO-t-Butyl | H |
| Cl | H | H | H |
| Fl | H | H | H |
| Cl | H | H | cyclopentyl |
| Methyl | H | Cyclopropyl | |
| Methyl | H | S-Methyl | H |
| n-Propyl | H | S-Propyl | H |
| Methyl | Methyl | S-Ethyl | H |

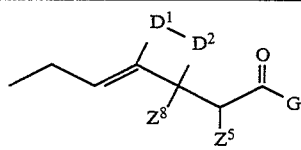

| $D^1$—$D^2$ | $Z^5$ | $Z^8$ | Isomer |
|---|---|---|---|
| $(CH_2)_2$ | H | H | |
| $(CH_2)_4$ | H | H | |
| $(CH_2)_5$ | H | H | |
| $CH_2$—O—$CH_2$ | H | H | |
| $CH_2$—O—$CH_2$ | Methyl | H | 1 (S), 2 (S) Isomer |
| $CH_2$—O—$CH_2$ | Methyl | H | 1 (S), 2 (R) Isomer |
| $(CH_2)_2$—O—$CH_2$ | H | H | (−) Isomer |
| $(CH_2)_2$—O—$CH_2$ | H | H | (+) Isomer |
| $(CH_2)_2$—O—$CH_2$ | H | H | (±) Isomer |
| $CH_2$—S—$CH_2$ | H | Methyl | |
| $CH_2$—NH—$CH_2$ | H | H | |
| $(CH_2)_2$—S(O)—$CH_2$ | H | H | |
| $(CH_2)_2$—O—$CH_2$ | H | Methyl | |
| $(CH_2)_3$—O—$CH_2$ | H | H | |
| $(CH_2)_3$ | Methyl | H | Diastereomer A 1 (S) |
| $(CH_2)_3$ | Methyl | H | Diastereomer B 1 (S) |
| $(CH_2)_3$ | Ethyl | H | 1 (S), 2 (R) Isomer |
| $(CH_2)_3$ | Ethyl | H | 1 (S), 2 (S) Isomer |
| $(CH_2)_3$ | n-Propyl | H | |
| $(CH_2)_4$ | Methyl | H | Diastereomer A |
| $(CH_2)_4$ | Methyl | H | 1 (S), 2 (R) Isomer |
| $(CH_2)_4$ | Methyl | H | Diastereomer B |
| $(CH_2)_4$ | Methyl | H | 1 (S), 2 (S) Isomer |
| $(CH_2)_4$ | Ethyl | Methyl | |
| $(CH_2)_3$ | n-Hexyl | Methyl | |

| $Z^5$ | $Z^6$ | $Z^7$ | Isomer |
|---|---|---|---|
| H | H | H | |
| H | 3-Methyl | H | |
| H | 6-Methyl | H | |
| H | 5-t-Butyl | H | |
| H | 5-Methyl | 6-Methyl | |
| H | 5-Methoxy | H | |
| H | 4-COOH | H | |
| H | 4-Chloro | H | |
| H | 5-Chloro | H | |
| H | 5-Bromo | 6-Bromo | |
| H | 5-Nitro | H | |
| H | 6-Nitro | H | |
| Methyl | H | H | |
| Methyl | 3-Methyl | H | |
| Methyl | 6-Methyl | H | |
| Methyl | 5-t-Butyl | H | |
| Methyl | 5-Methyl | 6-Methyl | |
| Methyl | 5-Methoxy | H | |
| Methyl | 4-COOH | H | |
| Methyl | 4-Chloro | H | |
| Methyl | 5-Chloro | H | |
| Methyl | 5-Bromo | 6-Bromo | |
| Methyl | 6-Nitro | H | |
| n-Propyl | H | H | |
| n-Propyl | 3-Methyl | H | |
| n-Propyl | 6-Methyl | H | |
| n-Propyl | 5-t-Butyl | H | |
| n-Propyl | 5-Methyl | 6-Methyl | |
| n-Propyl | 5-Methoxy | H | |
| n-Propyl | 4-COOH | H | |
| n-Propyl | 4-Chloro | H | |
| n-Propyl | 5-Chloro | H | |
| n-Propyl | 5-Bromo | 6-Bromo | |
| n-Propyl | 6-Nitro | H | |

| $D^4$ | $Z^1$ | Isomer |
|---|---|---|
| $CH_2$ | Hydrogen | |
| O—$CH_2$ | Methyl | |
| $CH_2$ | Ethyl | |
| $CH_2$ | n-Propyl | |
| $(CH_2)_2$ | H | |
| $(CH_2)_2$ | Methyl | |
| $(CH_2)_2$ | Ethyl | |
| $(CH_2)_3$ | H | |
| $(CH_2)_3$ | Methyl | |
| $CH_2$ | $CF_3$ | | there are obtained
methyl (E)-2-[2-[2-[1,3-dihydro-6-methoxy-7-methyl-3-oxo-4-p-toluenesulfonyloxyisobenzofuran-5-yl]ethylidene]cyclopent-1-yl]acetate;
methyl 3-(1,3-dihydro-6-methoxy-7-methyl-3-oxo-4-p-toluenesulfonyloxy-5-isobenzofuranylmethyl)-2-methylcyclopent-2-en-1-ylacetate;

ethyl (E)-3-[2-(1,3-dihydro-6-methoxy-7-methyl-3-oxo-4-p-toluenesulfonyloxyisobenzofuran-5-yl)ethylidene]cyclopentane-1-carboxylate;

methyl (E)-2-[3-(1,3-dihydro-6-methoxy-7-methyl-3-oxo-4-p-toluenesulfonyloxyisobenzofuran-5-yl)-prop-1-en-1-yl]-3-methylbenzoate;

methyl 4-(1,3-dihydro-6-methoxy-7-methyl-3-oxo-4-p-toluenesulfonyloxyisobenzofuran-5-ylmethyl)-3-methylcyclopent-3-ene-1-carboxylate;

methyl 3-[3-(1,3-dihydro-6-methoxy-7-methyl-3-oxo-4-p-toluenesulfonyloxyisobenzo-furan-5-yl)cyclopent-1-en-1-yl]-propionate;

methyl (E)-2-[-3-(1,3-dihydro-6-methoxy-7-methyl-3-oxo-4-p-toluenesulfonyloxyisobenzofuran-5-yl)-1-methylpropenyl]cyclopentanecarboxylate;

and the other corresponding compounds of Formula 2.

EXAMPLE 2

2A. Formula 3 where $Z^a$ is a Side Chain of Formula ZA and $Z^1$ is Methyl, $Z^2$, $Z^3$, and $Z^4$ are H, and $R^b$ is Tosyl A solution of methyl (E) 6-(1,3-dihydro-6-methoxy-7-methyl-3-oxo-4-p-toluenesulfonyloxyisobenzofuran-5-yl)-4-methyl-4-hexenoate (28 g) in 2,4,6-collidine (100 ml) was heated to 65° C. and lithium iodide (50 g) was added. After 3 days the solution was added to ethyl acetate and dilute hydrochloric acid. The organic layer was dried and evaporated to afford (E) 6-(1,3-dihydro-6-hydroxy-7-methyl-3-oxo-4-p-toluenesulfonyloxyisobenzofuran-5-yl)-4-methyl-4-hexenoic acid.

2B. Formula 3 Varying $Z^a$

By following the procedure of part A and substituting methyl (E) 6-(1,3-dihydro-6-methoxy-7-methyl-3-oxo-4-p-toluenesulfonyloxyisobenzofuran-5-yl)-4-methyl-4-hexenoate with:

methyl (E)-2-[2-[2-[1,3-dihydro-6-methoxy-7-methyl-3-oxo-4-p-toluenesulfonyloxyisobenzofuran-5-yl]ethylidene]cyclopent-1-yl]acetate;

methyl 3-(1,3-dihydro-6-methoxy-7-methyl-3-oxo-4-p-toluenesulfonyloxy-5-isobenzofuranylmethyl)-2-methylcyclopent-2-en-1-ylacetate;

ethyl (E)-3-[2-(1,3-dihydro-6-methoxy-7-methyl-3-oxo-4-p-toluenesulfonyloxyisobenzofuran-5-yl)ethylidene]cyclopentane-1-carboxylate;

methyl (E)-2-[3-(1,3-dihydro-6-methoxy-7-methyl-3-oxo-4-p-toluenesulfonyloxyisobenzofuran-5-yl)-prop-1-en-1-yl]-3-methylbenzoate;

methyl 4-(1,3-dihydro-6-methoxy-7-methyl-3-oxo-4-p-toluenesulfonyloxyisobenzofuran-5-ylmethyl)-3-methylcyclopent-3-ene-1-carboxylate;

methyl 3-[3-(1,3-dihydro-6-methoxy-7-methyl-3-oxo-4-p-toluenesulfonyloxyisobenzo-furan-5-yl)cyclopent-1-en-1-yl]propionate;

methyl (E)-2-[-3-(1,3-dihydro-6-methoxy-7-methyl-3-oxo-4-p-toluenesulfonyloxyisobenzofuran-5-yl)-1-methylpropenyl]cyclopentanecarboxylate;

and the other compounds of Formula 2 corresponding to those listed in the tables in Example 1B, there are obtained:

(E)-2-[2-[2-[1,3-dihydro-6-hydroxy-7-methyl-3-oxo-4-p-toluenesulfonyloxyisobenzofuran-5-yl]ethylidene]cyclopent-1-yl]acetic acid;

3-(1,3-dihydro-6-hydroxy-7-methyl-3-oxo-4-p-toluenesulfonyl-oxy-5-isobenzofuranylmethyl)-2-methylcyclopent-2-en-1-ylacetic acid;

(E)-3-[2-(1,3-dihydro-6-hydroxy-7-methyl-3-oxo-4-p-toluenesulfonyloxyisobenzofuran-5-yl)ethylidene]cyclopentane-1-carboxylic acid;

(E)-2-[3-(1,3-dihydro-6-hydroxy-7-methyl-3-oxo-4-p-toluenesulfonyloxyisobenzofuran-5-yl)-prop-1-en-1-yl]-3-methylbenzoic acid;

4-(1,3-dihydro-6-hydroxy-7-methyl-3-oxo-4-p-toluenesulfonyloxyisobenzofuran-5-ylmethyl)-3-methylcyclopent-3-ene-1-carboxylic acid;

3-[3-(1,3-dihydro-6-hydroxy-7-methyl-3-oxo-4-p-toluenesulfonyloxyisobenzo-furan-5-yl)cyclopent-1-en-1-yl]propionic acid;

(E)-2-[-3-(1,3-dihydro-6-hydroxy-7-methyl-3-oxo-4-p-toluenesulfonyloxyisobenzofuran-5-yl)-1-methylpropenyl]cyclopentanecarboxylic acid;

and the other compounds of Formula 3 corresponding to those listed in the tables in Example 1B.

EXAMPLE 3

3A. Formula 4 where $Z^a$ is a Side Chain of Formula ZA and $Z^1$ is Methyl, $Z^2$, $Z^3$, and $Z^4$ are H, and $R^b$ is Tosyl and Lower Alkyl is Methyl A solution of (E) 6-(1,3-dihydro-6-hydroxy-7-methyl-3-oxo-4-p-toluenesulfonyloxyisobenzofuran-5-yl)-4-methyl-4-hexenoic acid (23 g) and p-toluenesulfonic acid (0.8 g) in methanol (150 ml) was stirred for 18 hours then added to water and ethyl acetate. The organic layer was dried and evaporated and the residue was chromatographed on silica gel, eluting with hexane:ethyl acetate: methanol 40:58:2, to afford methyl (E) 6-(1,3-dihydro-6-hydroxy-7-methyl-3-oxo-4-p-toluenesulfonyloxyisobenzofuran-5-yl)-4-methyl-4-hexenoate.

3B. Formula 4 Varying $Z^a$

By following the procedure of part A and substituting (E) 6-(1,3-dihydro-6-hydroxy-7-methyl-3-oxo-4-p-toluenesulfonyloxyisobenzofuran-5-yl)-4-methyl-4-hexenoic acid with:

(E)-2-[2-[2-[1,3-dihydro-6-methoxy-7-methyl-3-oxo-4-p-toluenesulfonyloxyisobenzofuran-5-yl]ethylidene]cyclopent-1-yl]acetic acid;

3-(1,3-dihydro-6-hydroxy-7-methyl-3-oxo-4-p-toluenesulfonyl-oxy-5-isobenzofuranylmethyl)-2-methylcyclopent-2-en-1-ylacetic acid (E)-3-[2-(1,3-dihydro-6-hydroxy-7-methyl-3-oxo-4-p-toluenesulfonyloxyisobenzofuran-5-yl)ethylidene]cyclopentane-1-carboxylic acid;

(E)-2-[3-(1,3-dihydro-6-hydroxy-7-methyl-3-oxo-4-p-toluenesulfonyloxyisobenzofuran-5-yl)-prop-1-en-1-yl]-3-methylbenzoic acid;

4-(1,3-dihydro-6-hydroxy-7-methyl-3-oxo-4-p-toluenesulfonyloxyisobenzofuran-5-ylmethyl)-3-methylcyclopent-3-ene-1-carboxylic acid;

3-[3-(1,3-dihydro-6-hydroxy-7-methyl-3-oxo-4-p-toluenesulfonyloxyisobenzofuran-5-yl)cyclopent-1-en-1-yl]-propionic acid;

(E)-2-[-3-(1,3-dihydro-6-hydroxy-7-methyl-3-oxo-4-p-toluenesulfonyloxyisobenzofuran-5-yl)-1-methylpropenyl]cyclopentanecarboxylic acid;

and the other compounds of Formula 3 corresponding to those listed in the tables in Example 1B, there are obtained:

methyl (E)-2-[2-[2-[1,3-dihydro-6-hydroxy-7-methyl-3-oxo-4-p-toluenesulfonyloxyisobenzofuran-5-yl]ethylidene]cyclopent-1-yl]acetate;

methyl 3-(1,3-dihydro-6-hydroxy-7-methyl-3-oxo-4-p-toluenesulfonyloxy-5-isobenzofuranylmethyl)-2-methylcyclopent-2-en-1-ylacetate;

methyl (E)-3-[2-(1,3-dihydro-6-hydroxy-7-methyl-3-oxo-4-p-toluenesulfonyloxyisobenzofuran-5-yl)ethylidene]cyclopentane-1-carboxylate;

methyl (E)-2-[3-(1,3-dihydro-6-hydroxy-7-methyl-3-oxo-4-p-toluenesulfonyloxyisobenzofuran-5-yl)-prop-1-en-1-yl]-3-methylbenzoate;

methyl 4-(1,3-dihydro-6-hydroxy-7-methyl-3-oxo-4-p-toluenesulfonyloxyisobenzofuran-5-ylmethyl)-3-methylcyclopent-3-ene-1-carboxylate;

methyl 3-[3-(1,3-dihydro-6-hydroxy-7-methyl-3-oxo-4-p-toluenesulfonyloxyisobenzo-furan-5-yl)cyclopent-1-en-1-yl]-propionate;

methyl (E)-2-[-3-(1,3-dihydro-6-hydroxy-7-methyl-3-oxo-4-p-toluenesulfonyloxyisobenzofuran-5-yl)-1-methylpropenyl]cyclopentanecarboxylate;

and the other compounds of Formula 4 corresponding to those listed in the tables in Example 1B.

EXAMPLE 4

4A. Formula 5 where $Z^a$ is a Side Chain of Formula ZA and $Z^1$ is Methyl, $Z^2$, $Z^3$, and $Z^4$ are H, and $R^b$ is Tosyl and Lower Alkyl is Methyl

Trifluoromethanesulfonic anhydride (10.57 g) was added to a solution of methyl (E) 6-(1,3-dihydro-6-hydroxy-7-methyl-3-oxo-4-p-toluenesulfonyloxyisobenzofuran-5-yl)-4-methyl-4-hexenoate in methylene chloride (500 ml) amd pyridine (5 ml) at 0° C. After 6 hours the reaction was added to excess aqueous sodium bicarbonate. The organic solution was dried and evaporated to afford methyl (E) 6-(1,3-dihydro-7-methyl-3-oxo-4-p-toluenesulfonyloxy-6-trifluoromethanesulfonyloxyisobenzofuran-5-yl)-4-methyl-4-hexenoate.

4B. Formula 5 Varying $Z^a$

By following the procedure of part A and substituting methyl (E) 6-(1,3-dihydro-6-hydroxy-7-methyl-3-oxo-4-p-toluenesulfonyloxyisobenzofuran-5-yl)-4-methyl-4-hexenoate with:

methyl (E)-2-[2-[2-[1,3-dihydro-6-hydroxy-7-methyl-3-oxo-4-p-toluenesulfonyloxyisobenzofuran-5-yl]ethylidene]cyclopent-1-yl]acetate;

methyl 3-(1,3-dihydro-6-hydroxy-7-methyl-3-oxo-4-p-toluenesulfonyloxy-5-isobenzofuranylmethyl)-2-methylcyclopent-2-en-1-ylacetate;

methyl (E)-3-[2-(1,3-dihydro-6-hydroxy-7-methyl-3-oxo-4-p-toluenesulfonyloxyisobenzofuran-5-yl)ethylidene]cyclopentane-1-carboxylate;

methyl (E)-2-[3-(1,3-dihydro-6-hydroxy-7-methyl-3-oxo-4-p-toluenesulfonyloxyisobenzofuran-5-yl)-prop-1-en-1-yl]-3-methylbenzoate;

methyl 4-(1,3-dihydro-6-hydroxy-7-methyl-3-oxo-4-p-toluenesulfonyloxyisobenzofuran-5-ylmethyl)-3-methylcyclopent-3-ene-1-carboxylate;

methyl 3-[3-(1,3-dihydro-6-hydroxy-7-methyl-3-oxo-4-p-toluenesulfonyloxyisobenzo-furan-5-yl)cyclopent-1-en-1-yl]propionate;

methyl (E)-2-[-3-(1,3-dihydro-6-hydroxy-7-methyl-3-oxo-4-p-toluenesulfonyloxyisobenzofuran-5-yl)-1-methylpropenyl]cyclopentanecarboxylate;

and the other compounds of Formula 4 corresponding to those listed in the tables in Example 1B, there are obtained:

methyl (E)-2-[2-[2-[1,3-dihydro-7-methyl-3-oxo-4-p-toluenesulfonyloxy-6-trifluoromethanesulfonyloxyisobenzofuran-5-yl]ethylidene]cyclopent-1-yl]acetate;

methyl 3-(1,3-dihydro-7-methyl-3-oxo-4-p-toluenesulfonyl-oxy-6-trifluoromethanesulfonyloxy-5-isobenzofuranylmethyl)-2-methylcyclopent-2-en-1-ylacetate;

methyl (E)-3-[2-(1,3-dihydro-7-methyl-3-oxo-4-p-toluene-sulfonyloxy-6-trifluoromethanesulfonyloxyisobenzofuran-5-yl)ethylidene]cyclopentane-1-carboxylate;

methyl (E)-2-[3-(1,3-dihydro-7-methyl-3-oxo-4-p-toluenesulfonyloxy-6-trifluoromethanesulfonyloxyisobenzofuran-5-yl)-prop-1-en-1-yl]-3-methylbenzoate;

methyl 4-(1,3-dihydro-7-methyl-3-oxo-4-p-toluenesulfonyl-oxy-6-trifluoromethanesulfonyloxyisobenzofuran-5-ylmethyl)-3-methylcyclopent-3-ene-1-carboxylate;

methyl 3-[3-(1,3-dihydro-7-methyl-3-oxo-4-p-toluenesulfonyloxy-6-trifluoromethanesulfonyloxyisobenzoo-5-yl)cyclopent-1-en-1-yl]-propionate;

methyl (E)-2-[-3-(1,3-dihydro-7-methyl-3-oxo-4-p-toluenesulfonyloxy-6-trifluoromethanesulfonyloxyisobenzofuran-5-yl)-1-methylpropenyl]-cyclopentanecarboxylate;

and the other compounds of Formula 5 corresponding to those listed in the tables in Example 1B.

EXAMPLE 5

5A. Formula 6 where $Z^a$ is a Side Chain of Formula ZA and $Z^1$ is Methyl, $Z^2$, $Z^3$, and $Z^4$ are H, and $R^b$ is Tosyl, $R^2$ is Vinyl and Lower Alkyl is Methyl

A mixture of lithium chloride (4.8 g), tris(dibenzylideneacetone)dipalladium (O) chloroform adduct (0.65 g), triphenylarsine (1.6 g) and methyl (E) 6-(1,3-dihydro-7-methyl-3-oxo-4-p-toluenesulfonyloxy-6-trifluoromethanesulfonyloxyisobenzofuran-5-yl)-4-methyl-4-hexenoate (24.2 g) in N-methylpyrrolidinone (220 ml) was heated to 55° C. Vinyltributyltin (15 g) was added. After 3 hours the mixture was added to water (500 ml), potassium fluoride (16 g) and ethyl acetate. The organic solution was dried, filtered through celite and evaporated to afford methyl (E) 6-(1,3-dihydro-7-methyl-3-oxo-4-p-toluenesulfonyloxy-6-vinylisobenzofuran-5-yl)-4-methyl-4-hexenoate.

5B. Formula 6 Varying $Z^a$

By following the procedure of part A and substituting methyl (E) 6-(1,3-dihydro-7-methyl-3-oxo-4-p-toluenesulfonyloxy-6-trifluoromethanesulfonyloxyisobenzofuran-5-yl)-4-methyl-4-hexenoate with:

methyl (E)-2-[2-[2-[1,3-dihydro-7-methyl-3-oxo-4-p-toluenesulfonyloxy-6-trifluoromethanesulfonyloxyisobenzofuran-5-yl]ethylidene]cyclopent-1-yl]acetate;

methyl 3-(1,3-dihydro-7-methyl-3-oxo-4-p-toluenesulfonyl-oxy-6-trifluoromethanesulfonyloxy-5-isobenzofuranylmethyl)-2-methylcyclopent-2-en-1-ylacetate;

methyl (E)-3-[2-(1,3-dihydro-7-methyl-3-oxo-4-p-toluene-sulfonyloxy-6-trifluoromethanesulfonyloxyisobenzofuran-5-yl)ethylidene]cyclopentane-1-carboxylate;

methyl (E)-2-[3-(1,3-dihydro-7-methyl-3-oxo-4-p-toluenesulfonyloxy-6-trifluoromethanesulfonyloxyisobenzofuran-5-yl)-prop-1-en-1-yl]-3-methylbenzoate;

methyl 4-(1,3-dihydro-7-methyl-3-oxo-4-p-toluenesulfonyl-oxy-6-trifluoromethanesulfonyloxyisobenzofuran-5-ylmethyl)-3-methylcyclopent-3-ene-1-carboxylate;

methyl 3-[3-(1,3-dihydro-7-methyl-3-oxo-4-p-toluenesulfonyloxy-6-trifluoromethanesulfonyloxyisobenzo-furan-5-yl)cyclopent-1-en-1-yl]-propionate;

methyl (E)-2-[-3-(1,3-dihydro-7-methyl-3-oxo-4-p-toluenesulfonyloxy-6-trifluoromethanesulfonyloxyisobenzofuran-5-yl)-1-methylpropenyl]-cyclopentanecarboxylate;

and the other compounds of Formula 5 corresponding to those listed in the tables in Example 1B, there are obtained:

methyl (E)-2-[2-[2-[1,3-dihydro-7-methyl-3-oxo-4-p-toluenesulfonyloxy-6-vinylisobenzofuran-5-yl]ethylidene]cyclopent-1-yl]acetate;

methyl 3-(1,3-dihydro-7-methyl-3-oxo-4-p-toluenesulfonyl-oxy-6-vinyl-5-isobenzofuranylmethyl)-2-methylcyclopent-2-en-1-ylacetate;

methyl (E)-3-[2-(1,3-dihydro-7-methyl-3-oxo-4-p-toluenesulfonyloxy-6-vinylisobenzofuran-5-yl)ethylidene]cyclopentane-1-carboxylate;

methyl (E)-2-[3-(1,3-dihydro-7-methyl-3-oxo-4-p-toluenesulfonyloxy-6-vinylisobenzofuran-5-yl)-prop-1-en-1-yl]-3-methylbenzoate;

methyl 4-(1,3-dihydro-7-methyl-3-oxo-4-p-toluenesulfonyl-oxy-6-vinylisobenzofuran-5-ylmethyl)-3-methylcyclopent-3-ene-1-carboxylate;

methyl 3-[3-(1,3-dihydro-7-methyl-3-oxo-4-p-toluenesulfonyloxy-6-vinylisobenzo-furan-5-yl)cyclopent-1-en-1-yl]-propionate;

methyl (E)-2-[-3-(1,3-dihydro-7-methyl-3-oxo-4-p-toluenesulfonyloxy-6-vinylisobenzofuran-5-yl)-1-methylpropenyl]cyclopentanecarboxylate;

and the other compounds of Formula 6 corresponding to those listed in the tables in Example 1B.

5C. Formula 6 Varying $R^2$

By following the procedure of part A and substituting vinyltributyltin with:
methyltributyltin;
cyclopropyltributyltin;
fluorovinyltributyltin;
trifluorovinyltributyltin;
prop-2-enyltributyltin;
ethynyltributyltin;
pent-2-ynyltributyltin;
allyltributyltin; and
4-methoxybenzyloxymethyltributyltin;
there are obtained:

methyl (E) 6-(1,3-dihydro-6,7-dimethyl-3-oxo-4-p-toluenesulfonyloxyisobenzofuran-5-yl)-4-methyl-4-hexenoate;

methyl (E) 6-(6-cyclopropyl-1,3-dihydro-7-methyl-3-oxo-4-p-toluenesulfonyloxyisobenzofuran-5-yl)-4-methyl-4-hexenoate;

methyl (E) 6-(1,3-dihydro-6-fluorovinyl-7-methyl-3-oxo-4-p-toluenesulfonyloxyisobenzofuran-5-yl)-4-methyl-4-hexenoate;

methyl (E) 6-(1,3-dihydro-7-methyl-3-oxo-4-p-toluenesulfonyloxy-6-trifluorovinylisobenzofuran-5-yl)-4-methyl-4-hexenoate;

methyl (E) 6-(1,3-dihydro-7-methyl-3-oxo-4-p-toluenesulfonyloxy-6-(prop-2-enyl)isobenzofuran-5-yl)-4-methyl-4-hexenoate;

methyl (E) 6-(1,3-dihydro-6-ethynyl-7-methyl-3-oxo-4-p-toluenesulfonyloxyisobenzofuran-5-yl)-4-methyl-4-hexenoate;

methyl (E) 6-(1,3-dihydro-7-methyl-3-oxo-4-p-toluenesulfonyloxy-6-(pent-2-ynyl)isobenzofuran-5-yl)-4-methyl-4-hexenoate;

methyl (E) 6-(6-allyl-1,3-dihydro-7-methyl-3-oxo-4-p-toluenesulfonyloxyisobenzofuran-5-yl)-4-methyl-4-hexenoate; and methyl (E) 6-(1,3-dihydro-6-(4-methoxybenzyloxymethyl)-7-methyl-3-oxo-4-p-toluenesulfonyloxyisobenzofuran-5-yl)-4-methyl-4-hexenoate.

5D. Formula 6 Varying $R^2$

By following the procedure of part A and substituting vinyltributyltin with ethyltributyltin, and substituting methyl (E) 6-(1,3-dihydro-7-methyl-3-oxo-4-p-toluenesulfonyloxy-6-trifluoromethanesulfonyloxyisobenzofuran-5-yl)-4-methyl-4-hexenoate with methyl (E) 6-(1,3-dihydro-7-methyl-3-oxo-4-p-toluenesulfonyloxy-6-trifluoromethanesulfonyloxyisobenzofuran-5yl)-3,4-dimethyl-4-hexenoate, there is obtained methyl (E) 6-(1,3-dihydro-6-ethyl-7-methyl-3-oxo-4-p-toluenesulfonyloxyisobenzofuran-5-yl)-3,4-dimethyl-4-hexenoate.

EXAMPLE 6

6A. Formula AA where $Z^a$ is a Side Chain of Formula ZA and $Z^1$ is Methyl, $Z^2$, $Z^3$, and $Z^4$ are H, and $R^2$ is Vinyl A solution of methyl (E) 6-(1,3-dihydro-7-methyl-3-oxo-4-p-toluenesulfonyloxy-6-vinylisobenzofuran-5-yl)-4-methyl-4-hexenoate (0.37 g) and lithium hydroxide (0.4 g) in methanol (6 ml) and water (6 ml) was heated at 62° C. for 15 hours. The reaction was acidified with aqueous sodium hydrogen sulfate and extracted with ethyl acetate. The extract was dried and evaporated and the residue chromatographed on silica gel, eluting with ethyl acetate/hexane/acetic acid to give (E) 6-(1,3-dihydro-4-hydroxy-7-methyl-3-oxo-6-vinylisobenzofuran-5-yl)-4-methyl-4-hexenoic acid, m.p. 148°–149° C. (tert-butylmethyl ether/hexane).

6B. Formula AA Varying $Z^a$

By following the procedure of part A and substituting methyl (E) 6-(1,3-dihydro-7-methyl-3-oxo-4-p-toluenesulfonyloxy-6-vinylisobenzofuran-5yl)-4-methyl-4-hexenoate with:

methyl (E)-2-[2-[2-[1,3-dihydro-7-methyl-3-oxo-4-p-toluenesulfonyloxy-6-vinylisobenzofuran-5-yl]ethylidene]cyclopent-1-yl]acetate;

methyl 3-(1,3-dihydro-7-methyl-3-oxo-4-p-toluenesulfonyl-oxy-6-vinylisobenzofuran-5-ylmethyl)-2-methylcyclopent-2-en-1-ylacetate;

methyl (E)-3-[2-(1,3-dihydro-7-methyl-3-oxo-4-p-toluenesulfonyloxy-6-vinylisobenzofuran-5-yl)ethylidene]cyclopentane-1-carboxylate;

methyl (E)-2-[3-(1,3-dihydro-7-methyl-3-oxo-4-p-toluenesulfonyloxy-6-vinylisobenzofuran-5-yl)-prop-1-en-1-yl]-3-methylbenzoate;

methyl 4-(1,3-dihydro-7-methyl-3-oxo-4-p-toluenesulfonyl-oxy-6-vinylisobenzofuran-5-ylmethyl)-3-methylcyclopent-3-ene-1-carboxylate;

methyl 3-[3-(1,3-dihydro-7-methyl-3-oxo-4-p-toluenesulfonyloxy-6-vinylisobenzofuran-5-yl)cyclopent-1-en-1-yl]-propionate;

methyl (E)-2-[-3-(1,3-dihydro-7-methyl-3-oxo-4-p-toluenesulfonyloxy-6-vinylisobenzofuran-5-yl)-1-methylpropenyl]cyclopentanecarboxylate;

and the other compounds of Formula 6 corresponding to those listed in the tables in Example 1B, there are obtained:

(E)-2-[2-[2-[1,3-dihydro-4-hydroxy-7-methyl-3-oxo-6-vinylisobenzofuran-5-yl]ethylidene]cyclopent-1-yl]acetic acid;

3-(1,3-dihydro-4-hydroxy-7-methyl-3-oxo-6-vinylisobenzofuran-5-ylmethyl)-2-methylcyclopent-2-en-1-ylacetic acid;

(E)-3-[2-(1,3-dihydro-4-hydroxy-7-methyl-3-oxo-6-vinylisobenzofuran-5-yl)ethylidene]cyclopentane-1-carboxylic acid;

(E)-2-[3-(1,3-dihydro-4-hydroxy-7-methyl-3-oxo-6-vinylisobenzofuran-5-yl)-prop-1-en-1-yl]-3-methylbenzoic acid;

4-(1,3-dihydro-4-hydroxy-7-methyl-3-oxo-6-vinylisobenzofuran-5-ylmethyl)-3-methylcyclopent-3-ene-1-carboxylic acid;

3-[3-(1,3-dihydro-4-hydroxy-7-methyl-3-oxo-6-vinylisobenzofuran-5-yl)cyclopent-1-en-1-yl]-propionic acid;

(E)-2-[-3-(1,3-dihydro-4-hydroxy-7-methyl-3-oxo-6-vinylisobenzofuran-5-yl)-1-methylpropenyl]-cyclopentanecarboxylic acid;

and the other compounds of Formula AA where $R^2$ is vinyl, corresponding to those listed in the tables that follow:

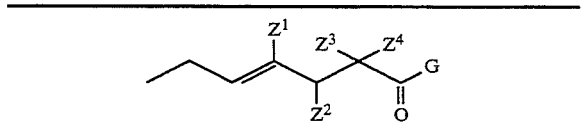

| $Z^1$ | $Z^2$ | $Z^3$ | $Z^4$ | Isomer |
|---|---|---|---|---|
| Methyl | H | H | Methyl | |
| Methyl | Methyl | H | Ethyl | |
| Ethyl | H | H | H | |
| Ethyl | H | H | Methyl | |
| n-Propyl | H | H | Methyl | |
| $CF_3$ | H | H | Methyl | |
| $CF_3$ | H | H | H | |
| H | H | H | H | |
| H | H | H | Methyl | |
| Methyl | Methyl | H | H | |
| H | Methyl | H | Methyl | |
| Methyl | Methyl | H | Methyl | Diastereoisomer A |
| Methyl | Methyl | H | Methyl | Diastereoisomer B |
| Methyl | Methyl | H | Methyl | (+) Single Isomer |
| Methyl | H | H | Methyl | 2-(R) Isomer |
| Methyl | H | H | Methyl | 2-(S) Isomer |
| Methyl | H | H | Ethyl | 2-(S) Isomer |
| Methyl | H | H | Vinyl | |
| Methyl | H | H | Allyl | |
| Methyl | H | H | n-Propyl | |
| Methyl | H | H | iso-Propyl | |
| Methyl | H | H | Cyclopropyl | |
| Methyl | H | H | Cyclopropylmethyl | |
| Methyl | H | H | n-Butyl | |
| Methyl | H | H | sec-Butyl | |
| Methyl | H | H | 2-Methoxyethyl | |
| Methyl | H | Phenyl | H | |
| Methyl | H | Phenyl | Methyl | |
| Methyl | H | Methyoxy | H | |
| Methyl | H | Ethyoxy | Ethyl | |
| Methyl | H | Methylthio | H | |
| Methyl | H | Ethylthio | Methyl | |
| Methyl | Methyl | H | H | |
| Methyl | Ethyl | H | H | |
| H | Ethoxy | H | H | |
| Methyl | Ethoxy | Methyl | H | |
| Methyl | Ethoxy | H | H | |
| Methyl | Ethoxy | H | Phenyl | |
| Methyl | Ethoxy | H | Ethyl | |
| Ethyl | Methoxy | H | H | |
| $CF_3$ | n-Propoxy | H | H | |
| Cl | Ethoxy | H | H | |
| Ethyl | H | t-Butyl | H | 2-(S) Isomer |
| n-Propyl | H | Methyl | H | 2-(R) Isomer |
| H | H | SO-Methyl | H | |
| Methyl | H | SO-Methyl | H | |
| Methyl | H | SO-Ethyl | H | |
| Methyl | Methyl | SO-Methyl | Methoxy | |
| Methyl | Methoxy | SO-Ethyl | Phenyl | |
| $CF_3$ | H | SO-t-Butyl | H | |
| Cl | H | H | H | |
| Fl | H | H | H | |
| Cl | H | H | cyclopentyl | |
| Methyl | H | Cyclopropyl | | |
| Methyl | H | S-Methyl | H | |
| n-Propyl | H | S-Propyl | H | |
| Methyl | Methyl | S-Ethyl | H | |

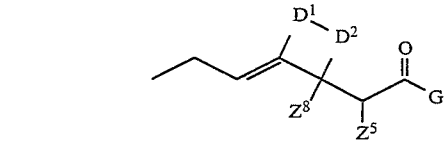

| $D^1-D^2$ | $Z^5$ | $Z^8$ | Isomer |
|---|---|---|---|
| $(CH_2)_2$ | H | H | |
| $(CH_2)_4$ | H | H | |
| $(CH_2)_5$ | H | H | |
| $CH_2-O-CH_2$ | H | H | |
| $CH_2-O-CH_2$ | Methyl | H | 1 (S), 2 (S) Isomer |
| $CH_2-O-CH_2$ | Methyl | H | 1 (S), 2 (S) Isomer |
| $(CH_2)_2-O-CH_2$ | H | H | (−) Isomer |
| $(CH_2)_2-O-CH_2$ | H | H | (+) Isomer |
| $(CH_2)_2-O-CH_2$ | H | H | (±) Isomer |
| $CH_2-S-CH_2$ | H | Methyl | |
| $CH_2-NH-CH_2$ | H | H | |
| $(CH_2)_2-S(O)-CH_2$ | H | H | |
| $(CH_2)_2-O-CH_2$ | H | Methyl | |
| $(CH_2)_3-O-CH_2$ | H | H | |
| $(CH_2)_3$ | Methyl | H | Diastereomer A 1 (S) |
| $(CH_2)_3$ | Methyl | H | Diastereomer B 1 (S) |
| $(CH_2)_3$ | Ethyl | H | 1 (S), 2 (S) Isomer |
| $(CH_2)_3$ | Ethyl | H | 1 (S), 2 (S) Isomer |
| $(CH_2)_3$ | n-Propyl | H | |
| $(CH_2)_4$ | Methyl | H | Diastereomer A |
| $(CH_2)_4$ | Methyl | H | 1 (S), 2 (S) Isomer |
| $(CH_2)_4$ | Methyl | H | Diastereomer B |
| $(CH_2)_4$ | Methyl | H | 1 (S), 2 (S) Isomer |
| $(CH_2)_4$ | Ethyl | Methyl | |
| $(CH_2)_3$ | n-Hexyl | Methyl | |

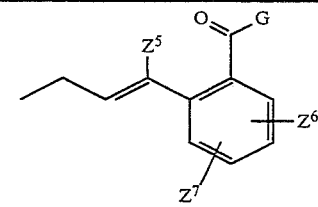

| $Z^5$ | $Z^6$ | $Z^7$ | Isomer |
|---|---|---|---|
| H | H | H | |
| H | 3-Methyl | H | |
| H | 6-Methyl | H | |
| H | 5-t-Butyl | H | |
| H | 5-Methyl | 6-Methyl | |
| H | 5-Methoxy | H | |
| H | 4-COOH | H | |
| H | 4-Chloro | H | |
| H | 5-Chloro | H | |
| H | 5-Bromo | 6-Bromo | |
| H | 5-Nitro | H | |
| H | 6-Nitro | H | |
| Methyl | H | H | |
| Methyl | 3-Methyl | H | |
| Methyl | 6-Methyl | H | |
| Methyl | 5-t-Butyl | H | |
| Methyl | 5-Methyl | 6-Methyl | |
| Methyl | 5-Methoxy | H | |
| Methyl | 4-COOH | H | |
| Methyl | 4-Chloro | H | |
| Methyl | 5-Chloro | H | |

| | | |
|---|---|---|
| Methyl | 5-Bromo | 6-Bromo |
| Methyl | 6-Nitro | H |
| n-Propyl | H | H |
| n-Propyl | 3-Methyl | H |
| n-Propyl | 6-Methyl | H |
| n-Propyl | 5-t-Butyl | H |
| n-Propyl | 5-Methyl | 6-Methyl |
| n-Propyl | 5-Methoxy | H |
| n-Propyl | 4-COOH | H |
| n-Propyl | 4-Chloro | H |
| n-Propyl | 5-Chloro | H |
| n-Propyl | 5-Bromo | 6-Bromo |
| n-Propyl | 6-Nitro | H |

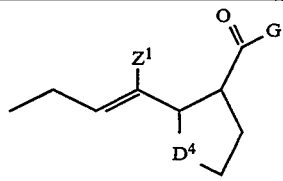

| $D^4$ | $Z^1$ | Isomer |
|---|---|---|
| $CH_2$ | Hydrogen | |
| $O-CH_2$ | Methyl | |
| $CH_2$ | Ethyl | |
| $CH_2$ | n-Propyl | |
| $(CH_2)_2$ | H | |
| $(CH_2)_2$ | Methyl | |
| $(CH_2)_2$ | Ethyl | |
| $(CH_2)_3$ | H | |
| $(CH_2)_3$ | Methyl | |
| $CH_2$ | $CF_3$ | |

6C. Formula AA Varying $R^2$

By following the procedure of part A and substituting methyl (E) 6-(1,3-dihydro-7-methyl-3-oxo-4-p-toluenesulfonyloxy-6-vinylisobenzofuran-5-yl)-4-methyl-4-hexenoate with:

methyl (E) 6-(1,3-dihydro-6,7-dimethyl-3-oxo-4-p-toluenesulfonyloxyisobenzofuran-5-yl)-4-methyl-4-hexenoate;

methyl (E) 6-(1,3-dihydro-6-ethyl-7-methyl-3-oxo-4-p-toluenesulfonyloxyisobenzofuran-5-yl)-4-methyl-4-hexenoate;

methyl (E) 6-(6-cyclopropyl-1,3-dihydro-7-methyl-3-oxo-4-p-toluenesulfonyloxyisobenzofuran-5-yl)-4-methyl-4-hexenoate;

methyl (E) 6-(1,3-dihydro-6-fluorovinyl-7-methyl-3-oxo-4-p-toluenesulfonyloxyisobenzofuran-5-yl)-4-methyl-4-hexenoate;

methyl (E) 6-(1,3-dihydro-7-methyl-3-oxo-4-p-toluenesulfonyloxy-6-trifluorovinylisobenzofuran-5-yl)-4-methyl-4-hexenoate;

methyl (E) 6-(1,3-dihydro-7-methyl-3-oxo-4-p-toluenesulfonyloxy-6-(prop-2-enyl)isobenzofuran-5-yl)-4-methyl-4-hexenoate;

methyl (E) 6-(1,3-dihydro-6-ethynyl-7-methyl-3-oxo-4-p-toluenesulfonyloxyisobenzofuran-5-yl)-4-methyl-4-hexenoate;

methyl (E) 6-(1,3-dihydro-7-methyl-3-oxo-4-p-toluenesulfonyloxy-6-(pent-2-ynyl)isobenzofuran-5-yl)-4-methyl-4-hexenoate;

methyl (E) 6-(6-allyl-1,3-dihydro-7-methyl-3-oxo-4-p-toluenesulfonyloxyisobenzofuran-5-yl)-4-methyl-4-hexenoate; and methyl (E) 6-(1,3-dihydro-6-(4-methoxybenzyloxymethyl)-7-methyl-3-oxo-4-p-toluenesulfonyloxyisobenzofuran-5-yl)-4-methyl-4-hexenoate, there are obtained:

(E) 6-(1,3-dihydro-4-hydroxy-6,7-dimethyl-3-oxoisobenzofuran-5-yl)-4-methyl-4-hexenoic acid, m.p. 167°-170° C. (ethyl acetate);

(E) 6-(1,3-dihydro-6-ethyl-4-hydroxy-7-methyl-3-oxoisobenzofuran-5-yl)-4-methyl-4-hexenoic acid, m.p. 141°-142° C. (t-butylmethyl ether);

(E) 6-(6-cyclopropyl-1,3-dihydro-4-hydroxy-7-methyl-3-oxoisobenzofuran-5-yl)-4-methyl-4-hexenoic acid, m.p. 172°-174° C. (t-butylmethyl ether);

(E) 6-(1,3-dihydro-6-fluorovinyl-4-hydroxy-7-methyl-3-oxoisobenzofuran-5-yl)-4-methyl-4-hexenoic acid;

(E) 6-(1,3-dihydro-4-hydroxy-7-methyl-3-oxo-6-trifluorovinylisobenzofuran-5-yl)-4-methyl-4-hexenoic acid;

(E) 6-(1,3-dihydro-4-hydroxy-7-methyl-3-oxo-6-(prop-2-enyl)isobenzofuran-5-yl)-4-methyl-4-hexenoic acid;

(E) 6-(1,3-dihydro-6-ethynyl-4-hydroxy-7-methyl-3-oxoisobenzofuran-5-yl)-4-methyl-4-hexenoic acid;

(E) 6-(1,3-dihydro-4-hydroxy-7-methyl-3-oxo-6-(pent-2-ynyl)isobenzofuran-5-yl)-4-methyl-4-hexenoic acid;

(E) 6-(6-allyl-1,3-dihydro-4-hydroxy-7-methyl-3-oxoisobenzofuran-5-yl)-4-methyl-4-hexenoic acid; and (E) 6-(1,3-dihydro-4-hydroxy-6-(4-methoxybenzyloxymethyl)-7-methyl-3-oxoisobenzofuran-5-yl)-4-methyl-4-hexenoic acid.

6D. Formula AA Varying $Z^a$ and $R^2$

By following the procedure of part A and substituting methyl (E) 6-(1,3-dihydro-7-methyl-3-oxo-4-p-toluenesulfonyloxy-6-vinylisobenzofuran-5-yl)-4-methyl-4-hexenoate with methyl (E) 6-(1,3-dihydro-6-ethyl-7-methyl-3-oxo-4-p-toluenesulfonyl-oxyisobenzofuran-5-yl)-3,4-dimethyl-4-hexenoate, there is obtained (E) 6-(1,3-dihydro-6-ethyl-4-hydroxy-7-methyl-3-oxoisobenzofuran-5-yl)-3,4-dimethyl-4-hexenoic acid, m.p. 180°-182° C. (acetone/hexane).

EXAMPLE 7

7A. Formula 6 where $Z^a$ is a Side Chain of Formula ZA and $Z^1$ is Methyl, $Z^2$, $Z^3$, and $Z^4$ are H, and $R^b$ is Tosyl, $R^2$ is Ethyl and Lower Alkyl is Methyl A solution of methyl (E) 6-(1,3-dihydro-7-methyl-3-oxo-4-p-toluenesulfonyloxy-6-vinylisobenzofuran-5-yl)-4-methyl-4-hexenoate (17.7 g) and tris(triphenylphosphine)rhodium chloride (1.2 g) in benzene (180 ml) and ethanol (180 ml) was hydrogenated for 11 hours. The solvents were removed under vacuum and the residue was crystallized from ethyl acetate/tert-butyl methyl ether to afford methyl (E) 6-(1,3-dihydro-6-ethyl-7-methyl-3-oxo-4-p-toluenesulfonyloxyisobenzofuran-5-yl)-4-methyl-4-hexenoate, m.p. 101.3°-102.8° C.

7B. Formula 6 Varying $Z^a$

By following the procedure of part A and substituting methyl (E) 6-(1,3-dihydro-7-methyl-3-oxo-4-p-toluenesulfonyloxy-6-vinyl isobenzofuran-5-yl)-4-methyl-4-hexenoate with:

methyl (E)-2-[2-[2-[1,3-dihydro-7-methyl-3-oxo-4-p-toluenesulfonyloxy-6-vinylisobenzofuran-5-yl]ethylidene]cyclopent-1-yl]acetate;

methyl 3-(1,3-dihydro-7-methyl-3-oxo-4-p-toluenesulfonyl-oxy-6-vinylisobenzofuran-5-ylmethyl)-2-methylcyclopent-2-en-1-ylacetate;

methyl (E)-3-[2-(1,3-dihydro-7-methyl-3-oxo-4-p-toluenesulfonyloxy-6-vinylisobenzofuran-5-yl)ethylidene]cyclopentane-1-carboxylate;

methyl (E)-2-[3-(1,3-dihydro-7-methyl-3-oxo-4-p-toluenesulfonyloxy-6-vinylisobenzofuran-5-yl)-prop-1-en-1-yl]-3-methylbenzoate;

methyl 4-(1,3-dihydro-7-methyl-3-oxo-4-p-toluenesulfonyloxy-6-vinylisobenzofuran-5-ylmethyl)-3-methylcyclopent-3-ene-1-carboxylate;

methyl 3-[3-(1,3-dihydro-7-methyl-3-oxo-4-p-toluenesulfonyloxy-6-vinylisobenzofuran-5-yl)cyclopent-1-en-1-yl]-propionate;

methyl (E)-2-[-3-(1,3-dihydro-7-methyl-3-oxo-4-p-toluenesulfonyloxy-6-vinylisobenzofuran-5-yl)-1-methylpropenyl]cyclopentanecarboxylate;

and the other compounds of Formula 6 corresponding to those listed in the tables in Example 1B, there are obtained:

methyl (E)-2-[2-[2-[1,3-dihydro-6-ethyl-7-methyl-3-oxo-4-p-toluenesulfonyloxyisobenzofuran-5-yl]ethylidene]cyclopent-1-yl]acetate;

methyl 3-(1,3-dihydro-6-ethyl-7-methyl-3-oxo-4-p-toluenesulfonyloxyisobenzofuran-5-ylmethyl)-2-methylcyclopent-2-en-1-ylacetate;

methyl (E)-3-[2-(1,3-dihydro-6-ethyl-7-methyl-3-oxo-4-p-toluenesulfonyloxyisobenzofuran-5-yl)ethylidene]-cyclopentane-1-carboxylate;

methyl (E)-2-[3-(1,3-dihydro-6-ethyl-7-methyl-3-oxo-4-p-toluenesulfonyloxyisobenzofuran-5-yl)-prop-1-en-1-yl]-3-methylbenzoate;

methyl 4-(1,3-dihydro-6-ethyl-7-methyl-3-oxo-4-p-toluenesulfonyloxyisobenzofuran-5-ylmethyl)-3-methylcyclopent-3-ene-1-carboxylate;

methyl 3-[3-(1,3-dihydro-6-ethyl-7-methyl-3-oxo-4-p-toluenesulfonyloxyisobenzofuran-5-yl)cyclopent-1-en-1-yl]propionate;

methyl (E)-2-[-3-(1,3-dihydro-6-ethyl-7-methyl-3-oxo-4-p-toluenesulfonyloxyisobenzofuran-5-yl)-1-methylpropenyl]cyclopentanecarboxylate;

and the other compounds of Formula 6 where $R^2$ is ethyl, corresponding to those listed in the tables in Example 1B.

EXAMPLE 8

8A. Formula AA where $Z^a$ is a Side Chain of Formula ZA and $Z^1$ is Methyl, $Z^2$, $Z^3$, and $Z^4$ are H, and $R^2$ is Ethyl A solution of methyl (E) 6-(1,3-dihydro-6-ethyl-7-methyl-3-oxo-4-p-toluenesulfonyloxyisobenzofuran-5-yl)-4-methyl-4-hexenoate (3.16 g) and lithium hydroxide (1.2 g) in 1:1 aqueous methanol (40 ml) was heated at 62° C. for 18 hours. The solution was acidified and extracted with ethyl acetate. The extract was dried and evaporated and the residue chromatographed on silica gel, eluting wth ethyl acetate/hexane/acetic acid to afford (E) 6-(1,3-dihydro-6-ethyl-4-hydroxy-7-methyl-3-oxoisobenzofuran-5-yl)-4-methyl-4-hexenoic acid, m.p. 141°–142° C. (t-butylmethylether).

8B. Formula AA Varying $Z^a$

By following the procedure of part A and substituting methyl (E) 6-(1,3-dihydro-7-methyl-3-oxo-4-p-toluenesulfonyloxy-6-ethylisobenzofuran-5-yl)-4-methyl-4-hexenoate with:

methyl (E)-2-[2-[2-[1,3-dihydro-6-ethyl-7-methyl-3-oxo-4-p-toluenesulfonyloxyisobenzofuran-5-yl]ethylidene]cyclopent-1-yl]acetate;

methyl 3-(1,3-dihydro-6-ethyl-7-methyl-3-oxo-4-p-toluenesulfonyloxy-5-isobenzofuranylmethyl)-2-methylcyclopent-2-en-1-ylacetate;

methyl (E)-3-[2-(1,3-dihydro-6-ethyl-7-methyl-3-oxo-4-p-toluenesulfonyloxyisobenzofuran-5-yl)ethylidene]-cyclopentane-1-carboxylate;

methyl (E)-2-[3-(1,3-dihydro-6-ethyl-7-methyl-3-oxo-4-p-toluenesulfonyloxyisobenzofuran-5-yl)-prop-1-en-1-yl]-3-methylbenzoate;

methyl 4-(1,3-dihydro-6-ethyl-7-methyl-3-oxo-4-p-toluenesulfonyloxyisobenzofuran-5-ylmethyl)-3-methylcyclopent-3-ene-1-carboxylate;

methyl 3-[3-(1,3-dihydro-6-ethyl-7-methyl-3-oxo-4-p-toluenesulfonyloxyisobenzofuran-5-yl)cyclopent-1-en-1-yl]-propionate;

methyl (E)-2-[-3-(1,3-dihydro-6-ethyl-7-methyl-3-oxo-4-p-toluenesulfonyloxyisobenzofuran-5-yl)-1-methylpropenyl]cyclopentanecarboxylate;

and the other compounds of Formula 6 where $R^2$ is ethyl, corresponding to those listed in the tables in Example 1B, there are obtained:

(E)-2-[2-[2-[1,3-dihydro-6-ethyl 4-hydroxy-7-methyl-3-oxoisobenzofuran-5-yl]ethylidene]cyclopent-1-yl]acetic acid, m.p. 168°–169° C. (t-butylmethylether);

3-(1,3-dihydro-6-ethyl-4-hydroxy-7-methyl-3-oxoisobenzofuran-5-ylmethyl)-2-methylcyclopent-2-en-1-ylacetic acid;

(E)-3-[2-(1,3-dihydro-6-ethyl-4-hydroxy-7-methyl-3-oxoisobenzofuran-5-yl)ethylidene]cyclopentane-1-carboxylic acid;

(E)-2-[3-(1,3-dihydro-6-ethyl-4-hydroxy-7-methyl-3-oxoisobenzofuran-5-yl)-prop-1-en-1-yl]-3-methylbenzoic acid;

4-(1,3-dihydro-6-ethyl-4-hydroxy-7-methyl-3-oxoisobenzofuran-5-ylmethyl)-3-methylcyclopent-3-ene-1-carboxylic acid;

3-[3-(1,3-dihydro-6-ethyl-4-hydroxy-7-methyl-3-oxoisobenzofuran-5-yl)cyclopent-1-en-1-yl]-propionic acid;

(E)-2-[-3-(1,3-dihydro-6-ethyl-4-hydroxy-7-methyl-3-oxoisobenzofuran-5-yl)-1-methylpropenyl]-cyclopentanecarboxylic acid;

and the other compounds of Formula AA where $R^2$ is ethyl, corresponding to those listed in the tables that follow:

| $Z^1$ | $Z^2$ | $Z^3$ | $Z^4$ | Isomer |
|---|---|---|---|---|
| Methyl | H | H | Methyl | |
| Methyl | Methyl | H | Ethyl | |
| Ethyl | H | H | H | |
| Ethyl | H | H | Methyl | |
| n-Propyl | H | H | Methyl | |
| $CF_3$ | H | H | Methyl | |
| $CF_3$ | H | H | H | |
| H | H | H | H | |
| H | H | H | Methyl | |
| Methyl | Methyl | H | H | Racemate m.p. 180–182° C. (acetone/hexane) |
| H | Methyl | H | Methyl | |
| Methyl | Methyl | H | Methyl | Diastereoisomer A |
| Methyl | Methyl | H | Methyl | Diastereoisomer B |
| Methyl | Methyl | H | Methyl | (+) Single Isomer |
| Methyl | H | H | Methyl | 2-(R) Isomer |
| Methyl | H | H | Methyl | 2-(S) Isomer |
| Methyl | H | H | Ethyl | 2-(S) Isomer |
| Methyl | H | H | Vinyl | |
| Methyl | H | H | Allyl | |

-continued

| | | | |
|---|---|---|---|
| Methyl | H | H | n-Propyl |
| Methyl | H | H | iso-Propyl |
| Methyl | H | H | Cyclopropyl |
| Methyl | H | H | Cyclopropyl methyl |
| Methyl | H | H | n-Butyl |
| Methyl | H | H | sec-Butyl |
| Methyl | H | H | 2-Methoxyethyl |
| Methyl | H | Phenyl | H |
| Methyl | H | Phenyl | Methyl |
| Methyl | H | Methoxy | H |
| Methyl | H | Ethoxy | Ethyl |
| Methyl | H | Methylthio | H |
| Methyl | H | Ethylthio | Methyl |
| Methyl | Methyl | H | H |
| Methyl | Ethyl | H | H |
| H | Ethoxy | H | H |
| Methyl | Ethoxy | Methyl | H |
| Methyl | Ethoxy | H | H |
| Methyl | Ethoxy | H | Phenyl |
| Methyl | Ethoxy | H | Ethyl |
| Ethyl | Methoxy | H | H |
| $CF_3$ | n-Propoxy | H | H |
| Cl | Ethoxy | H | H |
| Ethyl | H | t-Butyl | H | 2-(S) Isomer |
| n-Propyl | H | Methyl | H | 2-(R) Isomer |
| H | H | SO-Methyl | H |
| Methyl | H | SO-Methyl | H |
| Methyl | H | SO-Ethyl | H |
| Methyl | Methyl | SO-Methyl | Methoxy |
| Methyl | Methoxy | SO-Ethyl | Phenyl |
| $CF_3$ | H | SO-t-Butyl | H |
| Cl | H | H | H |
| Fl | H | H | H |
| Cl | H | H | cyclopentyl |
| Methyl | H | Cyclopropyl | |
| Methyl | H | S-Methyl | H |
| n-Propyl | H | S-Propyl | H |
| Methyl | Methyl | S-Ethyl | H |

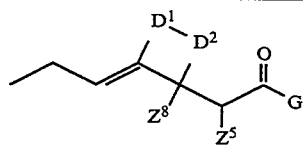

| $D^1$-$D^2$ | $Z^5$ | $Z^8$ | Isomer |
|---|---|---|---|
| $(CH_2)_2$ | H | H | |
| $(CH_2)_4$ | H | H | |
| $(CH_2)_5$ | H | H | |
| $CH_2$—O—$CH_2$ | H | H | |
| $CH_2$—O—$CH_2$ | Methyl | H | 1 (S), 2 (S) Isomer |
| $CH_2$—O—$CH_2$ | Methyl | H | 1 (S), 2 (S) Isomer |
| $(CH_2)_2$—O—$CH_2$ | H | H | (−) Isomer |
| $(CH_2)_2$—O—$CH_2$ | H | H | (+) Isomer |
| $(CH_2)_2$—O—$CH_2$ | H | H | (±) Isomer |
| $CH_2$—S—$CH_2$ | H | Methyl | |
| $CH_2$—NH—$CH_2$ | H | H | |
| $(CH_2)_2$—S(O)—$CH_2$ | H | H | |
| $(CH_2)_2$—O—$CH_2$ | H | Methyl | |
| $(CH_2)_3$—O—$CH_2$ | H | H | |
| $(CH_2)_3$ | Methyl | H | Diastereomer A 1 (S) |
| $(CH_2)_3$ | Methyl | H | Diastereomer B 1 (S) |
| $(CH_2)_3$ | Ethyl | H | 1 (S), 2 (R) Isomer |
| $(CH_2)_3$ | Ethyl | H | 1 (S), 2 (S) Isomer |
| $(CH_2)_3$ | n-Propyl | H | |
| $(CH_2)_4$ | Methyl | H | Diastereomer A |
| $(CH_2)_4$ | Methyl | H | 1 (S), 2 (S) Isomer |
| $(CH_2)_4$ | Methyl | H | Diastereomer B |
| $(CH_2)_4$ | Methyl | H | 1 (S), 2 (S) Isomer |
| $(CH_2)_4$ | Ethyl | Methyl | |

-continued

| | | |
|---|---|---|
| $(CH_2)_3$ | n-Hexyl | Methyl |

[Structure with $Z^5$, $Z^6$, $Z^7$ substituents on benzoate]

| $Z^5$ | $Z^6$ | $Z^7$ | Isomer |
|---|---|---|---|
| H | H | H | |
| H | 3-Methyl | H | |
| H | 6-Methyl | H | |
| H | 5-t-Butyl | H | |
| H | 5-Methyl | 6-Methyl | |
| H | 5-Methoxy | H | |
| H | 4-COOH | H | |
| H | 4-Chloro | H | |
| H | 5-Chloro | H | |
| H | 5-Bromo | 6-Bromo | |
| H | 5-Nitro | H | |
| H | 6-Nitro | H | |
| Methyl | H | H | |
| Methyl | 3-Methyl | H | |
| Methyl | 6-Methyl | H | |
| Methyl | 5-t-Butyl | H | |
| Methyl | 5-Methyl | 6-Methyl | |
| Methyl | 5-Methoxy | H | |
| Methyl | 4-COOH | H | |
| Methyl | 4-Chloro | H | |
| Methyl | 5-Chloro | H | |
| Methyl | 5-Bromo | 6-Bromo | |
| Methyl | 6-Nitro | H | |
| n-Propyl | H | H | |
| n-Propyl | 3-Methyl | H | |
| n-Propyl | 6-Methyl | H | |
| n-Propyl | 5-t-Butyl | H | |
| n-Propyl | 5-Methyl | 6-Methyl | |
| n-Propyl | 5-Methoxy | H | |
| n-Propyl | 4-COOH | H | |
| n-Propyl | 4-Chloro | H | |
| n-Propyl | 5-Chloro | H | |
| n-Propyl | 5-Bromo | 6-Bromo | |
| n-Propyl | 6-Nitro | H | |

[Structure with $Z^1$ and $D^4$ substituents]

| $D^4$ | $Z^1$ | Isomer |
|---|---|---|
| $CH_2$ | Hydrogen | |
| O—$CH_2$ | Methyl | |
| $CH_2$ | Ethyl | |
| $CH_2$ | n-Propyl | |
| $(CH_2)_2$ | H | |
| $(CH_2)_2$ | Methyl | |
| $(CH_2)_2$ | Ethyl | |
| $(CH_2)_3$ | H | |
| $(CH_2)_3$ | Methyl | |
| $CH_2$ | $CF_3$ | |

EXAMPLE 9

9A. Methyl (E) 6-(1,3-dihydro-6-(p-methoxybenzyloxymethyl)-7-methyl-3-oxo-4-p-toluenesulfonyloxyisobenzofuran-5-yl)-4-methyl-4-hexenoate A mixture of lithium chloride (1.6 g), tris(dibenzylideneacetone)dipalladium (O) chloroform adduct (0.22 g), triphenylarsine (0.53 g), methyl (E) 6-(1,3-dihydro-7-methyl-3-oxo-4-p-toluenesulfonyloxy-6-trifluoromethanesulfonyloxyisobenzofuran-5-yl)-4-methyl-4-hexenoate (8.0 g) and N-methylpyrrolidinone (70 ml) is heated to 55° C. p-Methoxybenzyloxymethyltributyltin (7.5 g) is added. After 3 hours the solution is added to water (200 ml), potassium fluoride (5 g) and ethyl acetate (200 ml). The organic solution is dried, filtered through celite and evaporated, and the residue is chromatographed on silica gel, eluting with hexane:ethyl acetate, to afford methyl (E) 6-(1,3-dihydro-6-(p-methoxybenzyloxymethyl)-7-methyl-3-oxo-4-p-toluenesulfonyloxyisobenzofuran-5-yl)-4-methyl-4-hexenoate.

9B. Methyl (E) 6-(1,3-dihydro-6-hydroxymethyl-7-methyl-3-oxo-4-p-toluenesulfonyloxyisobenzofuran-5-yl)-4-methyl-4-hexenoate Methyl (E) 6-(1,3-dihydro-6-(p-methoxybenzyloxymethyl)-7-methyl-3-oxo-4-p-toluenesulfonyloxyisobenzofuran-5-yl)-4-methyl-4-hexenoate (0.5 g) is dissolved in trifluoroacetic acid (10 ml) at 0° C. After 30 minutes the solvent is removed under vacuum and the residue is chromatographed on silica gel, eluting with hexane:ethyl acetate, to afford methyl (E) 6-(1,3-dihydro-6-hydroxymethyl-7-methyl-3-oxo-4-p-toluenesulfonyloxyisobenzofuran-5-yl)-4-methyl-4-hexenoate.

9C. Methyl (E) 6-(1,3-dihydro-6-formyl-7-methyl-3-oxo-4-p-toluenesulfonyloxyisobenzofuran-5-yl)-4-methyl-4-hexenoate Methyl (E) 6-(1,3-dihydro-6-hydroxymethyl-7-methyl-3-oxo-4-p-toluenesulfonyloxyisobenzofuran-5-yl)-4-methyl-4-hexenoate (0.2 g) is dissolved in dichloromethane (10 ml) and pyridinium chlorochromate (0.15 g) is added. After one hour water (25 ml) is added. The organic solution is dried and evaporated and the residue is chromatographed on silica gel, eluting with hexane:ethyl acetate, to afford methyl (E) 6-(1,3-dihydro-6-formyl-7-methyl-3-oxo-4-p-toluenesulfonyloxyisobenzofuran-5-yl)-4-methyl-4-hexenoate.

9D. Formula A where $R^2$ is p-Methoxybenzyloxymethyl, Hydroxymethyl and Formyl

By following the procedure of Example 6 and substituting methyl (E) 6-(1,3-dihydro-7-methyl-3-oxo-4-p-toluenesulfonyloxy-6-trifluoromethanesulfonyloxyisobenzofuran-5-yl)-4-methyl-4-hexenoate with:
methyl (E) 6-(1,3-dihydro-6-(p-methoxybenzyloxymethyl)-7-methyl-3-oxo-4-p-toluenesulfonyloxyisobenzofuran-5-yl)-4-methyl-4-hexenoate;
methyl (E) 6-(1,3-dihydro-6-hydroxymethyl-7-methyl-3-oxo-4-p-toluenesulfonyloxyisobenzofuran-5-yl)-4-methyl-4-hexenoate; and
methyl (E) 6-(1,3-dihydro-6-formyl-7-methyl-3-oxo-4-p-toluenesulfonyloxyisobenzofuran-5-yl)-4-methyl-4-hexenoate,
there are obtained:
(E) 6-(1,3-dihydro-6-(p-methoxybenzyloxymethyl)-7-methyl-3-oxo-4-p-toluenesulfonyloxyisobenzofuran-5-yl)-4-methyl-4-hexenoic acid;
(E) 6-(1,3-dihydro-6-hydroxymethyl-7-methyl-3-oxo-4-p-toluenesulfonyloxyisobenzofuran-5-yl)-4-methyl-4-hexenoic acid; and
(E) 6-(1,3-dihydro-6-formyl-7-methyl-3-oxo-4-p-toluenesulfonyloxyisobenzofuran-5-yl)-4-methyl-4-hexenoic acid.

EXAMPLE 10

(E)-2-{2-[2-[1,3-dihydro-6-ethyl-4-hydroxy-7-methyl-3-oxoisobenzofuran-5-yl]ethylidene]cyclopent-1-(S)-yl}acetic acid 10A. Methyl (E)-6-(1,3-dihydro-6-ethyl-4-hydroxy-7-methyl-3-oxoisobenzofuran-5-yl)-4-methyl-4-hexenoate A solution of (E)-6-(1,3-dihydro-6-ethyl-4-hydroxy-7-methyl-3-oxoisobenzofuran-5-yl)-4-methyl-4-hexenoic acid in methanol (200 ml) was treated with p-toluenesulfonic acid (0.8 g) and stirred at 25° C. for 16 hours. The reaction mixture was cooled to 0° C. Methyl (E)-6-(1,3-dihydro-6-ethyl-4-hydroxy-7-methyl-3-oxoisobenzofuran-5-yl)-4-methyl-4-hexenoate, m.p. 116.5°–117.6, was collected by filtration.

10B. Methyl (E)-6-(4-t-butyldimethylsilyloxy-1,3-dihydro-6-ethyl-7-methyl-3-oxoisobenzofuran-5-yl)-4-methyl-4-hexenoate A solution of methyl (E)-6-(1,3-dihydro-6-ethyl-4-hydroxy-7-methyl-3-oxoisobenzofuran-5-yl)-4-methyl-4-hexenoate (8.61 g) and imidazole (3.5 g) in dimethyl formamide (40 ml) was treated with t-butyldimethylsilyl chloride (4.50 g) and stirred at 25° C. for 14 hours. The reaction mixture was then poured into ice water and extracted with ether. Drying over magnesium sulfate and evaporation gave methyl (E)-6-(4-t-butyldimethylsilyloxy-1,3-dihydro-6-ethyl-7-methyl-3-oxoisobenzofuran-5-yl)-4-methyl-4-hexenoate.

10C. 2-(4-t-Butyldimethylsilyloxy-1,3-dihydro-6-ethyl-7-methyl-3-oxoisobenzofuran-5-yl)-acetaldehyde A solution of methyl (E)-6-(4-t-butyldimethylsilyloxy-1,3-dihydro-6-ethyl-7-methyl-3-oxoisobenzofuran-5-yl)-4-methyl-4-hexenoate (10.6 g) in methylene chloride (150 ml), methanol (150 ml) and pyridine (5 ml) was treated with an excess of Oxone ® at −70° C. The reaction was quenched with dimethylsulfide (20 ml) and stirred for 5 hours at 25° C. The reaction mixture was poured into 1N aqueous sodium hydrogen sulfate. Extraction with 1:1 ethyl acetate:hexane gave an oil which on purification by silica gel chromatography gave 2-(4-t-butyldimethylsilyloxy-1,3-dihydro-6-ethyl-7-methyl-3-oxoisobenzofuran-5-yl)-acetaldehyde, m.p. 90.9°–91.6° C.

10D. dl-1-[2-(4-t-Butyldimethylsilyloxy-1,3-dihydro-6-ethyl-7-methyl-3-oxoisobenzofuran-5-yl)-1-hydroxy-1-yl]cyclopent-1-ene A solution of 1-bromocyclopentene (21.4 g) in tetrahydrofuran (100 ml) was added over 30 minutes to magnesium (3.62 g) in tetrahydrofuran (30 ml). The reaction mixture was refluxed for 15 minutes and then diluted with tetrahydrofuran so that the final volume was 200 ml. This Grignard reagent (31 ml) was then added to a solution of 2-(4-t-butyldimethylsilyloxy-1,3-dihydro-6-ethyl-7-methyl-3-oxoisobenzofuran-5-yl)-acetaldehyde in tetrahydrofuran (100 ml) at −65° C. After 40 minutes the reaction mixture was poured into aqueous ammonium chloride. Extraction with ether gave an oil which was recrystalized from t-butylmethyl ether/hexane to give dl-1-[2-(4-t-butyldimethylsilyloxy-1,3-dihydro-6-ethyl-7-methyl-3-oxoisobenzofuran-5-yl)-1-hydroxy-1-yl]cyclopent-1-ene, m.p. 129.5°–132° C.

10E. Cyclopentyl (4-t-butyldimethylsilyloxy-1,3-dihydro-6-ethyl-7-methyl-3-oxoisobenzofuran-5-yl methyl)methanone A solution of dimethyl sulfoxide (3 ml) in methylene chloride (100 ml) was cooled to −60° C. and treated with trifluoroacetic anhydride (4 ml). dl-1-[2-(4-t-Butyldimethylsilyloxy-1,3-dihydro-6-ethyl-7-methyl-3-oxoisobenzofuran-5-yl)-1-hydroxy-1-yl]cyclopent-1-ene (4.1 g) in methylene chloride (14 ml) was added over 5 minutes and the reaction mixture was stirred at −60° C. for 1 hour. Triethylamine (11 ml) was added and the reaction mixture was allowed to warm to 20° C. Aqueous workup and extraction with methylene chloride gave an oil which was crystalized from t-butylmethyl ether to give cyclopentyl (4-t-butyl-dimethylsilyloxy-1,3-dihydro-6-ethyl-7-methyl-3-oxoisobenzofuran-5-yl methyl)methanone, m.p. 128.2°–129.4° C.

10F. (S)-2-(4-t-Butyldimethylsilyloxy-1,3-dihydro-6-ethyl-7-methyl-3-oxoisobenzofuran-5-yl)-1-cyclopentenyl-1-hydroxyethane Cyclopentyl (4-t-butyldimethylsilyloxy-1,3-dihydro-6-ethyl-7-methyl-3-oxoisobenzofuran-5-yl methyl)methanone (4.2 g) was treated with a 1M toluene solution of (R)-tetrahydro-1-methyl-3,3-diphenyl-1H,3H-pyrrolo[1,2-c][1,3,2]oxazaborole (3 ml). The toluene was evaporated in vacuo and methylene chloride added (2 ml). The reaction mixture was cooled to −30° C. and borane/dimethyl sulfide (0.33 ml) was added three times at 45 minute intervals. The reaction mixture was stirred 16 hours at −30° C. and quenched by addition of 1M hydrogen chloride/ether (3 ml). Toluene was added (10 ml) and the solution filtered, diluted with ether (200 ml), washed with aqueous hydrochloric acid, aqueous sodium bicarbonate and brine. Drying and evaporation gave an oil which was purified by silica gel chromatography to give (S)-2-(4-t-butyldimethylsilyloxy-1,3-dihydro-6-ethyl-7-methyl-3-oxoisobenzofuran-5-yl)-1-cyclopentenyl-1-hydroxyethane. Further purification by crystallization from t-butylmethyl ether gave material with an enantiomeric excess of 97.8% (Chiracel OD-H, 85:15 hexane:i-propanol, 0.8 ml/minute, minor 8.3 minutes, major 9.2 minutes).

10G. Ethyl (S)(E)-2-{2-[2-(4-t-butyldimethylsilyloxy-1,3-dihydro-6-ethyl-7-methyl-3-oxoisobenzofuran-5-yl)ethylidene]cyclopent-1-yl}acetate A mixture of (S)-2-(4-t-butyldimethylsilyloxy-1,3-dihydro-6-ethyl-7-methyl-3-oxoisobenzofuran-5-yl)-1-cyclopentenyl-1-hydroxyethane (2.8 g), pivalic acid (0.1 g) and triethyl orthoacetate (125 ml) was heated to 138° C. After 2.5 hours, more pivalic acid (65 mg) was added and the reaction was continued 1 hour more. The reaction mixture was cooled, the excess triethyl orthoacetate removed in vacuo, and the residue chromatographed on silica gel (20% ethyl acetate/hexane) to give ethyl (S)(E)-2-{2-[2-(4-t-butyldimethylsilyloxy-1,3-dihydro-6-ethyl-7-methyl-3-oxoisobenzofuran-5-yl)ethylidene]cyclopent-1-yl}acetate.

10H. Ethyl (S)(E)-2-{2-[2-(1,3-dihydro-6-ethyl-4-hydroxy-7-methyl-3-oxoisobenzofuran-5-yl)ethylidene]cyclopent-1-yl}acetate A solution of ethyl (S)(E)-2-{2-[2-(4-t-butyldimethylsilyloxy-1,3-dihydro-6-ethyl-7-methyl-3-oxoisobenzofuran-5-yl)ethylidene]cyclopent-1-yl}acetate (1.24 g) in tetrahydrofuran (8 ml) was cooled to 0° C. and treated with 1M tetrabutylammonium fluoride in tetrahydrofuran (3 ml). After 5 minutes, the reaction mixture was poured into ice water and extracted with ethyl acetate. The extracts were dried, evaporated and the residue chromatographed on silica gel (20% ethyl acetate/hexane) to give ethyl (S)(E)-2-{2-[2-(1,3-dihydro-6-ethyl-4-hydroxy-7-methyl-3-oxoisobenzofuran-5-yl)ethylidene]cyclopent-1-yl}acetate, m.p. 95.0°–95.7° C.

10I. (S)(E)-2-{2-[2-(1,3-Dihydro-6-ethyl-4-hydroxy-7-methyl-3-oxoisobenzofuran-5-yl)ethylidene]cyclopent-1-yl}acetic acid A mixture of ethyl (S)(E)-2-{2-[2-(1,3-dihydro-6-ethyl-4-hydroxy-7-methyl-3-oxoisobenzofuran-5-yl)ethylidene]cyclopent-1-yl}acetate (0.4 g) in methanol (20 ml) and water (20 ml) was treated with lithium hydroxide (1.6 g). The reaction mixture was heated at 65° C. for 2 hours and then cooled. The methanol was removed in vacuo and the residue treated with excess 1M sodium hydrogen sulfate. Extraction with ethyl acetate followed by drying and evaporation gave a residue which was recrystalized from t-butylmethyl ether to give (S)(E)-2-{2-[2-(1,3-dihydro-6-ethyl-4-hydroxy-7-methyl-3-oxoisobenzofuran-5-yl)ethylidene]cyclopent-1-yl}acetic acid, m.p. 168.2°–169.3° C. with an enantiomeric excess of 96.4% (Chiracel AD, 85:15 hexane:i-propanol, 0.1% trifluoroacetic acid, 0.8 ml/minute, minor 12.6 minutes, major 13.5 minutes).

EXAMPLES 11-16

These examples illustrate the preparation of a representative pharmaceutical formulations containing an Active Compound of Formula A, e.g., (E)-6-(1,3-dihydro-4-hydroxy-6-vinyl-7-methyl-3-oxoisobenzofuran-5-yl)-4-methyl-4-hexenoic acid. Other compounds of Formula A, such as those prepared in accordance with Examples 1 through 10, can be used as the Active Compound in preparation of the formulations of these examples.

EXAMPLE 11

This example illustrates the preparation of a representative pharmaceutical formulation for oral administration.

| Ingredients | Quantity per capsule, mgs. |
| --- | --- |
| Active compound | 200 |
| lactose, spray-dried | 148 |
| magnesium stearate | 2 |

The above ingredients are mixed and introduced into a hard-shell gelatin capsule.

EXAMPLE 12

This example illustrates the preparation of another representative pharmaceutical formulation for oral administration.

| Ingredients | Quantity per tablet, mgs. |
| --- | --- |
| Active compound | 400 |
| cornstarch | 50 |
| croscarmellose sodium | 25 |
| lactose | 120 |
| magnesium stearate | 5 |

The above ingredients are mixed intimately and pressed into single scored tablets.

EXAMPLE 13

A suspension for oral administration is prepared having the following composition:

| Ingredients | Amount |
| --- | --- |
| Active compound | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |

-continued

| Ingredients | Amount |
| --- | --- |
| distilled water | q.s. to 100 ml |

EXAMPLE 14

An injectable preparation buffered to a suitable pH is prepared having the following composition:

| Ingredients | Amount |
| --- | --- |
| Active compound | 0.2 g |
| Sodium Acetate Buffer Solution (0.4 M) | 2.0 ml |
| HCl (1N) or NaOH (1N) | q.s. to suitable pH |
| water (distilled, sterile) | q.s. to 20 ml |

EXAMPLE 15

This example illustrates the preparation of a representative pharmaceutical formulation for topical application.

| Ingredients | grams |
| --- | --- |
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C.–70° C. with stirring. A sufficient quantity of water at 60° C. is then added with vigorous stirring to emulsify the ingredients, and water then added q.s. 100 g.

EXAMPLE 16

A suppository totalling 2.5 grams is prepared having the following composition:

| Active compound | 500 mg |
| --- | --- |
| witepsol H-15* | balance |

(*triglycerides of saturated vegetable fatty acid; a product of HULS, Inc., New Jersey).

EXAMPLE 17

In Vitro Determination of Therapeutic Activity (As an Anti-Inflammatory, Anti-Viral, Anti-Tumor, Anti-Psoriatic and/or Immunosuppressive Agent) Utilizing the Inhibition of IMP Dehydrogenase Assay This assay is a modification of the method of Anderson, J. H. and Sartorelli, A. C., Jour. Biol. Chem., 243:4762–4768 (1968). It measures the formation of NADH ($\lambda_{max}$=340 nm, $\epsilon340$=6,220 $M^{-1}cm^{-1}$) as Inosine 5′-monophosphate ("IMP") is converted to Xanthosine 5′-monophosphate ("XMP") by the human Type II IMP dehydrogenase ("IMPDH").

Compounds are dissolved and diluted in DMSO, and reaction solutions containing compounds at 0, 0.01, 0.10, 1.0, 10, and 100 $\mu M$ are prepared in disposable methacrylic plastic microcurers ('UV-transparent' plastic, 1 cm pathlength, 1.5 ml capacity). The solutions (0.5–1 ml) contain the following: 0.1M TrisHCL, pH 8.0; 0.1M KCL; 3.0 mM EDTA; 100 $\mu g/ml$ BSA; 0.05 mM IMP; 0.10 mM NAD; 10% DMSO; 5–15 nM IMPDH (0.003–0.010 units/ml; one unit of enzyme catalyzes the formation of one $\mu mol$ NADH per minute at 40° C. at saturating substrate concentrations—200 $\mu M$ IMP and 400 $\mu M$ NAD). Reactions are performed at 40° C. and initiated by the addition of enzyme. Mycophenolic acid ($IC_{50} \approx 0.02$ $\mu M$) serves as the positive control. The reactions are monitored at 340 nm for 10 minutes in a UV/VIS spectrophotometer, and rate data are collected.

The 50% inhibitory value ("$IC_{50}$") is determined by fitting the fractional activities relative to control to the following equation on a Macintosh computer by the program Systat:

$$\text{Fractional activity} = MAX/((X/IC_{50})^n + 1).$$

X is the concentration of the compound, and the term n accounts for deviations of the data from a simple competitive inhibition model.

The compounds of the present invention inhibit IMPDH when tested by this method, indicating their activity as anti-inflammatory, anti-viral, anti-tumor, anti-psoriatic and/or immunosuppressive agents.

EXAMPLE 18

In Vitro Determination of Immunosuppressive Activity Utilizing Responses of Human Peripheral Blood Lymphocytes to Phytohemagglutinin (PHA)

This procedure is a modification of a procedure initially described by Greaves, et al. ["Activation of human T and B lymphocytes by polyclonal mitogens," Nature, 248:698–701 (1974)].

Human mononuclear cells ("PBL") are separated from heparinized whole blood by density gradient centrifugation in Ficoll-Plaque (Pharmacia). After washing, $2 \times 10^5$ cells/well are cultured in microtiter plates with RPMI 1640 supplemented with 5% fetal calf serum, penicillin and streptomycin. PHA (Sigma) at 10 $\mu g/ml$ is then added. Test materials are tested at concentrations between $10^4$ and $10^8 M$, by addition to the culture at time 0. Cultures are set up in quadruplicate and incubated at 37° C. in a humidified atmosphere with 7% $CO_2$ for 72 hours. A pulse of 0.5 $\mu Ci$/well of $^3H$-thymidine is added for the last 6 hours. Cells are collected on glass fiber filters with an automatic harvester and radioactivity is measured by standard scintillation procedures. The 50% inhibitory concentration ("$IC_{50}$") for mitogenic stimulation is determined graphically.

To evaluate differential effects on T- and B-lymphocytes, different mitogens are used: PWM (Sigma) at 20 $\mu g/ml$ and Staphylococcus Protein A bound to Sepharose (SPA) (Sigma) 2 mg/ml or 14 $\mu g/ml$ of Protein A.

The compounds of the present invention show immunosuppressive activity when tested by this method.

EXAMPLE 19

In Vivo Determination of Immunosuppressive Activity Utilizing the Hemolytic Plaque Forming Cell Assay This procedure is a modification of "The agar plaque technique for recognizing antibody producing cells," a procedure initially described by Jerne et al., [Cellbound Antibodies, Amos and Kaprowski editors (Wistar Institute Press, Philadelphia, 1963), p. 109].

Groups of 5-6 adult C578B1/6 male mice were sensitized with $1 \times 10^8$ sheep red blood cells ("SRBC") and simultaneously treated with an oral dosage form of the test material in an aqueous vehicle. Animals in a control group receive the same volume of vehicle. Four days after SRBC inoculation, spleens are dispersed in loose Ten Broeck homogenizers. The number of nucleated cells ("WBC") is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells ("PFC") are counted with a dissecting microscope. Total WBC/spleen, PFC/spleen and PFC/$10^6$ WBC ("PPM") are calculated for each mouse spleen. Geometric means of each treatment group are then compared with the vehicle-treated control group.

The compounds of the present invention show immunosuppressive activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All of the patents and publications referenced above are hereby incorporated by reference.

What is claimed is:

1. A compound of the formula:

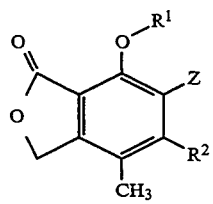

Formula A wherein:

$R^1$ is H or C(O)$R^{10}$, where $R^{10}$ is lower alkyl, aryl or NH-aryl;

$R^2$ is lower alkyl, cycloalkyl, vinyl, fluorovinyl, difluorovinyl, trifluorovinyl, alkenyl, —C≡C—$R^{11}$, allenyl, CHO or CH$_2$O$R^{12}$, where $R^{11}$ is H or lower alkyl, and $R^{12}$ is H or 4-methoxybenzyl; and Z is a side chain selected from Formulae ZA, ZB, ZC, ZD, ZE, ZF, ZG and ZH:

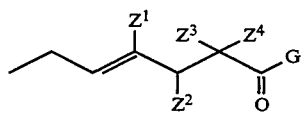

Formula ZA wherein:

$Z^1$ is H, lower alkyl, halo or CF$_3$;

$Z^2$ is H, lower alkyl, lower alkoxy, aryl, or CH$_2$—$Z^{11}$, where $Z^{11}$ is halo, CN, aryl or heteroaryl;

$Z^3$ is H, lower alkyl, lower alkenyl, lower alkoxy, phenyl, or S(O)$_m$-lower alkyl, where m is 0, 1 or 2;

$Z^4$ is H, lower alkyl, halo, or phenyl;

or $Z^3$ and $Z^4$ taken together with the carbon to which they are attached form cycloalkyl of three to five carbon atoms; and G is OH, lower alkoxy, lower thioalkyl, N$G^1G^2$, O—(CH$_2$)$_n$—N$G^1G^2$, or O—(CH$_2$)$_n$—N=$G^3$, where n is an integer from 1 to 6, $G^1$ is H or lower alkyl, $G^2$ is H or lower alkyl, and =$G^3$ is lower alkylene of four to six carbon atoms, or lower alkylene of three to five carbon atoms plus one member that is —O—, —S—, or —N($G^4$)— where $G^4$ is H or lower alkyl; or

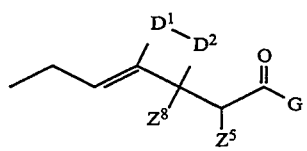

Formula ZB wherein:

$Z^5$ is H or lower alkyl;

$Z^8$ is H, lower alkyl or forms a double bond with $D^2$;

$D^1$ and $D^2$ together with their adjacent carbon atoms form an optionally substituted, saturated or unsaturated carbocyclic or heterocyclic ring of 3 to 7 atoms; and G is as defined above; or

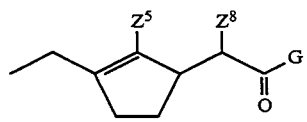

Formula ZC wherein:

$Z^8$ is H or lower alkyl; and $Z^5$ and G are as defined above; or

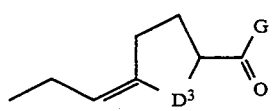

Formual ZD wherein:

$D^3$ is —CH$_2$— or —CH$_2$—CH$_2$—; and

G is as defined above; or

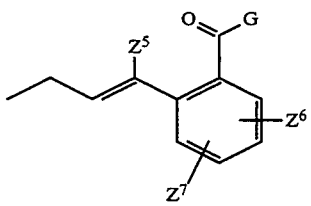

Formula ZE wherein:

$Z^6$ is H, lower alkyl, COOH, NH$_2$, azido or halo;

$Z^7$ is H, lower alkyl or halo; and $Z^5$ and G are as defined above; or

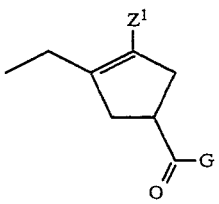

Formula ZF wherein:

Z¹ and G are as defined above; or

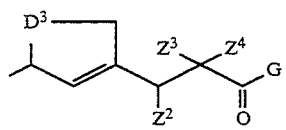

Formula ZG wherein:

$D^3$, $Z^2$, $Z^3$, $Z^4$ and G are as defined above; or

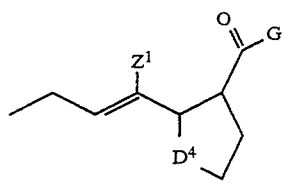

Formula ZH wherein:

$D^4$ is —CH₂—, —CH₂—CH₂—, —CH₂—CH₂—CH₂—, —O—, or —O—CH₂—; and $Z^1$ and G are as defined above;

or a pharmaceutically acceptable salt thereof.

2. The compound or salt of claim 1 wherein Z is selected from Formulae ZA, ZB, ZE and ZH.

3. The compound or salt of claim 1 wherein $R^1$ is H.

4. The compound or salt of claim 3 wherein G is OH.

5. The compound or salt of claim 4 where $R^2$ is methyl, ethyl, vinyl or cyclopropyl.

6. The compound or salt of claim 3 wherein G is morpholinoethoxy.

7. The compound or salt of claim 1 comprising a single enantiomer, a diastereomer, a racemic mixture or a non-racemic mixture.

8. The compound or salt of claim 4 wherein Z is a side chain of Formula ZA.

9. The compound or salt of claim 8 wherein: $Z^1$ is lower alkyl; $Z^2$ is H or lower alkyl; $Z^3$ is H or lower alkyl; and $Z^4$ is H.

10. The compound or salt of claim 9 wherein $Z^1$ is methyl.

11. The compound or salt of claim 10 wherein $Z^2$ is methyl and $Z^3$ is H.

12. The compound or salt of claim 11 wherein $R^2$ is ethyl.

13. The compound or salt of claim 9 wherein $Z^2$ and $Z^3$ are H.

14. The compound or salt of claim 13 wherein $R^2$ is methyl.

15. The compound or salt of claim 13 wherein $R^2$ is ethyl.

16. The compound or salt of claim 13 wherein $R^2$ is vinyl.

17. The compound or salt of claim 13 wherein $R^2$ is cyclopropyl.

18. The compound or salt of claim 4 wherein Z is a side chain of Formula ZB.

19. The compound or salt of claim 18 wherein $Z^5$ is H, methyl or ethyl, and $Z^8$ is H.

20. The compound or salt of claim 19 wherein $D^1$-$D^2$ is —(CH₂)₃—, —(CH₂)₄—, or —CH₂—CH₂—O—CH₂—.

21. The compound or salt of claim 20 wherein $R^2$ is methyl, ethyl, vinyl or cyclopropyl.

22. The compound or salt of claim 21 wherein $Z^5$ and $Z^8$ are H, $D^1$-$D^2$ is —(CH₂)₃—, and $R^2$ is ethyl.

23. The compound or salt of claim 4 wherein Z is a side chain of Formula ZE.

24. The compound or salt of claim 23 wherein $Z^5$ is H, $Z^7$ is H, and $Z^6$ is H or lower alkyl.

25. The compound or salt of claim 4 wherein Z is a side chain of Formula ZH.

26. The compound or salt of claim 25 wherein $Z^1$ is lower alkyl.

27. The compound or salt of claim 26 wherein $D^4$ is —CH₂—, —CH₂—CH₂—, or —O—CH₂—.

28. A pharmaceutical composition comprising a therpeutically effective amount of the compound or salt of claim 1 admixed with at least one pharmaceutically acceptable excipient.

* * * * *